United States Patent
Borek et al.

(10) Patent No.: US 12,186,306 B2
(45) Date of Patent: Jan. 7, 2025

(54) METHODS OF TREATMENT FOR CYSTIC FIBROSIS

(71) Applicant: Vertex Pharmaceuticals Incorporated, Boston, MA (US)

(72) Inventors: Bartlomiej Borek, San Diego, CA (US); Weichao George Chen, San Diego, CA (US); Rudy Gunawan, Apex, NC (US); Eric Haseltine, Melrose, MA (US); Nitin Nair, Hopkinton, MA (US); Porntula Panorchan, Orlando, FL (US); Patrick Sosnay, West Roxbury, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 397 days.

(21) Appl. No.: 17/546,649

(22) Filed: Dec. 9, 2021

(65) Prior Publication Data

US 2022/0184049 A1 Jun. 16, 2022

Related U.S. Application Data

(60) Provisional application No. 63/150,434, filed on Feb. 17, 2021, provisional application No. 63/124,575, filed on Dec. 11, 2020, provisional application No. 63/123,928, filed on Dec. 10, 2020.

(51) Int. Cl.
| | | |
|---|---|---|
| A61K 31/4375 | (2006.01) | |
| A61K 9/20 | (2006.01) | |
| A61K 31/4045 | (2006.01) | |
| A61K 31/47 | (2006.01) | |

(52) U.S. Cl.
CPC ........ *A61K 31/4375* (2013.01); *A61K 9/2054* (2013.01); *A61K 31/4045* (2013.01); *A61K 31/47* (2013.01)

(58) Field of Classification Search
None
See application file for complete search history.

(56) References Cited

U.S. PATENT DOCUMENTS

| 2,677,682 | A | 5/1954 | Fahrenbach et al. |
|---|---|---|---|
| 7,332,612 | B2 | 2/2008 | Dolitzky et al. |
| 8,586,615 | B2 | 11/2013 | Hadida-Ruah et al. |
| 8,865,902 | B2 | 10/2014 | Morgan |
| 9,663,508 | B2 | 5/2017 | Bregman et al. |
| 9,782,408 | B2 | 10/2017 | Miller et al. |
| 9,981,910 | B2 | 5/2018 | Altenbach et al. |
| 10,118,916 | B2 | 11/2018 | Altenbach et al. |
| 10,131,670 | B2 | 11/2018 | Strohbach et al. |
| 10,138,227 | B2 | 11/2018 | Altenbach et al. |
| 10,208,053 | B2 | 2/2019 | Strohbach et al. |
| 10,258,624 | B2 | 4/2019 | Miller et al. |
| 10,570,115 | B2 | 2/2020 | Alcacio et al. |
| 10,654,829 | B2 | 5/2020 | Dhamankar et al. |
| 10,738,030 | B2 | 8/2020 | Bear et al. |
| 10,758,534 | B2 | 9/2020 | Miller et al. |
| 10,793,547 | B2 | 10/2020 | Abela et al. |
| 11,066,417 | B2 | 7/2021 | Clemens et al. |
| 11,179,367 | B2 | 11/2021 | Chu et al. |
| 11,584,761 | B2 | 2/2023 | Angell et al. |
| 11,591,350 | B2 | 2/2023 | Anderson et al. |
| 11,873,300 | B2 | 1/2024 | Shi et al. |
| 2011/0098311 | A1 | 4/2011 | Van Goor et al. |
| 2013/0317000 | A1 | 11/2013 | Chowdhury et al. |
| 2013/0317001 | A1 | 11/2013 | Andrez et al. |
| 2014/0073667 | A1 | 3/2014 | Morgan |
| 2018/0099932 | A1 | 4/2018 | Altenbach et al. |
| 2018/0141954 | A1 | 5/2018 | Strohbach et al. |
| 2018/0162839 | A1 | 6/2018 | Abela et al. |
| 2018/0170938 | A1 | 6/2018 | Strohbach et al. |

(Continued)

FOREIGN PATENT DOCUMENTS

| CL | 201902734 | 1/2020 |
|---|---|---|
| CL | 20200856 | 8/2020 |

(Continued)

OTHER PUBLICATIONS

Morissette et al, Advanced Drug Delivery Reviews, vol. 56, pp. 275-300 (Year: 2004).*

(Continued)

*Primary Examiner* — Zinna Northington Davis

(74) *Attorney, Agent, or Firm* — Finnegan, Henderson, Farabow, Garrett & Dunner, LLP

(57) ABSTRACT

This application describes methods of treating cystic fibrosis or a CFTR mediated disease comprising administering Compound I or a pharmaceutically acceptable salt thereof.

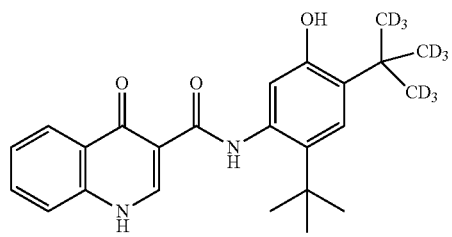

The application also describes pharmaceutical compositions comprising Compound I or a pharmaceutically acceptable salt thereof and optionally comprising one or more additional CFTR modulating agents.

22 Claims, 6 Drawing Sheets

(56) References Cited

U.S. PATENT DOCUMENTS

| | | |
|---|---|---|
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0119253 A1 | 4/2019 | Dhamankar et al. |
| 2019/0153000 A1 | 5/2019 | Munoz et al. |
| 2019/0240197 A1 | 8/2019 | Chu et al. |
| 2019/0248809 A1 | 8/2019 | Clemens et al. |
| 2019/0269683 A1 | 9/2019 | Miller et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |
| 2022/0127247 A1 | 4/2022 | Azimioara et al. |
| 2022/0184049 A1 | 6/2022 | Borek et al. |
| 2022/0313698 A1 | 10/2022 | Abela et al. |
| 2022/0372047 A1 | 11/2022 | Abela et al. |

FOREIGN PATENT DOCUMENTS

| | | |
|---|---|---|
| CL | 202301016 | 6/2023 |
| CN | 102227424 A | 10/2011 |
| CN | 106432213 A | 2/2017 |
| CO | 12038470 | 3/2012 |
| EC | SP19028690 | 4/2019 |
| EC | SP19048759 | 7/2019 |
| EC | SP20003147 | 2/2020 |
| EC | SP20053845 | 9/2020 |
| EP | 0 846 687 A1 | 6/1998 |
| JP | 2014-526500 A | 10/2014 |
| JP | 2020-541909 A | 5/2021 |
| JP | 6896619 | 6/2021 |
| JP | 6916285 | 7/2021 |
| JP | 7061115 | 4/2022 |
| NC | 2018/0000413 | 1/2018 |
| NC | 2018/0012171 | 11/2018 |
| TW | I410423 B | 10/2013 |
| TW | 201713617 A | 4/2017 |
| TW | 201811766 A | 1/2018 |
| WO | WO 2001/090092 A1 | 11/2001 |
| WO | WO 2005/049018 A1 | 6/2005 |
| WO | WO 2005/075435 A1 | 8/2005 |
| WO | WO 2006/002421 A2 | 1/2006 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/127399 A2 | 10/2008 |
| WO | WO 2008/154241 A1 | 12/2008 |
| WO | WO 2009/006315 A1 | 1/2009 |
| WO | WO 2009/038683 A2 | 3/2009 |
| WO | WO 2009/073757 A1 | 6/2009 |
| WO | WO 2009/076142 A2 | 6/2009 |
| WO | WO 2009/108657 A2 | 9/2009 |
| WO | WO 2010/019239 A2 | 2/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/029059 A1 | 3/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2012/027247 A2 | 3/2012 |
| WO | WO 2012/027731 A2 | 3/2012 |
| WO | WO 2012/158885 A1 | 11/2012 |
| WO | WO 2012/170061 A1 | 12/2012 |
| WO | WO 2013/064984 A1 | 5/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/160419 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2014/078842 A1 | 5/2014 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/160945 A1 | 10/2016 |
| WO | WO 2017/009804 A1 | 1/2017 |
| WO | WO 2017/053455 A1 | 3/2017 |
| WO | WO 2017/053711 A2 | 3/2017 |
| WO | WO 2013/038386 A1 | 5/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/208115 A1 | 12/2017 |
| WO | WO 2017/223188 A1 | 12/2017 |
| WO | WO 2018/064632 A1 | 4/2018 |
| WO | WO 2018/080591 A1 | 5/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/183964 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/014352 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/109021 A1 | 6/2019 |
| WO | WO 2019/113089 A1 | 6/2019 |
| WO | WO 2019/113476 A2 | 6/2019 |
| WO | WO 2019/152940 A1 | 8/2019 |
| WO | WO 2019/161078 A1 | 8/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/102346 A1 | 5/2020 |
| WO | WO 2020/128925 A1 | 6/2020 |
| WO | WO 2020/191227 A1 | 9/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2021/097054 A1 | 5/2021 |
| WO | WO 2021/097057 A1 | 5/2021 |
| WO | WO 2022/032068 A1 | 2/2022 |
| WO | WO 2022/036060 A1 | 2/2022 |
| WO | WO 2022/076620 A2 | 4/2022 |
| WO | WO 2022/076621 A2 | 4/2022 |
| WO | WO 2022/076622 A2 | 4/2022 |
| WO | WO 2022/076624 A2 | 4/2022 |
| WO | WO 2022/076625 A2 | 4/2022 |
| WO | WO 2022/076626 A2 | 4/2022 |

OTHER PUBLICATIONS

Borhade, Sanjay R., et al., "Synthesis of Novel Aryl and Heteroaryl Acyl Sulfonimidamides via Pd-Catalyzed Carbonylation Using a Nongaseous Precursor," Organic Letters, 2013, vol. 15, No. 5, pp. 1056-1059, XP055374206A, © 2013 American Chemical Society,

(56) References Cited

OTHER PUBLICATIONS

ISSN: 1523-7060, DOI:10.1021/014/00049m, published on web Feb. 13, 2013.
International Patent Application No. PCT/US2021/045691: International Search Report and Written Opinion, mailed Dec. 13, 2021 (16 pages).
U.S. Appl. No. 18/493,667, filed Oct. 24, 2023, by Shi et al.
Alberti, C. and Tironi, C. (1964) "Sulfanilammidi Pirazoliche, VI. 1-(Tolil)-sulfanilamidopirazoli derivati dal 3-aminopirazolo, dal 4-aminopirazolo e dal 3-metil-5-aminopirazolo," *Il Farmaco—Ed. Sc.* 29(7), 618-637.
Alberti, C. and Tironi, C. (1971) "Sulfanilammidi Pirazoliche," *Il Farmaco—Ed. Sc.* 26(1), 66-88.
Bastin, R.J. et al., "Salt selection and optimization procedures for pharmaceutical new chemical entities," *Org. Pro. Res. Dev.* 2000, 4(5), 427-435.
Braker, W. et al. (1947) "Substituted Sulfanilamidopyrimidines," J. Am. Chem. Society, 69, 3072-3075.
Chen, L. et al. (2014) "Synthesis and Antimicrobial Activity of the Hybrid Molecules between Sulfonamides and Active Antimicrobial Pleuromutilin Derivative," Chemical Biology and Drug Design, 86(2), 239-245.
Cherepakha, A.Y. et al. (2018) "Hetaryl Bromides Bearing the SO2F Group—Versatile Substrates for Palladium-Catalyzed C-C Coupling Reactions", *Eur J Org Chem*, 47: 6682-6692.
Chio, L. et al. (1996) "Identification of a Class of Sulfonamides Highly Active Against Dihydropteroate Synthase from *Toxoplasma gondii, Pneumocystis carinii,* and *Mycobacterium avium*," Antimicrobial Agents and Chemotherapy, American Society for Microbiology, 40(3), 727-733.
Donaldson, S.H. et al. (2017) "Tezacaftor/Ivacaftor in Subjects with Cystic Fibrosis and F508del/F508del-CFTR or F508del/G551D-CFTR", *Am. J. Respir. Crit. Care Med.*, 197(2): 214-224.
Gage, J. C. et al. (1947), "2-P-Aminobenzenesulphonamido-4 : 6-Dimethoxypyrimidine: Experimental Evaluation," British Journal of Pharmacology and Chemotherapy, 2(3), 149-162.
Ghorab, Mostafa at al. (2017) "Aromatase inhibitors and apoptotic inducers: Design, synthesis, anticancer activity and molecular modeling studies of novel phenothiazine derivatives carrying sulfonamide moiety as hybrid molecules," *Eur. J. Med. Chem.*, 134, 304-315.
Gomes, Paula et al. (2003) "Amino acids as selective sulfonamide acylating agents," Tetrahedron, 59(38), 7473-7480.
Hassan, H. H. A. M. and Soliman, R. (2000) "Synthesis and GC-EIMS Analyses of Optically Pure 3-Hydroxy-2-azetidinones Having N-sulfonamide Drugs Side Chain," *Synthetic Communications*, 30(14), 2465-2478.
International Patent Application No. PCT/US2019/018042: International Search Report and Written Opinion, mailed Apr. 17, 2019 (10 pages).
International Patent Application No. PCT/US2019/061171: International Search Report and Written Opinion, mailed Feb. 12, 2020 (14 pages).
International Patent Application No. PCT/U2020/026331: International Search Report and Written Opinion, mailed May 29, 2020 (14 pages).
International Patent Application No. PCT/US2021/053853: International Search Report and Written Opinion, mailed Dec. 21, 2021 (12 pages).
International Patent Application No. PCT/US2021/053855: International Search Report and Written Opinion, mailed Jan. 3, 2022 (12 pages).
International Patent Application No. PCT/US2021/053856: International Search Report and Written Opinion, mailed Dec. 22, 2021 (12 pages).
International Patent Application No. PCT/US2021/053858: International Search Report and Written Opinion, mailed Mar. 17, 2022 (14 pages).
International Patent Application No. PCT/US2021/053860: International Search Report and Written Opinion, mailed Dec. 23, 2021 (12 pages).
International Patent Application No. PCT/US2021/053861: International Search Report and Written Opinion, mailed Dec. 22, 2021 (12 pages).
International Patent Application No. PCT/US2021/053862: International Search Report and Written Opinion, mailed Dec. 22, 2021 (12 pages).
International Patent Application No. PCT/US2021/053863: International Search Report and Written Opinion, mailed Feb. 4, 2022 (16 pages).
International Patent Application No. PCT/US2021/053864: International Search Report and Written Opinion, mailed Mar. 15, 2022 (17 pages).
International Patent Application No. PCT/US2021/053865: International Search Report and Written Opinion, mailed Jan. 26, 2022 (16 pages).
International Patent Application No. PCT/US2021/062687: International Search Report and Written Opinion, mailed Apr. 4, 2022 (14 pages).
Kim, T. et al. (2018) "Sulfonamidation of Aryl and Heteroaryl Halides through Photosensitized Nickel Catalysis," *Agewandte Chemie*, 57, 3488-3492.
Newkome, G.R. et al. (1979) "Nicotinic Acid Crown Ethers. Synthesis, Reactions, and Complexation of Nicotinonitrile Macrocycles", *J Org Chem*, 44(15): 2639-2697.
Nishida, H. et al. (2017) "Exploration of pyrrole derivatives to find an effective potassium competitive acid blocker with moderately long-lasting suppression of gastric acid secretion", *Bioorg Med Chem*, 25(13): 3447-3460.
"A phase 1/2 study of VX-121 in healthy subjects and in subjects with cystic fibrosis", EU Clinical Trials Register, May 3, 2019 (May 3, 2019), XP055903414, Retrieved from the Internet: URL:https://www.clinicaltrialsregister.eu/ctr-search/trial/2018-000126-55/NL [retrieved on Mar. 21, 2022].
"A Phase 2 Study to Evaluate Efficacy and Safety of VX-561 in Subjects Aged 18 Years and Older With Cystic Fibrosis", ClinicatTials. gov, Apr. 11, 2019 (Apr. 11, 2019), XP055903562, Retrieved from the Internet: URL:https://clinicaltrials.gov/ct2/show/NCT03911713 [retrieved on Mar. 21, 2022].
Prashantha, G. et al. (2017) "Selective IKur Inhibitors for the Potential Treatment of Atrial Fibrillation: Optimization of the Phenyl Quinazoline Series Leading to Clinical Candidate 5-[5-Phenyl-4-(pyridin-2-ylmethylamino)quinazolin-2-yl]pyridine-3-sulfonamide", *J Med Chem*, 60(9): 3795-3803.
Rewcastle, G.W. et al. (1996) "Tyrosine Kinase Inhibitors. 10. Isomeric 4-[(3-Bromophenyl)amino]pyrido[d]-pyrimidines are Potent ATP Binding Site Inhibitors of the Tyrosine Kinase Function of the Epidermal Growth Factor Receptor", *J Med Chem*, 39(9): 1823-1835.
Raiziss, GW et al. (1942) "N1-Sulfanilylaminoalkylpyrimidines," *J. Am. Chem. Soc.* 64, 2340-2342.
Rose, F. L. et al. (1946) "P-Aminobenzenesulphonamide Derivatives of Pyrimidines as Antibacterial Agents," *J. Am. Chem. Soc.*, 81-85.
Sprague, JM et al. (1941) "Sulfonamido derivatives of thiazoles," *J. Am. Chem. Soc.* 63, 578-580.
Sprague, JM et al. (1941) "Sulfonamido derivatives of pyrimidines," *J. Am. Chem. Soc.* 63, 3028-3030.
"A Study to Evaluate the Safety and Efficacy of VX-121 Combination Therapy in Subjects with Cystic Fibrosis", ClinicalTrials. gov, Apr. 30, 2019 (Apr. 30, 2019), XP55903330, Retrieved from the Internet: URL:https://clinicaltrials.gov/ct2/show/NCT03912233 [retrieved on Mar. 21, 2022].
Sugasawa, S et al. (1949) "Reaction between sulfaguanidine and 1,3-keto aldehydes. I. Synthesis of 2-sulfanilamido-4-methylpyrimidine," 69, 82-85.
"Symdeko in Cystic Fibrosis Patients", ClinicalTrials.gov, Jul. 23, 2018 (Apr. 23, 2018), XP055661778, Retrieved from the Internet: URL:https://clinicaltrials.gov/ct2/show/record/NCT03506061 [retrieved on Jan. 24, 2020].

(56) References Cited

OTHER PUBLICATIONS

Tani, C et al. (1950) "Syntheses of sulfanilamide derivatives containing diphenylene oxide," *Journal of the Pharmaceutical Society of Japan*, 70, 126-127.
U.S. Appl. No. 17/600,829, filed Oct. 1, 2021, by Abela et al.
U.S. Appl. No. 16/992,419, filed Aug. 13, 2021, by Angell et al.
U.S. Appl. No. 16/992,441, filed Aug. 13, 2021, by Shi et al.
U.S. Appl. No. 16/992,448, filed Aug. 13, 2021, by Anderson et al.
U.S. Appl. No. 16/992,675, filed Aug. 13, 2021, by Abela et al.
U.S. Appl. No. 17/546,649, filed Dec. 9, 2021, by Borek et al.
Masakuni Matsuoka, Fundamentals & Application of Polymorphic Crystals, Popular Edition, 1st Printing, CMC Publishing Co., Ltd. Oct. 22, 2010, pp. 105-117, pp. 181-191.

\* cited by examiner

METHODS OF TREATMENT FOR CYSTIC FIBROSIS

This application claims the benefit of priority to U.S. Provisional Application No. 63/123,928, filed Dec. 10, 2020; U.S. Provisional Application No. 63/124,575, filed Dec. 11, 2020; and U.S. Provisional Application No. 63/150,434, filed Feb. 17, 2021, the contents of each of which are incorporated by reference in their respective entireties.

The invention provides pharmaceutical compositions for and methods of treating cystic fibrosis.

Cystic fibrosis (CF) is a recessive genetic disease that affects approximately 83,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified. CF mutations are listed in the "Cystic Fibrosis Mutation Database," located at http://www.genet.sickkids.on.ca/app, which is incorporated herein by reference in its entirety. The most prevalent disease-causing mutation is a deletion of phenylalanine at position 508 of the CFTR amino acid sequence and is commonly referred to as the F508del mutation. This mutation occurs in approximately 90% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC (epithelial sodium channel) and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride. Because water is probably never actively transported itself, its flow across epithelia depends on tiny transepithelial osmotic gradients generated by the bulk flow of sodium and chloride.

A number of CFTR modulating compounds have recently been identified. However, compounds that can treat or reduce the severity of the cystic fibrosis and other CFTR mediated diseases, and particularly the more severe forms of these diseases, are still needed.

Thus, one aspect of the disclosure provides pharmaceutical composition comprising 250 mg of CFTR potentiator compound, N-(2-(tert-butyl)-5-hydroxy-4-(2-(methyl-d3) propan-2-yl-1,1,1,3,3,3-d6)phenyl)-4-oxo-1,4-dihydroquinoline-3-carboxamide (Compound I) or an equivalent amount of a pharmaceutically acceptable salt thereof. Compound I can be depicted as having the following structure:

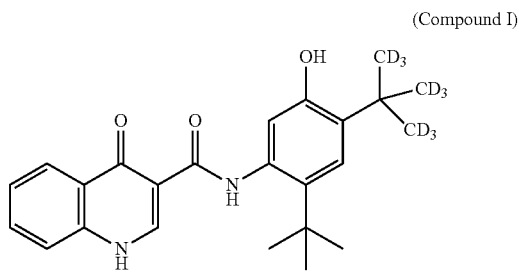 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

(Compound I)

It has been discovered that 250 mg of Compound I administered once daily may improve the therapeutic profile as measured by sweat chloride (SwCl), compared to 150 mg q12 h of ivacaftor (i.e., twice daily at 12 hour intervals) and 150 mg qd of Compound I (i.e., once daily).

Other aspects of the disclosure provide pharmaceutical compositions comprising 250 mg of Compound I or an equivalent amount of a pharmaceutically acceptable salt thereof, that further include at least one additional active pharmaceutical ingredient and/or at least one carrier. Yet other aspects of the disclosure are methods of treating the CFTR-mediated disease cystic fibrosis comprising administering Compound I or an equivalent amount of a pharmaceutically acceptable salt thereof, optionally as part of a pharmaceutical composition comprising at least one additional component, to a subject in need thereof. In some embodiments, the pharmaceutical compositions of the invention comprise 250 mg of Compound I (or an equivalent amount of a pharmaceutically acceptable salt thereof), 21.24 mg of Compound II, calcium salt hydrate Form D, and 100 mg of Compound III (or an equivalent amount of a pharmaceutically acceptable salt thereof). In some embodiments, the pharmaceutical compositions of the invention comprise 125 mg of Compound I (or an equivalent amount of a pharmaceutically acceptable salt thereof), 10.62 mg of Compound II, calcium salt hydrate Form D, and 50 mg of Compound III (or an equivalent amount of a pharmaceutically acceptable salt thereof).

One embodiment provides a method of treating the CFTR-mediated disease cystic fibrosis comprising administering 250 mg of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound I), alone or in combination with 21.24 mg of (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione (Compound II) calcium salt hydrate Form D, and/or 50-100 mg of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound III).

In some embodiments, 250 mg of Compound I (or an equivalent amount of a pharmaceutically acceptable salt thereof) is administered in the same composition with 20 mg of Compound II calcium salt hydrate Form D. In some embodiments, 250 mg of Compound I is administered in the same composition with 21.24 mg of Compound II calcium salt hydrate Form D and 100 mg of Compound III (or an equivalent amount of a pharmaceutically acceptable salt thereof). In some embodiments, a composition comprising 250 mg of Compound I (or an equivalent amount of a pharmaceutically acceptable salt thereof) is co-administered with a separate composition comprising 21.24 mg of Compound II calcium salt hydrate Form D and/or 100 mg of Compound III (or an equivalent amount of a pharmaceutically acceptable salt thereof). In some embodiments 250 mg of Compound I is administered in the same composition with 21.24 mg of Compound II calcium salt hydrate Form D and 100 mg of Compound III (or an equivalent amount of a pharmaceutically acceptable salt thereof). In some embodiments, the 250 mg of Compound I, 21.24 mg of Compound II calcium salt hydrate Form D. and 100 mg of Compound III (or an equivalent amount of a pharmaceutically acceptable salt thereof) are administered once daily in two equivalent dose compositions.

DEFINITIONS

Figure 1:
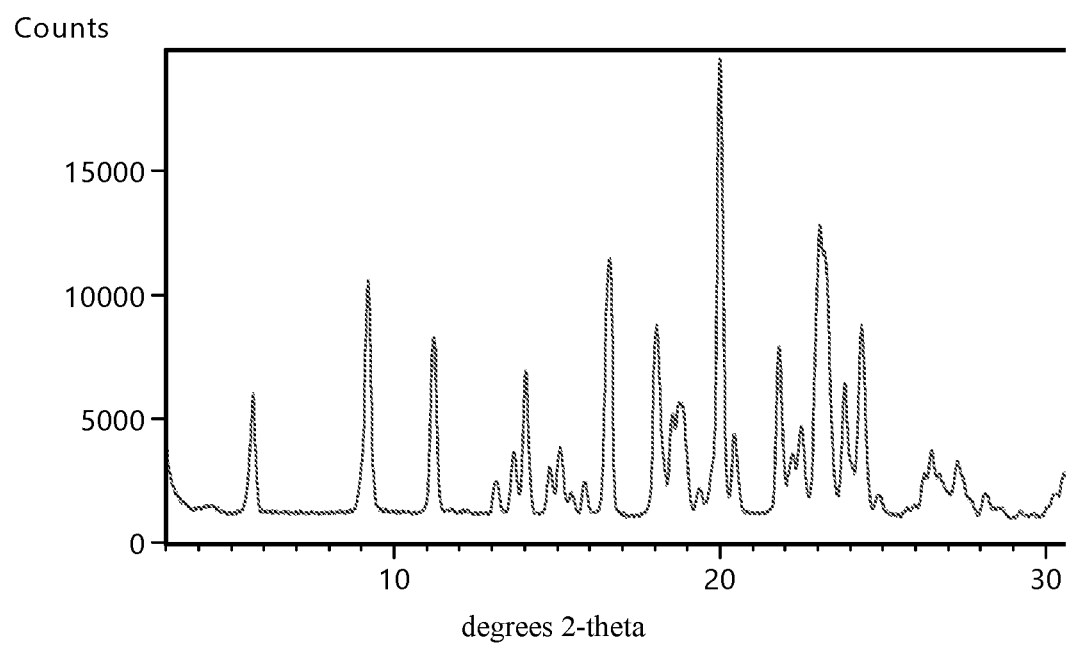
FIG. 1 provides an XRPD pattern of crystalline Compound I (free form) Form A.

"Compound I" as used throughout this disclosure refers to N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide, which can be depicted as having the following structure:

(Compound I)

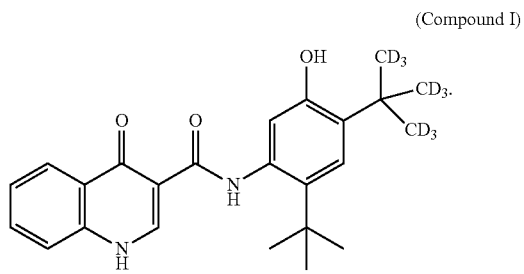 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

Compound I may be in the form of a pharmaceutically acceptable salt. Compound I and its pharmaceutically acceptable salts have been previously described in U.S. Pat. Nos. 8,865,902, 9,181,192, and 9,512,079, and International Patent Publication Nos. WO 2012/158885, WO 2014/078842, WO 2017/053455, and WO 2018/080591, each of which are incorporated herein by reference.

In some embodiments, the isotopic enrichment factor of each deuterium in Compound I may vary. The term "isotopic enrichment factor" refers to the ratio between the isotopic abundance and the natural abundance of a specified isotope. In some embodiments, the isotopic enrichment factor for each designated deuterium atom in Compound I is at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

"Compound II" as used herein, refers to (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione, which can be depicted with the following structure:

(Compound II)

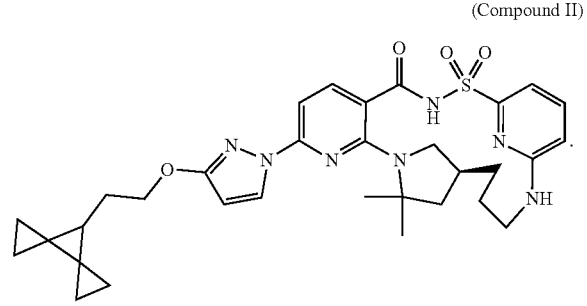 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

Compound II and deuterated derivatives and pharmaceutically acceptable salts thereof were first described in International Patent Publication WO 2019/161078 (incorporated herein by reference).

In some embodiments, Compound II is in the form of calcium salt hydrate Form D. 20 mg of Compound II is equivalent to 21.24 mg of Compound II calcium salt hydrate From D. In some embodiments, Compound II calcium salt hydrate Form D is characterized by an X-ray powder diffractogram having signals at 6.1±0.2 degrees two-theta, 16.2±0.2 degrees two-theta, and 22.8±0.2 degrees two-theta. In some embodiments, Compound II calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) one or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

In some embodiments, Compound II calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) two or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta. In some embodiments, Compound II calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) three or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta. In some embodiments, Compound II calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) four or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

In some embodiments, Compound II calcium salt hydrate Form D is characterized by an X-ray powder diffractogram having signals at 6.1±0.2 degrees two-theta, 16.2±0.2 degrees two-theta, and 22.8±0.2 degrees two-theta, and 27.6±0.2 degrees two-theta. In some embodiments, Compound II calcium salt hydrate Form D is characterized by an X-ray powder diffractogram having signals at 6.1±0.2 degrees two-theta, 15.5±0.2 degrees two-theta, 16.2±0.2 degrees two-theta, 19.7±0.2 degrees two-theta, 22.8±0.2 degrees two-theta, and 27.6±0.2 degrees two-theta. In some embodiments Compound II calcium salt hydrate Form D is characterized by an X-ray powder diffractogram substantially similar to FIG. 5.

In some embodiments, Compound II calcium salt hydrate Form D is characterized as having a $^{13}$C solid state nuclear magnetic resonance ($^{13}$C ssNMR) spectrum with one or more peaks selected from: 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound II calcium salt hydrate Form D is characterized as having a $^{13}$C ssNMR spectrum with two or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound II calcium salt hydrate Form D is characterized as having a $^{13}$C ssNMR spectrum with three or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound II calcium salt hydrate Form D is characterized as having a $^{13}$C ssNMR spectrum with four or more peaks selected from: 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound II calcium salt hydrate Form D is characterized as having a $^{13}$C ssNMR spectrum with five or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound II calcium salt hydrate Form D is characterized as having a $^{13}$C ssNMR spectrum with six or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm.

In some embodiments, Compound II calcium salt hydrate Form D is characterized as having a $^{13}$C ssNMR spectrum with one or more peaks selected from 130.2±0.2 ppm, 125.6±0.2 ppm, and 35.0±0.2 ppm. In some embodiments, Compound II calcium salt hydrate Form D is characterized as having a $^{13}$C ssNMR spectrum with two or more peaks selected from 130.2±0.2 ppm, 125.6±0.2 ppm, and 35.0±0.2 ppm. In some embodiments, Compound I calcium salt hydrate Form D is characterized as having a $^{13}$C ssNMR spectrum with peaks at 130.2±0.2 ppm, 125.6±0.2 ppm, and 35.0±0.2 ppm.

In some embodiments, Compound II calcium salt hydrate Form D is characterized as having a $^{13}$C ssNMR spectrum with (a) a peak at 130.2±0.2 ppm, 125.6±0.2 ppm, and/or 35.0±0.2 ppm; and (b) a peak at 176.9±0.2 ppm, 160.9±0.2 ppm, 142.0±0.2 ppm, and/or 98.6±0.2 ppm. In some embodiments, Compound II calcium salt hydrate Form D is characterized as having a $^{13}$C ssNMR spectrum with (a) a peak at 130.2±0.2 ppm, 125.6±0.2 ppm, and/or 35.0±0.2 ppm; and (b) peaks at 176.9±0.2 ppm, 160.9±0.2 ppm, 142.0±0.2 ppm, and 98.6±0.2 ppm. In some embodiments, Compound II calcium salt hydrate Form D is characterized as having a $^{13}$C ssNMR spectrum with (a) peaks at 130.2±0.2 ppm, 125.6±0.2 ppm, and 35.0±0.2 ppm; and (b) a peak at 176.9±0.2 ppm, 160.9±0.2 ppm, 142.0±0.2 ppm, and/or 98.6±0.2 ppm. In some embodiments, Compound II calcium salt hydrate Form D is characterized as having a $^{13}$C ssNMR spectrum with peaks at 130.2±0.2 ppm, 125.6±0.2 ppm, 35.0±0.2 ppm, 176.9±0.2 ppm, 160.9±0.2 ppm, 142.0±0.2 ppm, and 98.6±0.2 ppm.

Figure 6:
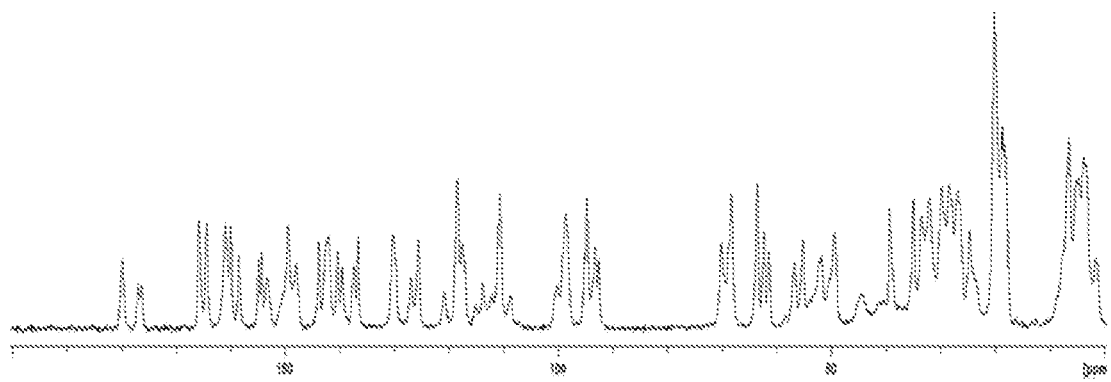
FIG. 6 shows a $^{13}C$ solid state NMR spectrum of Compound I calcium salt hydrate Form D.

In some embodiments, Compound II calcium salt hydrate Form D is characterized by a $^{13}$C ssNMR spectrum substantially similar to FIG. 6.

In some embodiments, Compound II calcium salt hydrate Form D is characterized by a triclinic crystal system, a P1 space group, and the following unit cell dimensions measured at by 100 K on a Bruker diffractometer equipped with Cu $K_\alpha$ radiation ($\lambda$=1.5478 Å) and a Complementary metal-oxide-semiconductor (CMOS) detector:

| a | 12.78 ± .01 Å | α | 64.93 ± .02° |
|---|---|---|---|
| b | 16.64 ± .01 Å | β | 75.10 ± .02° |
| c | 18.19 ± .01 Å | γ | 68.22 ± .02°. |

"Compound III" as used throughout this disclosure refers (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide:

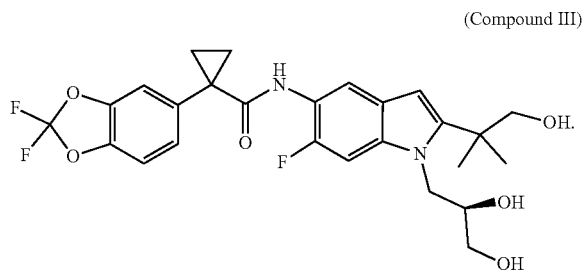 [SMILES: CC(C)(CO)c1cc2cc(NC(=O)C3(c4ccc5c(c4)OC(F)(F)O5)CC3)c(F)cc2n1C[C@@H](O)CO]

(Compound III)

In some embodiments, Compound III is in the form of a pharmaceutically acceptable salt. Compound III and its pharmaceutically acceptable salts were previously disclosed in International Patent Publication WO 2010/053471 (incorporated herein by reference).

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has the particular mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds II and III disclosed herein are CFTR correctors.

As used herein, the term "CFTR potentiator" refers to a compound that increases the channel activity of CFTR protein located at the cell surface, resulting in enhanced ion transport. Compound I disclosed herein is a CFTR potentiator.

As used herein, the term "active pharmaceutical ingredient" or "therapeutic agent" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describes pharmaceutically acceptable salts in detail in *J. Pharmaceutical Sciences*, 1977, 66, 1-19.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e. the material is not crystalline, but is amorphous, as determined by XRPD). Instead, one or several broad peaks (e.g. halos) may appear in the XRPD pattern of the material. See US 2004/0006237 for a comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, Raman spectroscopy, infrared spectroscopy, and solid-state NMR may be used to characterize crystalline or amorphous forms.

In some embodiments, a solid material may comprise a mixture of crystalline solids and amorphous solids. A solid material prepared to comprise an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRPD, may contain indicators of both crystalline and amorphous solids.

As used herein, the term "substantially amorphous" refers to a solid material having little or no long-range order in the position of its molecules. For example, substantially amorphous materials have less than 15% crystallinity (e.g., less than 10% crystallinity, less than 5% crystallinity, or less than 2% crystallinity). It is also noted that the term 'substantially amorphous' includes the descriptor, 'amorphous', which refers to materials having no (0%) crystallinity.

As used herein, the term "substantially crystalline" refers to a solid material having little or no amorphous molecules. For example, substantially crystalline materials have less than 15% amorphous molecules (e.g., less than 10% amorphous molecules, less than 5% amorphous molecules, or less than 2% amorphous molecules). It is also noted that the term "substantially crystalline" includes the descriptor "crystalline," which refers to materials that are 100% crystalline form.

As used herein, the term "XRPD" refers to the analytical characterization method of X-ray powder diffraction. XRPD patterns disclosed herein were recorded at ambient conditions in transmission or reflection geometry using a diffractometer.

As used herein, the term "ambient conditions" means room temperature, open air condition and uncontrolled humidity condition. The terms "room temperature" and "ambient temperature" mean 15° C. to 30° C.

As used herein, the terms "X-ray powder diffractogram," "X-ray powder diffraction pattern," "XRPD pattern,"

"XRPD spectrum" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) selected from . . . ."

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta" refer to X-ray reflection positions as measured and observed in X-ray powder diffraction experiments (° 2θ).

The repeatability of the measured angular values is in the range of ±0.2° 2θ, i.e., the angular value can be at the recited angular value+0.2 degrees two-theta, the angular value−0.2 degrees two-theta, or any value between those two end points (angular value+0.2 degrees two-theta and angular value−0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta) generally mean that value is identified as ±0.2 degrees two-theta of the reported value, an art-recognized variance.

As used herein, a $^{13}C$ ssNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in ssNMR spectra even for the same crystalline form. Thus, those of ordinary skill in the art will understand that the chemical shifts in ssNMR spectra (in parts per million (ppm) referred to herein) generally mean that value is identified as ±0.2 ppm of the reported value, an art-recognized variance.

The term "X-ray powder diffractogram having a signal at . . . two-theta values" as used herein refers to an XRPD pattern that contains X-ray reflection positions as measured and observed in X-ray powder diffraction experiments (° two-theta).

As used herein, the term "DSC" refers to the analytical method of Differential Scanning calorimetry.

As used herein, the term "solvent" refers to any liquid in which the product is at least partially soluble (solubility of product >1 g/1).

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

The terms "patient" and "subject" are used interchangeably and refer to an animal including humans.

As used herein, the terms "treatment," "treating," and the like generally mean the improvement of CF or its symptoms or lessening the severity of CF or one or more of the symptoms of CF in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrently with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "100 mg of at least one compound chosen from Compound I and pharmaceutically acceptable salts thereof"

includes 100 mg of Compound I and a concentration of a pharmaceutically acceptable salt of Compound I equivalent to 100 mg of Compound I.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teoclate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

Methods of Treatment

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes.

In some embodiments, disclosed herein methods of treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

In some embodiments, the patient is heterozygous and has an F508del mutation on one allele and a mutation on the other allele selected from Table 2:

TABLE 2

| CFTR Mutations Mutation | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C (G970R) | 3600 + 2insT |
| 405 + 1G→A | 1249 − 1G→A | 1811 + 1.6kbA→G | 3120G→A 3120 + | 3850 − 1G→A |

TABLE 2-continued

CFTR Mutations
Mutation

| | | | | |
|---|---|---|---|---|
| 405 + 3A→C | 1341 + 1G→A | 1811 + 1643G→T | 1G→A 3121 − 2A→G | 4005 + 1G→A |
| 406 − 1G→A | 1525 − 2A→G | 1812 − 1G→A | | 4374 + 1G→Y |
| 621 + 1G→T | 1525 − 1G→A | 1898 + 1G→A | | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365 − 366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |

| | | |
|---|---|---|
| CFTRdele1 | CFTRdele16-17b | 1461ins4 |
| CFTRdele2 | CFTRdele17a,17b | 1924del7 |
| CFTRdele2,3 | CFTRdele17a-18 | 2055del9→A |
| | | 2105- |
| CFTRdele2-4 | CFTRdele19 | 2117del13insAGAAA |
| CFTRdele3-10,14b-16 | CFTRdele19-21 | 2372del8 |
| CFTRdele4-7 | CFTRdele21 | 2721del11 |
| CFTRdele4-11 | CFTRdele22-24 | 2991del32 |
| CFTR50kbdel | CFTRdele22,23 | 3667ins4 |
| CFTRdup6b-10 | 124del23bp | 4010del4 |
| CFTRdele11 | 602del14 | 4209TGTT→AA |
| CFTRdele1 3,14a | 852del22 | |
| CFTRdele14b-17b | 991del5 | |

| | | | |
|---|---|---|---|
| A46D | V520F | Y569D | N1303K |
| G85E | A559T | L1065P | |
| R347P | R560T | R1066C | |
| L467P | R560S | L1077P | |
| I507del | A561E | M1101K | |

In some embodiments, the patient is heterozygous and has an F508del mutation on one allele and a mutation on the other allele selected from Table 3.

TABLE 3

| | | |
|---|---|---|
| 711 + 3A > G | L206W | K1060T |
| 2789 + 5G > A | R347H | A1067T |
| 3272 − 26A > G | R352Q | G1069R |
| 3849 + 10kbC > T | A455E | R1070Q |
| E56K | S549N | R1070W |
| P67L | S549R | F1074L |
| R74W | G551D | D1152H |
| D110E | G551S | G1244E |
| D110H | D579G | S1251N |
| R117C | E831X | S1255P |
| R117H | S945L | D1270N |
| G178R | S977F | G1349D |
| E193K | F1052V | |

In some embodiments, the patient has at least one mutation selected from Table 4. In some embodiments, the patient has no F508del mutation and at least one mutation selected from Table 4.

TABLE 4

| | | |
|---|---|---|
| 3141del9 | E822K | G1244E |
| 546insCTA | F191V | G1249R |
| A46D | F311del | G1349D |
| A120T | F311L | H139R |

TABLE 4-continued

| | | |
|---|---|---|
| A234D | F508C | H199Y |
| A349V | F508C; S1251N [†] | H939R |
| A455E | F575Y | H1054D |
| A554E | F1016S | H1085P |
| A1006E | F1052V | H1085R |
| A1067T | F1074L | H1375P |
| D110E | F1099L | I148T |
| D110H | G27R | I175V |
| D192G | G85E | I336K |
| D443Y | G126D | I502T |
| D443Y; G576A; R668C [†] | G178E | I601F |
| D579G | G178R | I618T |
| D614G | G194R | I807M |
| D836Y | G194V | I980K |
| D924N | G314E | I1027T |
| D979V | G463V | I1139V |
| D1152H | G480C | I1269N |
| D1270N | G551D | I1366N |
| E56K | G551S | K1060T |
| E60K | G576A | L15P |
| E92K | G576A; R668C [†] | L165S |
| E116K | G622D | L206W |
| E193K | G628R | L320V |
| E403D | G970D | L346P |
| E474K | G1061R | L453S |
| E588V | G1069R | L967S |
| L997F | R117P | S945L |
| L1077P | R170H | S977F |
| L1324P | R258G | S1159F |
| L1335P | R334L | S1159P |
| L1480P | R334Q | S1251N |
| M152V | R347H | S1255P |
| M265R | R347L | T338I |
| M952I | R347P | T1036N |
| M952T | R352Q | T1053I |
| M1101K | R352W | V201M |
| P5L | R553Q | V232D |
| P67L | R668C | V456A |
| P205S | R751L | V456F |
| P574H | R792G | V562I |
| Q98R | R933G | V754M |
| Q237E | R1066H | V1153L |
| Q237H | R1070Q | V1240G |
| Q359R | R1070W | V1293G |
| Q1291R | R1162L | W361R |
| R31L | R1283M | W1098C |
| R74Q | R1283S | W1282R |
| R74W | S13F | Y109N |
| R74W; D1270N [†] | S341P | Y161D |
| R74W; V201M [†] | S364P | Y161S |
| R74W; V201M; D1270N [†] | S492F | Y563N |
| R75Q | S549N | Y1014C |
| R117C | S549R | Y1032C |
| R117G | S589N | |
| R117H | S737F | |
| R117L | S912L | |

[†] Complex/compound mutations where a single allele of the CFTR gene has multiple mutations; these exist independent of the presence of mutations on the other allele.

In some embodiments, the disclosure also is directed to methods of treatment using isotope-labelled derivatives of the afore-mentioned compounds. In some embodiments, isotope-labelled derivatives of the afore-mentioned compounds or pharmaceutically acceptable salts thereof, wherein one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}F$, $^{32}F$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One aspect disclosed herein provides methods of treating cystic fibrosis and other CFTR mediated diseases comprising administering 250 mg of Compound I (or an equivalent amount of a pharmaceutically acceptable salt). In some embodiments, the 250 mg of Compound I (or an equivalent amount of a pharmaceutically acceptable salt) is administered in a single dose daily alone or in combination with another CFTR modulator. In some embodiments, the 250 mg of Compound I (or an equivalent amount of a pharmaceutically acceptable salt) is administered as two 125 mg doses once daily alone or in combination with another CFTR modulator.

One aspect disclosed herein provides methods of treating cystic fibrosis and other CFTR mediated diseases with daily administration of 250 mg of Compound I (or an equivalent amount of a pharmaceutically acceptable salt thereof) in combination with 21.24 mg of Compound II calcium salt hydrate Form D and 100 mg of Compound III (or an equivalent amount of a pharmaceutically acceptable salt thereof). In some embodiments, the 250 mg of Compound I (or an equivalent amount of a pharmaceutically acceptable salt thereof), 21.24 mg of Compound II calcium salt hydrate Form D, and 100 mg of Compound III (or an equivalent amount of a pharmaceutically acceptable salt thereof) are administered daily in separate pharmaceutical compositions. In some embodiments, the 250 mg of Compound I (or an equivalent amount of a pharmaceutically acceptable salt thereof), 21.24 mg of Compound II calcium salt hydrate Form D, and 100 mg of Compound III (or an equivalent amount of a pharmaceutically acceptable salt thereof), are administered in a single pharmaceutical composition daily. In some embodiments the 250 mg of Compound I (or an equivalent amount of a pharmaceutically acceptable salt thereof), 21.24 mg of Compound II calcium salt hydrate Form D, and 100 mg of Compound III (or an equivalent amount of a pharmaceutically acceptable salt thereof) are administered together in two equivalent pharmaceutical compositions once daily.

Pharmaceutical Compositions

Another aspect of the invention provides pharmaceutical compositions for use in treating cystic fibrosis. In some embodiments, the pharmaceutical composition of the invention comprises 250 mg of Compound I (or an equivalent amount of a pharmaceutically acceptable salt thereof). In some embodiments, the pharmaceutical composition of the invention comprises 125 mg of Compound I (or an equivalent amount of a pharmaceutically acceptable salt thereof).

In some embodiments, the pharmaceutical composition of the invention comprises 250 mg of Compound I, 21.24 mg of Compound II calcium salt hydrate Form D, and 100 mg of Compound III. In some embodiments, the pharmaceutical composition of the invention comprises 125 mg of Compound, 10.62 mg of Compound II calcium salt hydrate Form D, and 50 mg of Compound III.

In some embodiments, the pharmaceutical compositions (e.g., tablets) disclosed herein comprise a first solid dispersion (e.g., a spray dried dispersion) comprising Compound I and a second solid dispersion (e.g., a spray dried dispersion) comprising Compound III. Solid dispersions of a non-deuterated analog of Compound I and methods of preparing such dispersions are disclosed in PCT Publication No. WO 2007/079139, incorporated herein by reference. These same solid dispersions are suitable for use with Compound I. Solid dispersions of Compound III and methods of preparing thereof are disclosed in PCT Publication Nos. WO 2011/119984 and WO 2015/160787, incorporated herein by reference.

In some embodiments, the pharmaceutical composition of the invention comprises about 39.9 wt % by weight of the composition of a solid dispersion comprising Compound I (wherein the solid dispersion comprises 80 wt % Compound I, 19.5 wt % hypromellose acetate succinate, and 0.5 wt % sodium lauryl sulfate, by weight of the solid dispersion), about 2.7 wt % by weight of the composition of Compound II calcium salt hydrate Form D, and about 16.0 wt % by weight of the composition of a solid dispersion comprising Compound III (wherein the solid dispersion comprises 80 wt % Compound I and 20 wt % hypromellose, by weight of the solid dispersion).

Any suitable pharmaceutical compositions known in the art can be used for Compound I, Compound II calcium salt hydrate Form D, and Compound III. Some exemplary pharmaceutical compositions for Compound I and its pharmaceutically acceptable salts can be found in U.S. Pat. Nos. 8,865,902, 9,181,192, 9,512,079, WO 2017/053455, and WO 2018/080591, all of which are incorporated herein by reference. Exemplary pharmaceutical compositions comprising Compound II and its pharmaceutically acceptable salts are disclosed in WO 2019/161078 and WO 2020/102346. Exemplary pharmaceutical compositions for Compound III and its pharmaceutically acceptable salts are disclosed in WO 2011/119984 and WO 2014/014841, incorporated herein by reference.

Pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. *Remington: The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In one embodiment, the pharmaceutical compositions of the disclosure comprise one or more fillers, a disintegrant, and a lubricant.

Fillers suitable for the pharmaceutical compositions disclosed herein are compatible with the other ingredients of the pharmaceutical compositions, i.e., they do not substantially reduce the solubility, the hardness, the chemical stability, the physical stability, or the biological activity of the pharmaceutical compositions. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., mannitol, lactose, sucrose, or the like), or any combination thereof. In some embodiments, the filler is microcrystalline cellulose.

In some embodiments, the pharmaceutical compositions comprise one or more fillers in an amount of at least 25 wt % (e.g., at least 27 wt % or at least 30 wt %) by weight of the pharmaceutical composition. For example, the pharmaceutical compositions comprise from 25 wt % to 40 wt % (e.g., from 25 wt % to 35 wt % or from 30 wt % to 33 wt %) of filler, by weight of the pharmaceutical composition. In another example, the pharmaceutical compositions comprise at least 25 wt % (e.g., at least 27 wt % or at least 30 wt %) of microcrystalline cellulose, for example Avicel PH102 or Avicel PH101, by weight of the pharmaceutical composition. In another example, the pharmaceutical compositions comprise from 25 wt % to 40 wt % (e.g., from 25 wt % to 35 wt % or from 30 wt % to 33 wt %) of microcrystalline cellulose, by weight of the pharmaceutical composition. In another example, the pharmaceutical compositions comprise about 31.7 wt % of microcrystalline cellulose, by weight of the pharmaceutical composition. In another example, the pharmaceutical compositions comprise about 32.6 wt % of microcrystalline cellulose, by weight of the pharmaceutical composition.

Disintegrants suitable for the pharmaceutical compositions disclosed herein can enhance the dispersal of the pharmaceutical compositions and are compatible with the other ingredients of the pharmaceutical compositions, i.e., they do not substantially reduce the chemical stability, the physical stability, the hardness, or the biological activity of the pharmaceutical compositions. Exemplary disintegrants include croscarmellose sodium, sodium starch glycolate, crospovidone or a combination thereof. In some embodiments, the disintegrant is croscarmellose sodium.

In some embodiments, the pharmaceutical compositions disclosed herein comprise disintegrant in an amount of 10 wt % or less (e.g., 8 wt % or less or 7 wt % or less) by weight of the pharmaceutical composition. For example, the pharmaceutical compositions comprise from 1 wt % to 10 wt % (e.g., from 2 wt % to 8 wt % or from 3 wt % to 7 wt %) of disintegrant, by weight of the pharmaceutical composition. In another example, the pharmaceutical compositions comprise 10 wt % or less (e.g., 8 wt % or less or 7 wt % or less) of croscarmellose sodium, by weight of the pharmaceutical composition. In another example, the pharmaceutical compositions comprise from 1 wt % to 10 wt % (e.g., from 2 wt % to 8 wt % or from 3 wt % to 7 wt %) of croscarmellose sodium, by weight of the pharmaceutical composition. In another example, the pharmaceutical compositions comprise about 5.8 wt % of croscarmellose sodium, by weight of the pharmaceutical composition. In another example, the pharmaceutical compositions comprise about 6.0 wt % of croscarmellose sodium, by weight of the pharmaceutical composition.

In some embodiments, the pharmaceutical compositions disclosed herein comprise a lubricant. A lubricant can prevent adhesion of a mixture component to a surface (e.g., a surface of a mixing bowl, a granulation roll, a compression die and/or punch). A lubricant can also reduce interparticle friction within the granulate and improve the compression and ejection of compressed pharmaceutical compositions from a granulator and/or die press. A suitable lubricant for the pharmaceutical compositions disclosed herein is compatible with the other ingredients of the pharmaceutical compositions, i.e., they do not substantially reduce the solubility, the hardness, or the biological activity of the pharmaceutical compositions. Exemplary lubricants include magnesium stearate, sodium stearyl fumarate, calcium stearate, zinc stearate, sodium stearate, stearic acid, aluminum stearate, leucine, glyceryl behenate, hydrogenated vegetable oil or any combination thereof. In some embodiments, the lubricant is magnesium stearate.

In one embodiment, the pharmaceutical compositions comprise a lubricant in an amount of 5 wt % or less (e.g., 4 wt % or less, 3 wt % or less, or 2 wt % or less) by weight of the pharmaceutical composition. For example, the pharmaceutical compositions comprise from 0.10 wt % to 5 wt % (e.g., from 0.5 wt % to 3 wt % or from 0.75 wt % to 2 wt %) of lubricant, by weight of the pharmaceutical composition. In another example, the pharmaceutical compositions comprise 5 wt % or less (e.g., 4 wt % or less, 3 wt % or less, or 2 wt % or less) of magnesium stearate, by weight of the pharmaceutical composition. In another example, the pharmaceutical compositions comprise from 0.10 wt % to 5 wt % (e.g., from 0.5 wt % to 3 wt % or from 0.75 wt % to 2 wt %) of magnesium stearate, by weight of the pharmaceutical composition. In another example, the pharmaceutical compositions comprise about 1.0 wt % of magnesium stearate, by weight of the pharmaceutical composition.

In some embodiments, the pharmaceutical compositions disclosed herein are tablets. In some embodiments, the tablets comprise a film coat. In some embodiments, the film coat is Opadry 20A100021.

In some embodiments, the tablets disclosed herein comprise:

| Component | mg per tablet |
| --- | --- |
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |

In some embodiments, the tablets disclosed herein comprise:

| Component | mg per tablet |
| --- | --- |
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| Microcrystalline cellulose | 70-170 mg |

In some embodiments, the tablets disclosed herein comprise:

| Component | mg per tablet |
| --- | --- |
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| Croscarmellose sodium | 10-40 mg |

In some embodiments, the tablets disclosed herein comprise:

| Component | mg per tablet |
| --- | --- |
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| Croscarmellose sodium | 10-40 mg |
| Microcrystalline cellulose | 70-170 mg |

In some embodiments, the tablets disclosed herein comprise:

| Component | mg per tablet |
| --- | --- |
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| microcrystalline cellulose | 55.1 |
| croscarmellose sodium | 22.8 |
| extragranular: | |
| microcrystalline cellulose | 68.9 |
| magnesium stearate | 3.8 |

In some embodiments, the tablets disclosed herein comprise:

| Component | mg per tablet |
|---|---|
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| microcrystalline cellulose | 55.1 |
| croscarmellose sodium | 22.8 |
| extragranular: | |
| microcrystalline cellulose | 68.9 |
| magnesium stearate | 3.8 |
| coating: | |
| film coat | 11.4 |

In some embodiments, the tablets disclosed herein comprise:

| Component | Composition (% w/w) (based on the total weight of the tablet) |
|---|---|
| intragranular: | |
| solid dispersion containing 80 wt % Compound I, 19.5 wt % hypromellose acetate succinate, and 0.5 wt % sodium lauryl sulfate | 41.1 |
| Compound II, calcium salt hydrate Form D | 2.8 |
| solid dispersion containing 80 wt % Compound III, 20 wt % hypromellose | 16.4 |
| microcrystalline cellulose | 14.5 |
| croscarmellose sodium | 6.0 |
| extragranular: | |
| microcrystalline cellulose | 18.1 |
| magnesium stearate | 1.0 |

In some embodiments, the tablets disclosed herein comprise:

| Component | Composition (% w/w) (based on the total weight of the tablet) |
|---|---|
| intragranular: | |
| solid dispersion containing 80 wt % Compound I, 19.5 wt % hypromellose acetate succinate, and 0.5 wt % sodium lauryl sulfate | 39.9 |
| Compound II, calcium salt hydrate Form D | 2.7 |
| solid dispersion containing 80 wt % Compound III, 20 wt % hypromellose | 16.0 |
| microcrystalline cellulose | 14.1 |
| croscarmellose sodium | 5.8 |
| extragranular: | |
| microcrystalline cellulose | 17.6 |
| magnesium stearate | 1.0 |
| coating: | |
| film coat | 2.9 |

In some embodiments, the tablets disclosed herein comprise:

| Component | mg per tablet |
|---|---|
| intragranular: | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| microcrystalline cellulose | 55.1 |
| croscarmellose sodium | 22.8 |
| extragranular: | |
| microcrystalline cellulose | 69.9 |
| magnesium stearate | 2.9 |

In some embodiments, the tablets disclosed herein comprise:

| Component | Composition (% w/w) (based on the total weight of the tablet) |
|---|---|
| intragranular: | |
| solid dispersion containing 80 wt % Compound I, 19.5 wt % hypromellose acetate succinate, and 0.5 wt % sodium lauryl sulfate | 41.1 |
| Compound II, calcium salt hydrate Form D | 2.8 |
| solid dispersion containing 80 wt % Compound III, 20 wt % hypromellose | 16.5 |
| microcrystalline cellulose | 14.5 |
| croscarmellose sodium | 6.0 |
| extragranular: | |
| microcrystalline cellulose | 18.4 |
| magnesium stearate | 0.75 |

In some embodiments, the tablets disclosed herein comprise:

| Component | mg per tablet |
|---|---|
| core tablet (combined intragranular and extragranular): | |
| solid dispersion containing 80 wt % Compound I, 19.5 wt % hypromellose acetate succinate, and 0.5 wt % sodium lauryl sulfate | 156.3 |
| Compound II, calcium salt hydrate Form D | 10.6 |
| solid dispersion containing 80 wt % Compound III, 20 wt % hypromellose | 62.5 |
| microcrystalline cellulose | 124.5 |
| croscarmellose sodium | 22.8 |
| magnesium stearate | 3.8 |
| coating: | |
| film coat | 15.9 |

In some embodiments, the tablets disclosed herein comprise:

| Component | Composition (% w/w) (based on the total weight of the tablet) |
| --- | --- |
| core tablet (combined intragranular and extragranular): | |
| solid dispersion containing 80 wt % Compound I, 19.5 wt % hypromellose acetate succinate, and 0.5 wt % sodium lauryl sulfate | 39.4 |
| Compound II, calcium salt hydrate Form D | 2.7 |
| solid dispersion containing 80 wt % Compound III, 20 wt % hypromellose | 15.8 |
| microcrystalline cellulose | 31.4 |
| croscarmellose sodium | 5.8 |
| magnesium stearate | 1.0 |
| coating: | |
| film coat | 4.0 |

General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution, respectively. All proton and carbon spectra were acquired with temperature control at 30° C. using standard, previously published pulse sequences and routine processing parameters. Final purity of compounds was determined by reversed phase UPLC using an Acquity UPLC BEH C18 column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were obtained using a single quadrupole mass spectrometer with a mass accuracy of 0.1 Da and a minimum resolution of 1000 amu across the detection range using electrospray ionization (ESI) using the hydrogen ion (H$^+$). Optical purity of methyl (2S)-2,4-dimethyl-4-nitro-pentanoate was determined using chiral gas chromatography (GC) analysis on an Agilent 7890A/MSD 5975C instrument, using a Restek Rt-rβDEXcst (30 m×0.25 mm×0.25 um_df) column, with a 2.0 mL/min flow rate (H$_2$ carrier gas), at an injection temperature of 220° C. and an oven temperature of 120° C., 15 minutes. Purity of Compound I was determined by reverse phase HPLC using an Poroshell 120 EC-C8 column (4.6×150 mm, 2.7 μm particle, and a dual gradient run from 30-95% mobile phase B over 40 minutes. Mobile phase A=5 mM Ammonium Acetate pH 4.50 and Mobile phase B=Acetonitrile. Flow rate=1.0 mL/min, injection volume=5 μL, 254 nm, and column temperature=30° C.

Compounds I, II, and III can be prepared by any suitable method in the art. Methods of making Compound I can be found in WO 2019/109021 and U.S. Pat. No. 9,512,079; methods of making Compound II and its pharmaceutically acceptable salts thereof are disclosed in WO 2019/161078 and PCT/US2020/046116; methods of making Compound III and pharmaceutically acceptable salts thereof are disclosed in WO 2011/119984 and WO 2011/133751, all of which are incorporated herein by reference.

Example 1: Synthesis of N-(2-(tert-butyl)-5-hydroxy-4-(2-(methyl-d3)propan-2-yl-1,1,1,3,3,3-d6) phenyl)-4-oxo-1,4-dihydroquinoline-3-carboxamide. (Compound I)

The overall scheme of the synthesis of (2) (Compound I) is shown below, followed by the procedure for the synthesis of each intermediate.

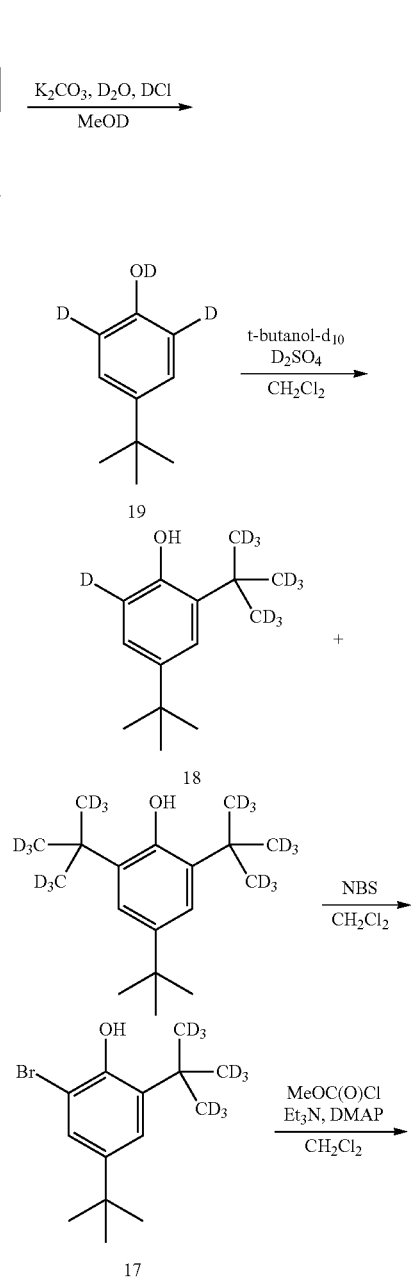

-continued

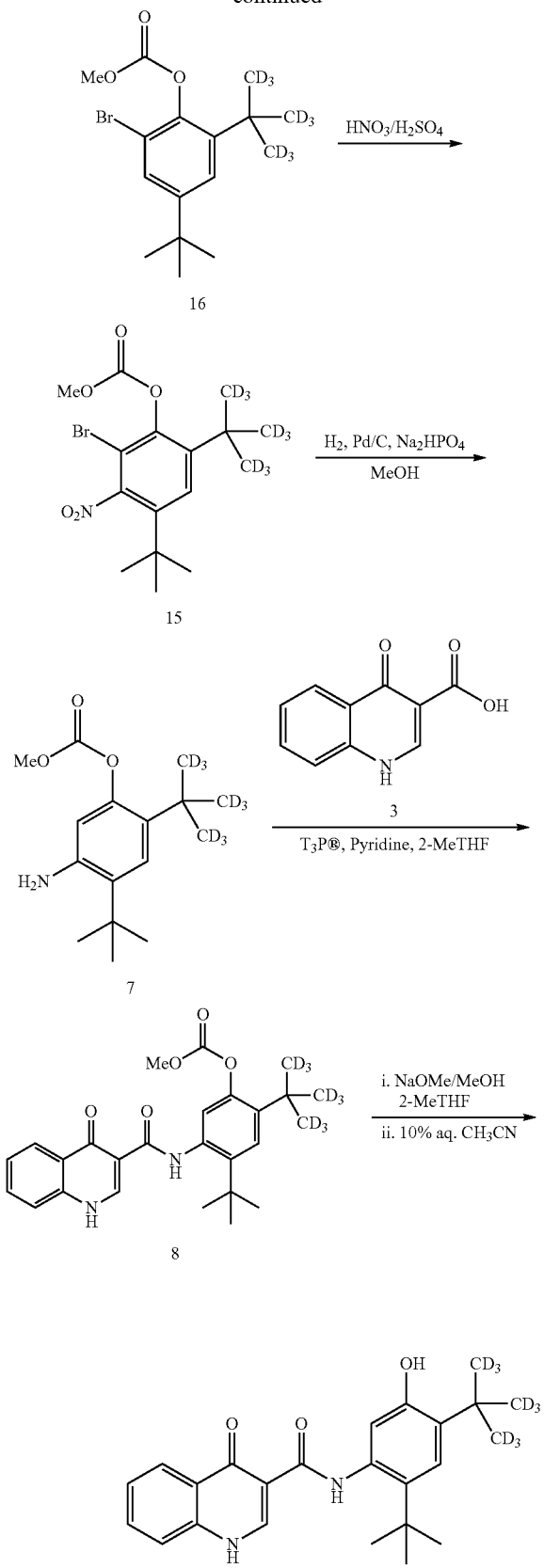

Procedure for the Synthesis of 4-(tert-butyl)phen-2,6-d2-ol-d (19)

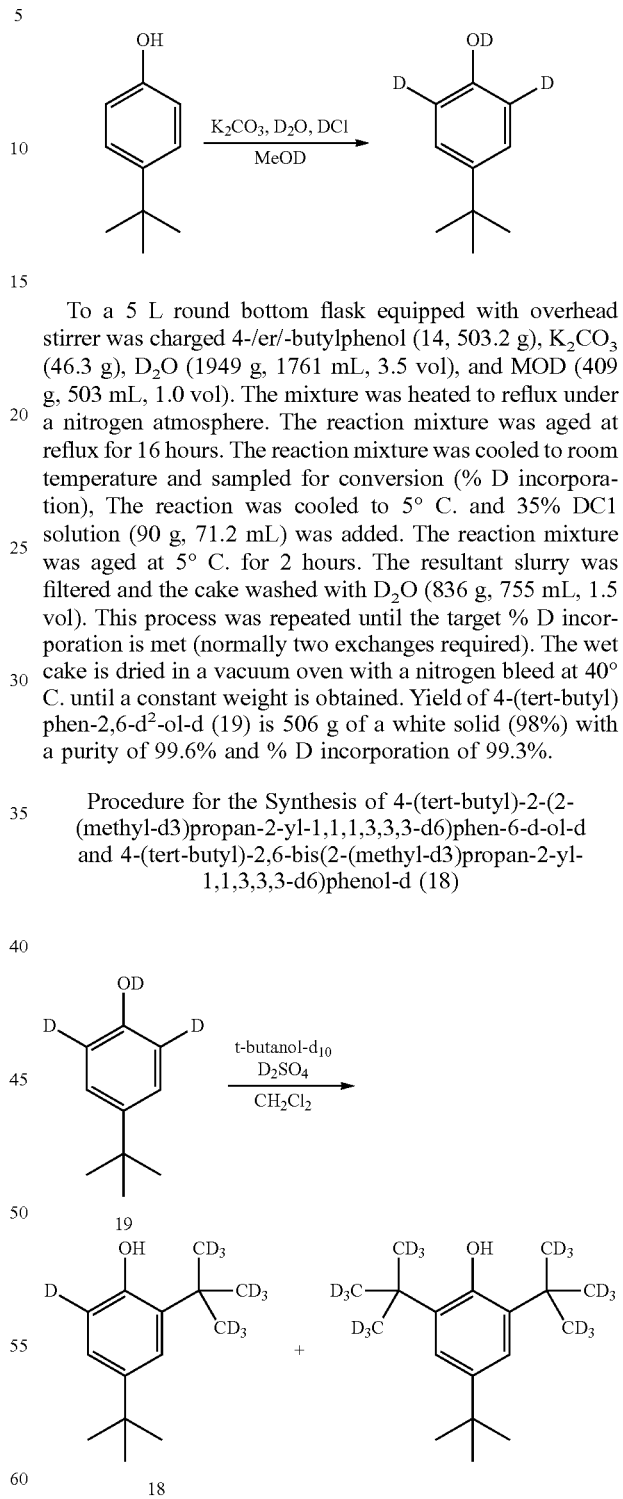

To a 5 L round bottom flask equipped with overhead stirrer was charged 4-/er/-butylphenol (14, 503.2 g), $K_2CO_3$ (46.3 g), $D_2O$ (1949 g, 1761 mL, 3.5 vol), and MOD (409 g, 503 mL, 1.0 vol). The mixture was heated to reflux under a nitrogen atmosphere. The reaction mixture was aged at reflux for 16 hours. The reaction mixture was cooled to room temperature and sampled for conversion (% D incorporation), The reaction was cooled to 5° C. and 35% DCl solution (90 g, 71.2 mL) was added. The reaction mixture was aged at 5° C. for 2 hours. The resultant slurry was filtered and the cake washed with $D_2O$ (836 g, 755 mL, 1.5 vol). This process was repeated until the target % D incorporation is met (normally two exchanges required). The wet cake is dried in a vacuum oven with a nitrogen bleed at 40° C. until a constant weight is obtained. Yield of 4-(tert-butyl)phen-2,6-$d^2$-ol-d (19) is 506 g of a white solid (98%) with a purity of 99.6% and % D incorporation of 99.3%.

Procedure for the Synthesis of 4-(tert-butyl)-2-(2-(methyl-d3)propan-2-yl-1,1,1,3,3,3-d6)phen-6-d-ol-d and 4-(tert-butyl)-2,6-bis(2-(methyl-d3)propan-2-yl-1,1,3,3,3-d6)phenol-d (18)

4-(tert-butyl)phen-2,6-$d^2$-ol-d (19) (101.8 g, 0.66 mol, 1.0 equiv.) was dissolved in $CH_2Cl_2$ (400 mL) in a 2 L reactor. /er/-Butanol-£¾o (43.0 g, 0.51 mol, 0.77 equiv.) was dissolved in $CH_2Cl_2$ (100 mL) in a 250 mL flask. The solution of tert-butanol-r/was charged to the 2 L reactor at room temperature. The reaction mixture was cooled to −5° C. $D_2SO_4$ (51.1 g, 0.51 mol, 0.77 equiv.) was charged dropwise via an addition funnel while maintaining a temperature range of −4 to −2° C. The reaction mixture was stirred at −2° C. for 3-4 hours. Upon complete conversion the reaction was quenched by adding water (28 mL) and warmed to 18-20° C. The bottom aqueous layer was drained and discarded. The $CH_2Cl_2$ layer was treated with sat. aq. NaHCCh solution (approximately 200 mL), adjusting the pH to 6-8. NaCl (sat.) solution (400 mL) was charged to the mixture. The resulting solution was stirred for 5 min, and settled for 5 min. The lower $CH_2Cl_2$ layer was drained into a 1 L flask. The aqueous layer was discarded. The $CH_2Cl_2$ solution was concentrated to minimal volume and n-heptane (200 mL) was charged. The solution was concentrated to minimal volume and nheptane charged to a final volume of 800 mL. 0.5 N NaOH solution 600 mL (6 vol) was charged to the reactor and the resulting mixture was stirred for 5 mm, and settled for at least 5 min. The aqueous layer was drained and discarded. 1.0 N NaOH solution 300 mL (3 vol) was charged to the reactor and the resulting mixture was stirred for 5 min. and settled for at least 5 min. The aqueous layer was drained and discarded. 1.0 N NaOH solution 300 mL (3 vol) was charged to the reactor and the resulting mixture was stirred for 5 min, and settled for at least 5 min. The aqueous layer was drained and discarded. The remaining n-heptane solution was concentrated to dryness to afford the desired product, 4-(tert-butyl)-2-(2-(methyl-$d^3$)propan-2-yl-1,1,1,3,3,3-$d^6$)phen-6-d-ol-d (18) as a clear oil, 104.5 g, which was carried forward into the next step without further purification.

Procedure for the Synthesis of 2-bromo-4-(tert-butyl)-6-(2-(methyl-d3)propan-2-yl-1,1,3,3,3-d6) phenol (17)

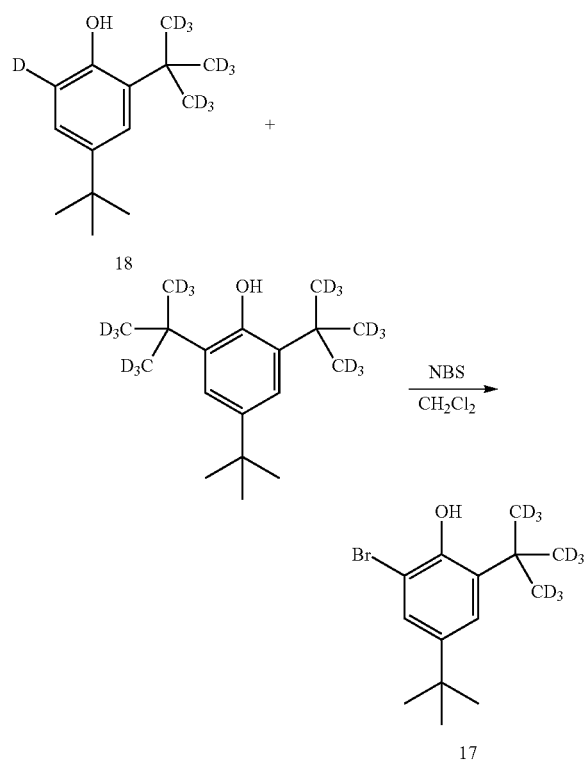

4-(tert-butyl)-2-(2-(methyl-$d^3$)propan-2-yl-1,1,1,3,3,3-$d^6$)phen-6-d-ol-d (18) (100 g, 0.462 mol, 1.0 equiv.) was dissolved in CH2Cl2 (800 mL, 7 vol) in a 2 L reactor and the solution was stirred. The batch was cooled down to 0±3° C. To the batch was charged portion-wise N-bromosuccinimide (84.4 g, 0.462 mol, 1.0 equiv) over 30 min. The batch was stirred at 0±2° C. for at least 30 minutes. The batch was then heated to 20±2° C. over a period of 2 hours and stirred at 20±2° C. for at least 12 hours. Upon complete conversion, sat. aq. NaHCCh solution (500 mL, 5 vol) was charged and the batch stirred for at least 10 minutes. The agitation was stopped to allow the phases to separate for at least 5 minutes and the CH2Cl2 layer was drained, followed by removal of the aqueous layer. The CTLCh layer was charged back to the vessel. To the batch was charged sat. aq. NaHCCh bicarbonate solution (500 mL, 5 vol), and the batch was stirred for at least 10 minutes. The agitation was stopped to allow the phases to separate for at least 5 minutes and the $CH_2Cl_2$ layer was drained, followed by removal of the aqueous layer. The $CH_2Cl_2$ layer was charged back to the vessel and diluted with an additional CH2Cl2 (300 mL, 3 vol). The batch was distilled (removal of 30) mL) and checked by KF to achieve dryness. The resulting clear yellow solution of 17 was carried forward into the next step without further purification.

Procedure for the Synthesis of 2-bromo-4-(tert-butyl)-6-(2-(methyl-d3)propan-2-yl-1,1,1,3,3,3-d6) phenyl methyl carbonate (16)

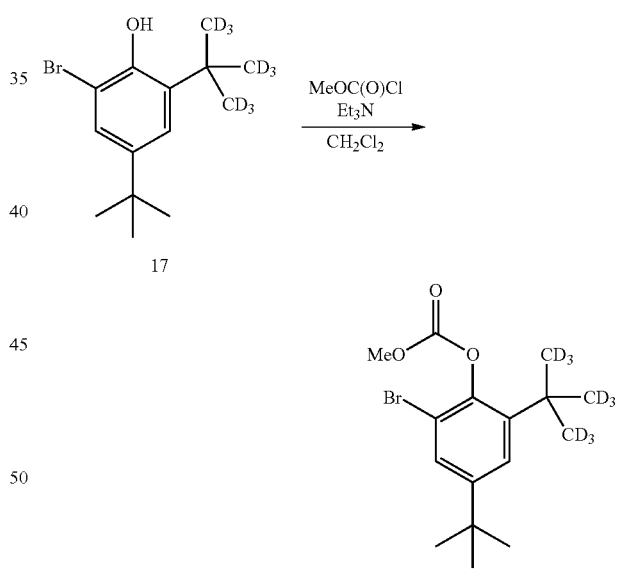

To a clean reactor was charged the $CH_2Cl_2$ solution of 4-(tert-butyl)-2-(2-(methyl-d3)propan-2-yl-1,1,1,3,3,3-d6) phen-6-d-ol-d (17) (136 g, 0.462 mol, 1.0 equiv.) followed by additional $CH_2Cl_2$ (130 mL, 1 vol), and this solution was stirred. To the batch was charged 4-(dimethylamino)pyridine (2.8 g, 0.023 mol, 0.05 equiv) and triethylamine (70.1 g, 0.693 mol, 1.5 equiv). The batch was cooled to 0±3° C. To the batch was charged drop-wise methyl chloroformate (48.0 g, 0.508 mol, 1.1 equiv) over 40 minutes while maintaining a batch temperature <5° C. The batch was stirred at 3±2° C. for at least 30 minutes, and then warmed to 20±2° C. over a period of 1 hour. Upon complete conversion, 1 N HCl (400 mL, 3 vol) was charged. The batch was stirred for at least 10 minutes, and then the layers were allowed to separate for at least 5 minutes. The lower organic layer was drained followed by the aqueous layer (1st aqueous layer). The organic layer was charged back to the reactor, along with 1 N HCl solution (400 mL, 3 vol). The batch was stirred for at least 10 minutes, and then the layers were allowed to separate for at least 5 minutes. The lower organic layer was drained. The first aqueous layer was charged to the reactor, along with $CH_2Cl_2$ (300 mL, 2.2 vol). The batch was stirred for at least 10 minutes, and then the layers were allowed to separate for at least 5 minutes. The lower organic layer was drained and combined with the 1 organic layer, followed by removal of the aqueous layer. Charge the vessel with the contents of both organic layers. The reactor was charged with water (500 mL, 3.7 vol). The batch was stirred for at least 10 minutes, and then the layers were allowed to separate for at least 5 minutes. The lower organic layer was drained, followed by the aqueous layer. The organic layer was charged back to the reactor, along $CH_2Cl_2$ (400 mL, 3 vol). The batch was distilled to remove 800 mL and checked by KF to ensure dryness. The resulting clear yellow solution of 16 was telescoped into the next step without further purification.

were separated and the upper aqueous layer was extracted with $CH_2Cl_2$ (2.8 vol). After separating the layers, the organic layers were combined, returned to the reactor, and washed with sodium bicarbonate (7.4% w/w, 6.8 vol). After separating the layers, the organic layer was returned to the reactor and washed with sodium chloride (23% w/w, 3.8 vol). After separating the layers, the organic layer was returned to the reactor and concentrated to minimal volume. Methanol (1.2 vol) was charged, followed by concentration to minimal volume. Methanol (1.2 vol) was charged, followed by concentration to minimal volume. Methanol (1.7 vol) was charged, and the slurry was heated to reflux for 30 min and then cooled slowly over 4 hours to 5° C. The solid product (15) was filtered and the cake washed with cold methanol (1.0 vol). The solid 2-bromo-4-(tert-butyl)-6-(2-(methyl-d3)propan-2-yl-1,1,1,3,3,3-d6)-3-nitrophenyl methyl carbonate (15) was dried under vacuum at 40-50° C. to yield an off-white solid, 99.9% purity and 99% D incorporation.

Procedure for the Synthesis of 5-amino-4-(tert-butyl)-2-(2-(methyl-d3)propan-2-yl-1,1,1,3,3,3-d6) phenyl methyl carbonate (7)

Procedure for the Synthesis of 2-bromo-4-(tert-butyl)-6-(2-(methyl-d3)propan-2-yl-1,1,1,3,3,3-d6)-3-nitrophenyl methyl carbonate (15)

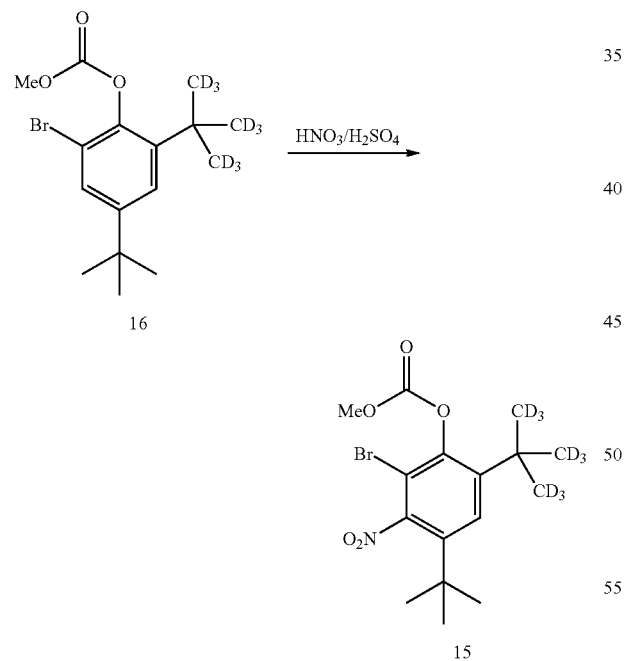

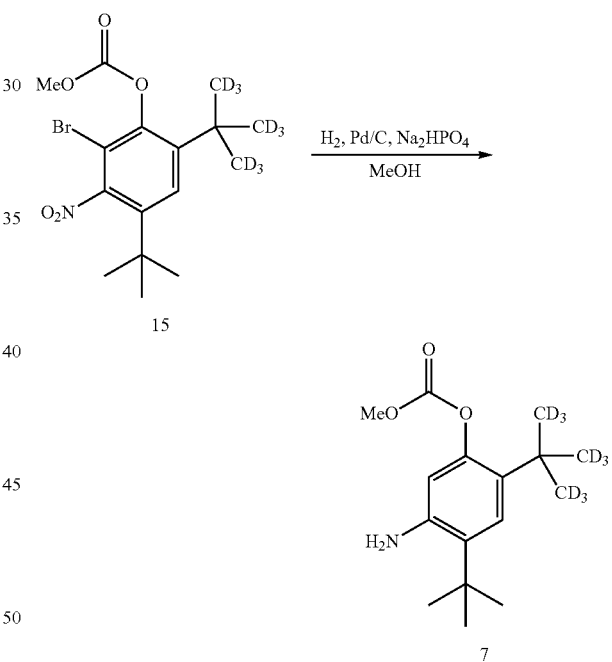

To a reactor was charged 2-bromo-4-(tert-butyl)-6-(2-(methyl-d3)propan-2-yl-1,1,1,3,3,3-d6)phenyl methyl carbonate (16) and then the solution was cooled to 0° C. Sulfuric acid (4.9 equiv) and nitric acid (100%, 2.0 equiv) was charged while maintaining a temperature of not more than 5° C. The reaction was stirred at 0° C. for 2 hours until complete conversion. The reaction was then quenched with water (8.8 vol) and diluted with $CH_2Cl_2$ (1.7 vol). The layers Charge 5 wt % (50-65 wt % wet, JM Type 37) of 5% Pd/C to a reactor. Charge (4.0 vol) Methanol Close the system. Purge with $N2_{(g)}$ at 2.0 Bar. Activate with $H2_{(g)}$ at 2.0 Bar Charge the vessel to 2.0 Bar with $H2_{(g)}$ at 25° C.+/−5° C. Stir for not less than 2 hours while maintaining a temperature of 25° C.+/−5° C. Vent and purge with $N2_{(g)}$ at 2.0 Bar. Charge compound 15 (1.0 eq) to a reactor, together with $Na_2HPO_4$ (2.3 eq). Charge (11.0 vol) Methanol. Close the system. Purge with $N2_{(g)}$ at 2.0 Bar Activate with $H2_{(g)}$ at 2.0 Bar. Charge the vessel to 2.0 Bar with $H2_{(g)}$ at 25° C.+/−5° C. Stir for about 24 hours while maintaining a reaction temperature of 25° C.+/−5° C. Upon complete conversion, dilute reaction mixture by adding 7.7 vol of MeOH. Heat reaction mixture to 35.0° C.+/−5° C. Filter off catalyst and Na2HPO₄. Wash the reactor and filter cake with Methanol (4.0 vol), and filter, combining with the initial filtrate. Check Pd content and if needed perform resin treatment (resin treatment is: Charge SPM-32 resin (5 wt %). Stir the resin treated solution for not less than 3 hours at 35.0° C.+/−5° C. Filter off resin.

Wash the reactor and filter cake with Methanol (2.0 vol), and filter, combining with the initial filtrate). Charge Norit CASP active carbon (3 wt %). Stir for not less than 3 hours at 35.0° C.+/−5° C. Filter off active carbon. Wash the reactor and filter cake with Methanol (2.0 vol), and filter, combining with the initial filtrate. Distill under vacuum at not more than 50° C. to 8.0 vol. Charge water (2.0 vol) while maintaining a temperature of 45° C.+/−5° C. Cool the resultant slurry to 0° C.+/−5° C. over 2 hours. Hold and stir the slurry at 0° C.+/−5° C. for not less than 1 hour. Filter and wash the cake with 2.0 volumes Methanol/Water (8:2) at 0° C.+/−5° C. Dry 5-amino-4-(tert-butyl)-2-(2-(methyl-d3)propan-2-yI-1,/,1,3,3,3-d6)phenyl methyl carbonate (7) under vacuum at not more than 40° C. to give a yield of a white solid. >99.5% purity.

Procedure for the Synthesis of 4-(tert-butyl)-2-(2-(methyl-d3)propan-2-yl-1,1,1,3,3,3-d6)-5-(4-oxo-1,4-dihydroquinidine-3-carboxamido)phenyl methyl carbonate (8)

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2) (Compound 1)

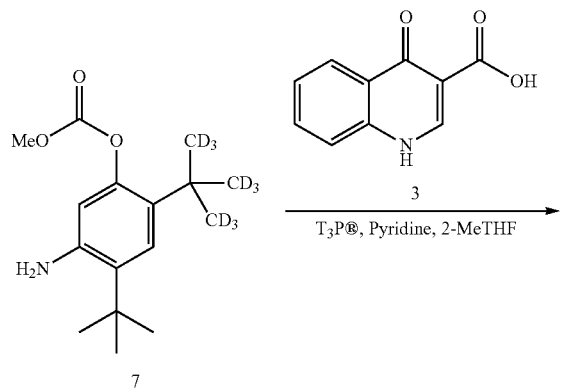

The procedure for the conversion of compound 8 into compound 2 may be performed according to the analogous procedure for the synthesis of compound 1.

Example 2: Synthesis of 5-amino-4-(tert-butyl)-2-(2-(methyl-d3)propan-2-yl-1,1,1,3,3,3-d6)phenyl methyl carbonate (7)

An alternative overall scheme of the synthesis of compound 7 is shown below, followed by the procedure for the synthesis of each synthetic intermediate.

The procedure for the conversion of compound 7 into compound 8 may be performed according to the analogous procedure for compound 5.

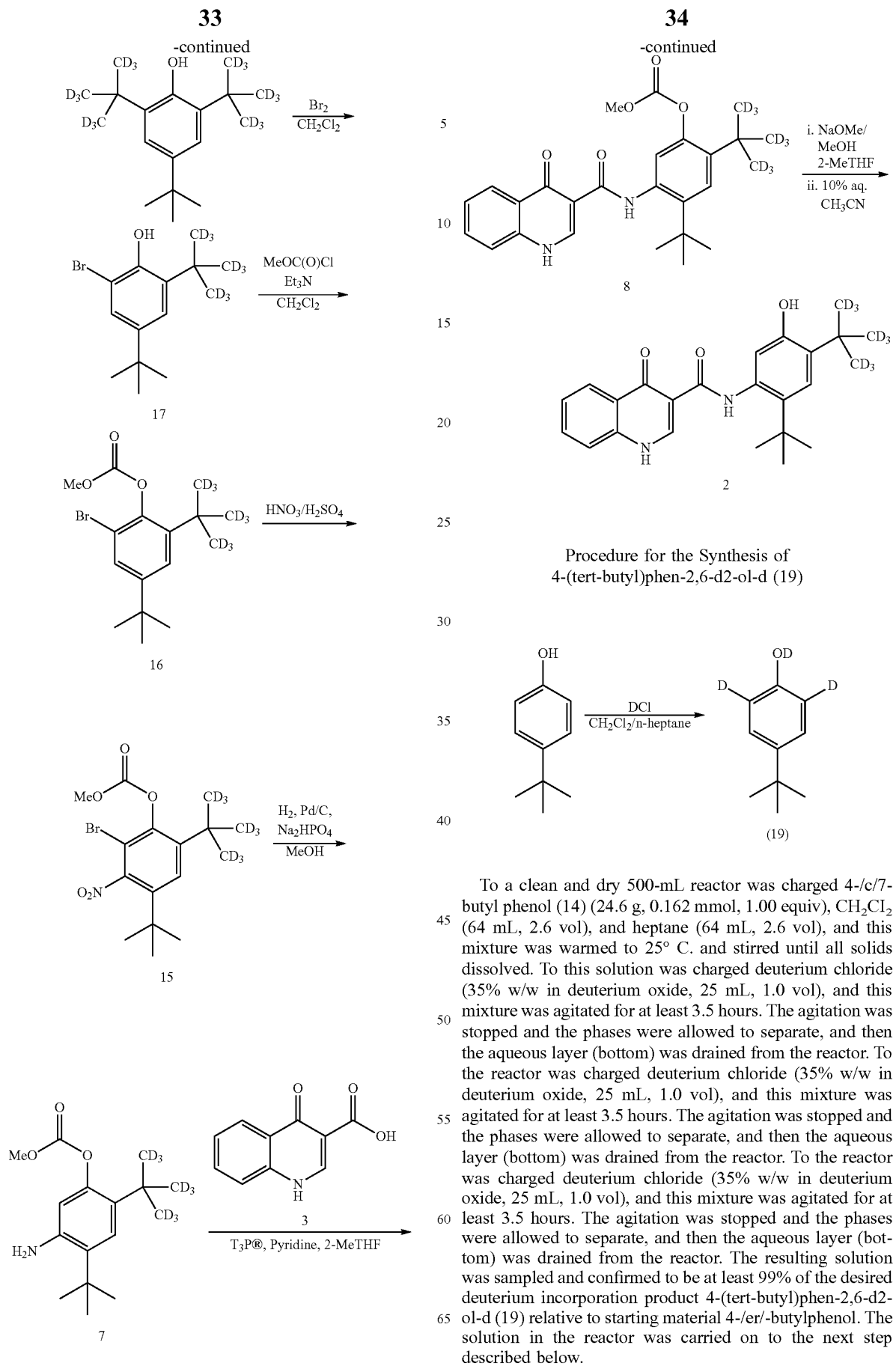

Procedure for the Synthesis of 4-(tert-butyl)phen-2,6-d2-ol-d (19)

To a clean and dry 500-mL reactor was charged 4-/c/7-butyl phenol (14) (24.6 g, 0.162 mmol, 1.00 equiv), CH$_2$Cl$_2$ (64 mL, 2.6 vol), and heptane (64 mL, 2.6 vol), and this mixture was warmed to 25° C. and stirred until all solids dissolved. To this solution was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. To the reactor was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. To the reactor was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. The resulting solution was sampled and confirmed to be at least 99% of the desired deuterium incorporation product 4-(tert-butyl)phen-2,6-d2-ol-d (19) relative to starting material 4-/er/-butylphenol. The solution in the reactor was carried on to the next step described below.

Procedure for the Synthesis of 4-(tert-butyl)-2-(2-(methyl-d3)propan-2-yl-1,1,1,3,3,3-d6)phen-6-d-ol (18)

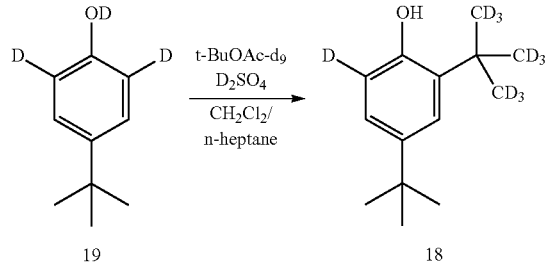

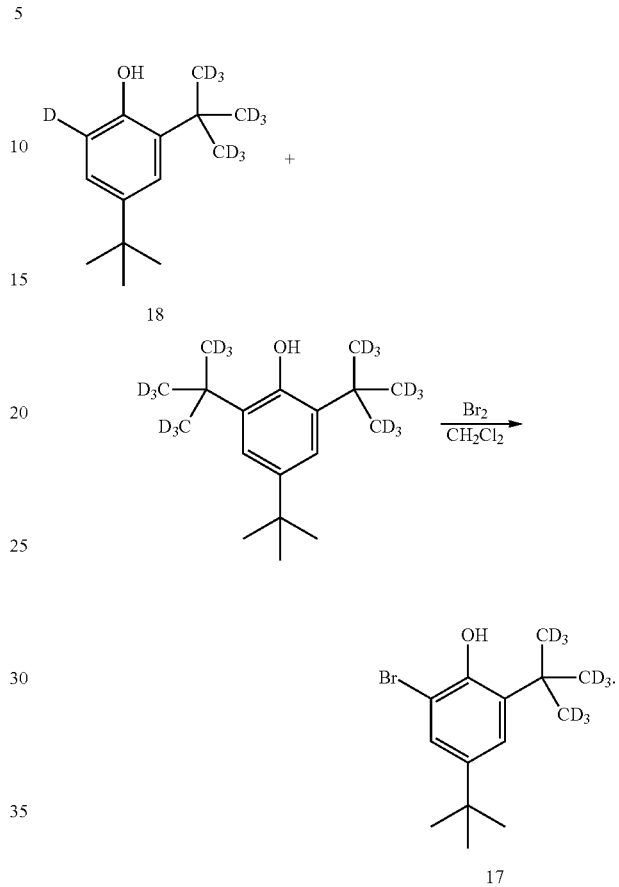

Procedure for the Synthesis of 2-bromo-4-(tert-butyl)-6-(2-(methyl-d3)propan-2-yl-1,1,1,3,3,3-d6) phenol (17)

To the methylene chloride solution containing the reaction mixture of 4-(tert-butyl)phen-2,6-d2-ol-d (19) was charged $CH_2Cl_2$ (125 mL, 5 Vol). Approximately 125 mL of the reaction solution was distilled from the reactor using a distillation head and heating the reactor to 60° C. To the reactor was charged $CH_2Cl_2$ (125 mL, 5 vol). Approximately 100 mL of the reaction solution was then distilled from the reactor, and at this time the solution was sampled to confirm water content (KF) was less than 300 ppm and determine the $CH_2Cl_2$ and heptane content. After measuring the batch volume, $CH_2Cl_2$ (8 mL, 0.24 vol) was charged to adjust the total $CH_2Cl_2$ content to 3 vol and heptane (68 mL, 2.8 vol) was charged to adjust the heptane content to 4.5 vol. To the solution was charged/cvv-butyl acetate-dg (30.2 g, 1.46 equiv), and the resulting solution was cooled to 0° C. To the solution was charged sulfuric acid-J2 (8.12 g, 0.49 equiv) over at least 15 min. and the solution was agitated for 2 hours while maintaining the temperature at 0-5° C. After this time, the temperature was set to ramp up to 20° C. over two hours and the solution was agitated for another 14 hours. The solution was sampled to confirm 4-/c77-butyl phenol (14) or 4-(tert-butyl)phen-2,6-d2-ol-d (19) were present at less than 3%. To the reactor was charged $CH_2Cl_2$ (58 mL, 2.4 vol) and heptane (90 mL, 3.7 vol), and the solution was cooled to 0-5° C. before charging water (125 mL, 5 vol). The mixture was agitated for 15 min before agitation was stopped and the phases were allowed to separate. After the aqueous phase (bottom) was drained from the reactor, 0.5 N aqueous NaOH (125 mL, 5 vol) was charged and the temperature was adjusted to 20° C. The mixture was agitated for 20 min before agitation was stopped and the phases were allowed to separate. The organic phase (top) was sampled to confirm 4-tert-butylphenol (14) or 4-(tert-butyl)phen-2,6-d2-ol-d (18) were present at less than 0.5%. The aqueous phase (bottom) was drained from the reactor. The solution in the reactor was carried on to the next step described below.

After the agitated solution of the alkylation reaction to produce 4-(tert-butyl)-2-(2-(methyl-d3)propan-2-yl-1,1,1,3,3,3-d6)phen-6-d-ol-d (18) was brought to 0-5° C., bromine (38.4 g, 1.45 equiv) was charged over at least 1 hour, maintaining the temperature below 5° C. The solution was sampled to confirm 4-(tert-butyl)-2-(2-(methyl-d3)propan-2-yl-1,1,1,3,3,3-d6)phen-6-d-ol was present at less than 1%. To the solution was charged sodium metabisulfite (20% w/w aqueous solution, 147 g, 0.95 equiv) over at least 1 hour, maintaining the temperature below 10° C. After adjusting the temperature to 20° C. the mixture was agitated for another 1 hour. Agitation was stopped and the phases were allowed to separate. The aqueous phase (bottom) was drained from the reactor, and water (125 mL, 5 vol) was charged to the reactor. The mixture was agitated for 15 min before stopping agitation and allowing the phases to separate. The aqueous phase (bottom) was drained from the reactor. The solution of 17 in the reactor was carried on to the next step described below.

Surprisingly, this bromination reaction significantly improved the selectivity of the nitration reaction. Another unexpected advantage to this process was that bromination converted the mixture of compound 18 and 4-(tert-butyl)-2,6-bis(2-(methyl-d3)propan-2-yl-1,1,1,3,3,3-d6)phenol to the same desired product (17). This significantly improved the overall yield.

Procedure for the Synthesis of 2-bromo-4-(tert-butyl)-6-(2-(methyl-d3)propan-2-yl-1,1,1,3,3,3-d6) phenyl methyl carbonate (16)

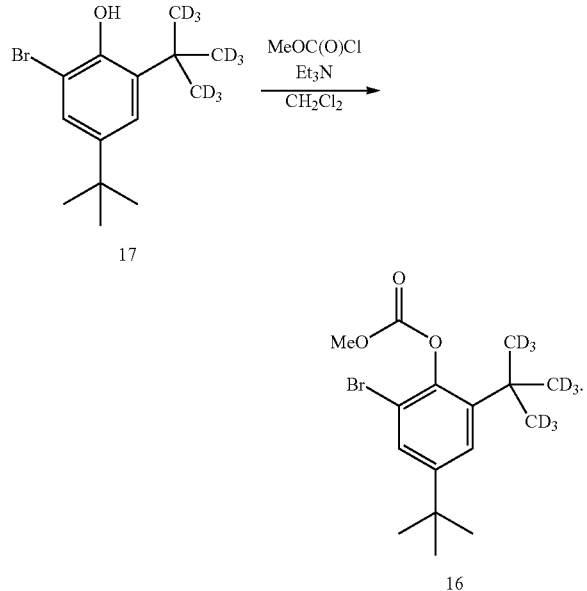

Procedure for the Synthesis of 2-bromo-4-(tert-buty)-6-(2-(methyl-d3)propan-2-yl-1,1,1,3,3,3-d6)-3-nitrophenyl methyl carbonate (15)

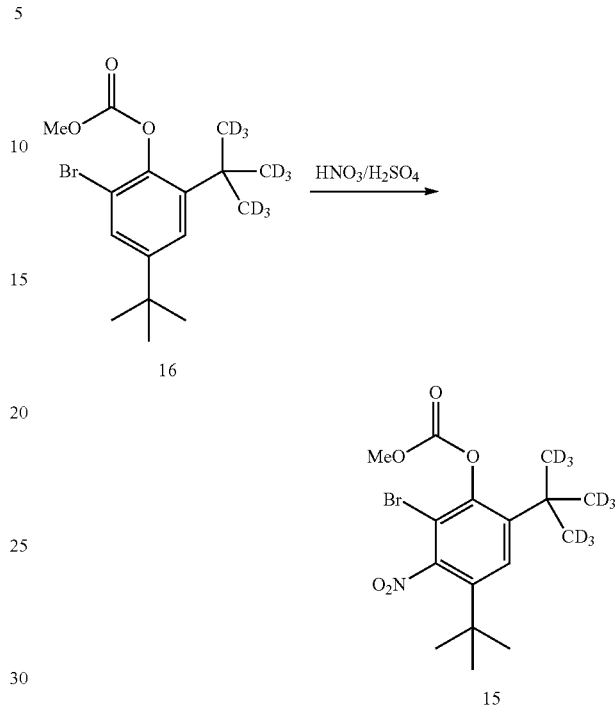

To the solution of the bromination reaction to produce 2-bromo-4-(tert-butyl)-6-(2-(methyl-d3)propan-2-yl-1,1,1,3,3,3-d6)phenol (17) was charged $CH_2Cl_2$ (125 mL, 5 vol). Approximately 125 mL of the reaction solution was distilled from the reactor using a distillation head and heating the reactor to 60° C. To the reactor was charge $CH_2Cl_2$ (125 mL, 5 vol). Approximately 125 mL of the reaction solution was distilled from the reactor. To the reactor was charged $CH_2Cl_2$ (125 mL, 5 vol). Approximately 125 mL of the reaction solution was then distilled from the reactor, and at this time the solution was sampled to confirm water content (KF) was less than 300 ppm and determine the CH2Cl2 and heptane content. After measuring the batch volume, CFLCh was charged to adjust the total $CH_2Cl_2$ content to 5.3 vol and heptane was charged to adjust the heptane content to 8 vol. To the solution was charged triethylamine (31.7 g, 1.91 equiv), and the solution was cooled to 0-5° C. To the solution was charged methyl chloroformate (24.1 g, 1.56 equiv) over at least 1 hour, maintaining the temperature below 10° C. The solution was agitated for 1 hour, and a sample of the solution was taken to confirm 2-bromo-4-(tert-butyl)-6-(2-(methyl-d3)propan-2-yl-1,1,1,3,3,3-d6)phenol (17) was present at less than 1%. To the solution was charged 1 N aqueous hydrochloric acid (125 mL, 0.76 equiv) over at least 30 min, maintaining the temperature below 10° C. The temperature was then adjusted to 20° C., and agitation was stopped and the phases were allowed to separate. After the aqueous phase (bottom) was drained from the reactor, water (125 mL. 5 vol) was charged to the reactor. The mixture was agitated for 15 min before agitation was stopped and the phases were allowed to separate. After the aqueous phase (bottom) was drained from the reactor, water (125 mL, 5 vol) was charged to the reactor. The mixture was agitated for 15 min before agitation was stopped and the phases were allowed to separate. The aqueous phase (bottom) was drained from the reactor. The solution of (16) in the reactor was carried on to the next step described below.

To the solution of the protection reaction to produce 2-bromo-4-(tert-butyl)-6-(2-(methyl-d3)propan-2-yl-1,1,1,3,3,3-d6)phenyl methyl carbonate (16) was charged $CH_2Cl_2$ (125 mL, 5 vol). Approximately 125 mL of the reaction solution was distilled from the reactor using a distillation head and heating the reactor to 60° C. To the reactor was charged $CH_2Cl_2$ chloride (125 mL, 5 vol). Approximately 125 mL of the reaction solution was distilled from the reactor. To the reactor was charged $CH_2Cl_2$ (125 mL, 5 vol). To the reactor was charged $CH_2Cl_2$ (125 mL, 5 vol). Approximately 125 mL of the reaction solution was distilled from the reactor. Approximately 125 mL of the reaction solution was then distilled from the reactor, and at this time the solution was sampled to confirm water content (KF) was less than 300 ppm and determine the $CH_2Cl_2$ and heptane content. After measuring the batch volume, $CH_2Cl_2$ was charged to adjust the total $CH_2Cl_2$ content to 6 vol and heptane was charged to adjust the heptane content to 9 vol. After cooling the solution to 0-5° C., sulfuric acid (172 g, 10.3 equiv) was charged over at least 30 min, maintaining the temperature below 5° C. To the mixture was charged nitric acid (70% w/w, 19.1 g, 1.31 equiv) over at least 30 min, maintaining the temperature below 10° C. After agitating the mixture for 1 hour, a sample was taken and analyzed to confirm 2-bromo-4-(tert-butyl)-6-(2-(methyl-d3)propan-2-yl-1,1,1,3,3,3-d6)phenyl methyl carbonate (16) was present at less than 1%. To the mixture was charged water (100 mL, 4 vol) over at least 1 hour, maintaining the temperature below 10° C. Agitation was stopped and the phases were allowed to separate, and the aqueous phase (bottom) was drained from the reactor. After resuming agitation, sodium bicarbonate (8% w/w aqueous solution, 100 mL, 4 vol, 0.62 equiv) was charged over at least 10 min, maintaining the temperature below 10° C. The temperature was adjusted to 20° C., agitation was stopped, and the phases were allowed to separate After draining the aqueous phase (bottom) from the reactor, water (100 mL, 4 vol) was charged to the reactor and the mixture was agitated for 15 min. Agitation was stopped, the phases were allowed to separate, and the aqueous phase (bottom) was drained from the reactor. To the mixture was charged water (100 mL, 4 vol), and this mixture was agitated for 15 min. Agitation was stopped, the phases were allowed to separate, and the aqueous phase (bottom) was drained from the reactor. After marking the solvent level on the reactor, a distillation head was attached and the temperature was set to 80° C. To the solution was charged methanol (570 mL. 23 vol) while distilling at the same time, matching the addition rate to the distillation rate by keeping the solvent level at the mark. Distillation was continued until the batch volume was approximately 264 mL (11 vol) and approximately 1.10 kg of distillate had been removed. The mixture was sampled and analyzed to confirm heptane was present at less than 1% v/v. The temperature was adjusted to 0° C. over 4 hours. The mother liquor was sampled and analyzed to determine the concentration of 2-bromo-4-(tert-butyl)-6-(2-(methyl-d3) propan-2-yl-1,1,1,3,3,3-d6)-3-nitrophenyl methyl carbonate (15), and the mixture was filtered. To the reactor was charged methanol (51.1 mL, 2 vol), and this was agitated until the temperature reached 0-5° C. This solution was used to wash the filter cake, and the filter cake was then dried by suction for at least 1 hour. The solid was then submitted to vacuum drying to produce 2-bromo-4-(tert-butyl)-6-(2-(methyl-d3)propan-2-yl-1,1,1,3,3,3-d6)-3-nitrophenyl methyl carbonate (15) as 41.5 g of an off-white solid (98.4% pure w/w. 63% yield after purity correction).

Procedure for the Synthesis of 5-amino-4-(tert-butyl)-2-(2-(methyl-d3)propan-2-yl-1,1,1,3,3,3-d6) phenyl methyl carbonate (7)

Charge 5 wt % (50-65 wt % wet, JM Type 37) of 5% Pd/C to a reactor. Charge (4.0 vol) Methanol Close the system. Purge with $N2_{(g)}$ at 2.0 Bar. Activate with $H2_{(g)}$ at 2.0 Bar Charge the vessel to 2.0 Bar with $H2_{(g)}$ at 25° C.+/−5° C. Stir for not less than 2 hours while maintaining a temperature of 25° C.+/−5° C. Vent and purge with $N2_{(g)}$ at 2.0 Bar. Charge compound 15 (1.0 eq) to a reactor, together with $Na_2HPO_4$ (2.3 eq). Charge (11.0 vol) Methanol. Close the system. Purge with $N2_{(g)}$ at 2.0 Bar. Activate with $H2_{(g)}$ at 2.0 Bar. Charge the vessel to 2.0 Bar with $H2_{(g)}$ at 25° C.+/−5° C. Stir for about 24 hours while maintaining a reaction temperature of 25° C.+/−5° C. Upon complete conversion, dilute reaction mixture by adding 7.7 vol of MeOH. Heat reaction mixture to 35.0° C.+/−5° C. Filter off catalyst and $Na_2HPO_4$. Wash the reactor and filter cake with Methanol (4.0 vol), and filter, combining with the initial filtrate. Check Pd content and if needed perform resin treatment (resin treatment is: Charge SPM-32 resin (5 wt %). Stir the resin treated solution for not less than 3 hours at 35.0° C.+/−5° C. Filter off resin.

Wash the reactor and filter cake with Methanol (2.0 vol), and filter, combining with the initial filtrate). Charge Norit CASP active carbon (3 wt %). Stir for not less than 3 hours at 35.0° C.+/−5° C. Filter off active carbon. Wash the reactor and filter cake with Methanol (2.0 vol), and filter, combining with the initial filtrate. Distill under vacuum at not more than 50° C. to 8.0 vol. Charge water (2.0 vol) while maintaining a temperature of 45° C.+/−5° C. Cool the resultant slurry to 0° C.+/−5° C. over 2 hours. Hold and stir the slurry at 0° C.+/−5° C. for not less than 1 hour. Filter and wash the cake with 2.0 volumes Methanol/Water (8:2) at 0° C.+/−5° C. Dry 5-amino-4-(tert-butyl)-2-(2-(methyl-d3)propan-2-yl-I,/,1,3,3,3-d6)phenyl methyl carbonate (7) under vacuum at not more than 40° C. to give a yield of a white solid. >99.5% purity.

Procedure for the Synthesis of 4-(tert-butyl)-2-(2-(methyl-d3)propan-2-yl-1,1,1,3,3,3-d6)-5-(4-oxo-1, 4-dihydroquinoline-3-carboxamido)phenyl methyl carbonate (8)

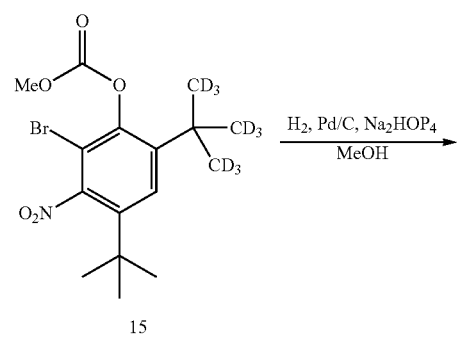

15

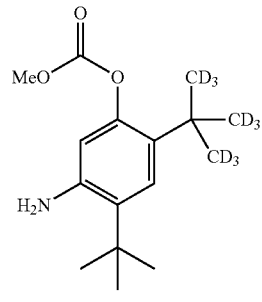

7

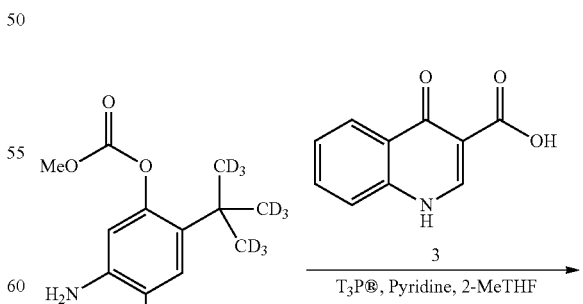

(7)

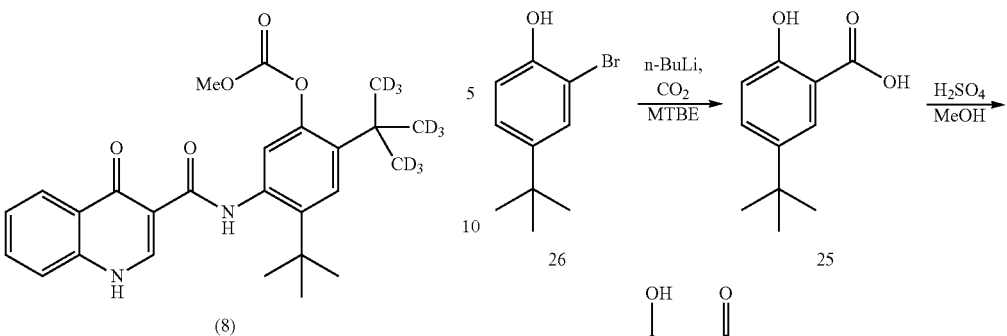

The procedure for the conversion of compound 7 into compound 8 may be performed according to the analogous procedure for compound 5.

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2) (Compound 1)

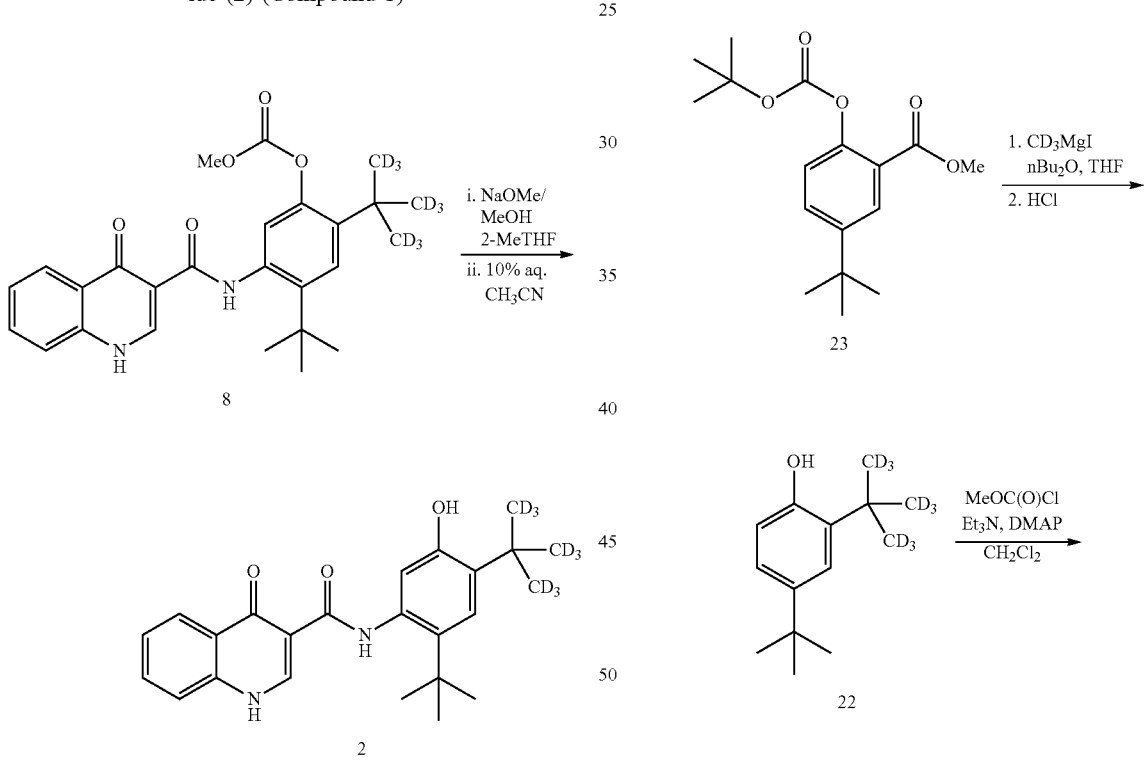

The procedure for the conversion of compound 8 into compound 2 may be performed according to the analogous procedure for the synthesis of compound 1.

Example 3: Synthesis of 5-amino-4-(tert-butyl)-2-(2-(methyl-d3)propan-2-yl-1,1,1,3,3,3-d6)phenyl methyl carbonate (7)

An alternative scheme of the synthesis of compound 7 is shown below, followed by the procedure for the synthesis of each synthetic intermediate.

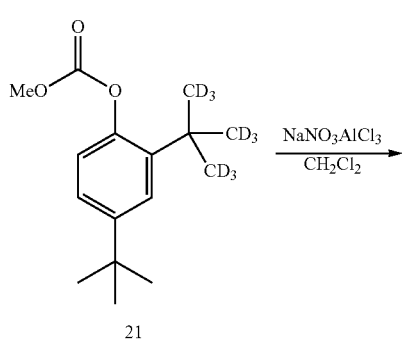

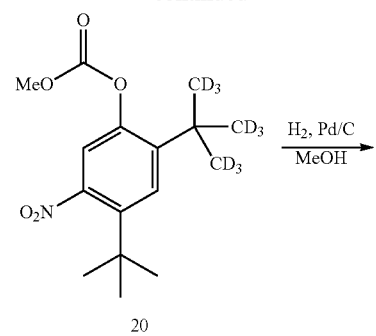

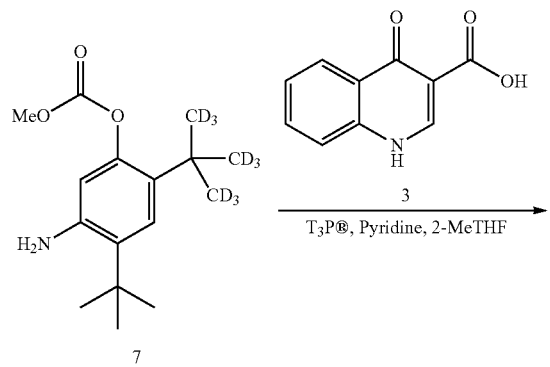

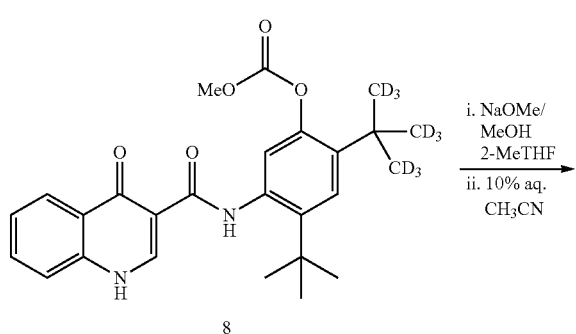

Procedure for the Synthesis of 5-(tert-butyl)-2-hydroxyphenzoic acid (15)

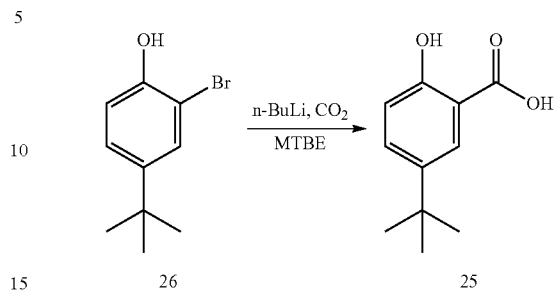

nBuLi 1.6 M in hexanes (3.49 g) was added to a round bottom flask equipped with a magnetic stirbar, a thermocouple, and a $N_2$ bubbler. The round bottom flask was cooled down to −20° C. and stirring started. A solution of 2-bromo-4-tert-butylphenol (26) (5.00 g) in MTBE (12.5 mL) was prepared, cooled to −20° C., and charged to the round bottom flask drop wise while maintaining the temperature at −20° C.+/−5° C. The reaction mixture was stirred at −20° C.+/−5° C. for 15 min then allowed to warm up to 23° C. The completeness of the lithiation was measured by $^1$H NMR (200 μL reaction mixture diluted into 0.75 mL d4-MeOH) after 15 min at room temperature. The reaction was considered complete when less than 1% 2-bromo-4-tert-butylphenol was observed. The reaction mixture was cooled down to 0° C., dry ice (solid $CO_2$) was added, and the reaction was stirred at room temperature for 45 min. Water (50.0 mL) was added to quench the reaction. The mixture was transferred into a separatory funnel, the phases were separated, and the organic phase was discarded. The aqueous phase was acidified to pH~2 with 1 M HCl (15.0 mL), then extracted with MTBE (25.0 mL) three times. The combined organic extracts were concentrated wider reduced pressure to yield 5-(tert-buty)-2-hydroxybenzoic acid (25) as a yellow solid (2.25 g. 53.15% yield); ¾ NMR (400 MHz, d4-MeOH): 7.86 (1H, d, J=2.6 Hz), 7.54 (1H, dd, J=8.7, 2.6 Hz), 6.85 (1H, d, J=2.7 Hz), 1.30 (9H, s).

Procedure for the Synthesis of Methyl 5-(tert-butyl)-2-hydroxybenzoate (24)

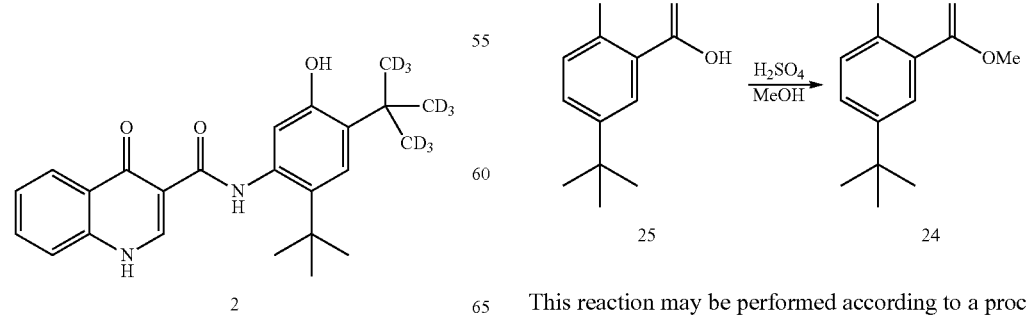

This reaction may be performed according to a procedure disclosed in *Bioorganic and Medicinal Chemistry Letters*, 2005, vol. 15(21), p. 4752-4756.

Procedure for the Synthesis of methyl 2-((tert-butoxycarbonyl)oxy)-5-(tert-butyl)benzoate (23)

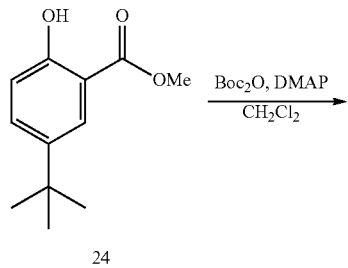

Procedure for the Synthesis of 4-(tert-butyl)-2-(2-(methyl-d3)propan-2-yl-1,1,1,3,3,3-d6)phenol (22)

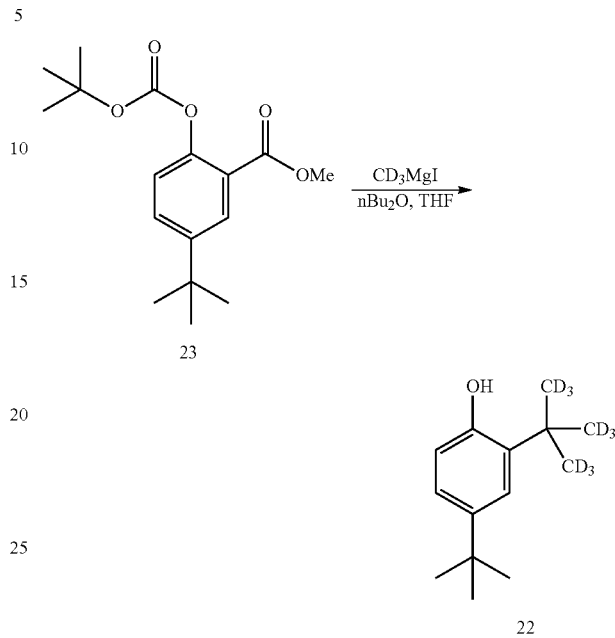

Di-/e/7-butyl carbonate (230.55 g) and CH$_2$Cl$_2$ (400 mL) were charged to a 1 L reactor and the mixture was stirred until the solids dissolved completely. Dimethylamino pyridine (0.587 g) was charged to the stirring solution along with methyl 5-(/er/-butyl)-2-hydroxybenzoate (24) (200 g). The reaction mixture was stirred at 15-30° C. and the completeness measured by HPLC (method) with sample aliquots after 60 m. The reaction was considered complete when the peak area of 5-tert-butyl-2-hydroxybenzoate (24) was less than 1%. A half-saturated solution of ammonium chloride was prepared in a separate flask by diluting saturated aqueous ammonium chloride solution (200 mL) with water (20) mL). The reaction mixture was twice washed with half saturated aqueous ammonium chloride solution (200 mL each wash). During each wash, the mixture was stirred for 15 minutes and held for 15 minutes. The organic solution was subsequently washed twice with water (100 mL each wash). During each wash, the mixture was stirred for 15 minutes and held for 15 minutes. The organic solution was transferred to a 1 L round bottom flask and concentrated below 35° C. and under vacuum to yield a white solid (275.51 g and 99.46% purity as measured by HPLC analysis (method), a 93.0% yield of methyl 2-(((er/-butoxycarbonyl)oxy)-5-(ter/-butyl)benzoate (23)) ¾ NMR (400 MHz, CDCb): 8.01 (m, 1H); 7.57 (m, 1H); 7.11 (m, 1H); 3.89 (s, 3H); 1.58 (s, 9H); 1.33 (s, 9H).

THF (176 mL) was charged to a 500 mL jacketed reactor and cooled to 5° C. To the stirring solvent and at 0-35° C. was slowly charged a solution of (methyl-d3)magnesium iodide (60.5 g) in dibutyl ether (145 mL). The resulting slurry was brought to and maintained at 20-30° C. while a solution of 2-((tert-butoxycarbonyl)oxy)-5-(/c/7-butyl (benzoate (23) (22 g) in THF (44 mL) was charged over 4-6 hours. The reaction mixture was stirred at 20-30° C. and the completeness measured by HPLC with sample aliquots after 60 m. The reaction was considered complete when the peak area of 2-(((/er/-butoxycarbonyl)oxy)-5-(/er/-butyl)benzoate (23) was less than 1%. A second reactor was charged with 6 N aqueous hydrochloric acid (110 mL) and the stirring solution was cooled to 0-10° C. The reaction slurry was slowly transferred to the acid solution at 0-35° C. The phases were stirred for 15 m and held for 15 m before being separated. The aqueous phase was extracted with dibutyl ether (132 mL). During the extraction the phases were stirred for 15 m and held for 15 m before being separated. The combined organic phases were washed sequentially with water (2×77 mL), 5% sodium thiosulfate aqueous solution (77 mL), and water (77 mL). During each wash, the mixture was stirred 15 minutes and held 15 minutes. The organic solution was transferred to a round bottom flask and concentrated below 80° C. and under vacuum to yield 4-(/er/-butyl)-2-(2-(methyl-d3)propan-2-yl-1,1,1,3,3,3-d6) phenol (22) as a crude oil (5.94 g and 83.8% purity as measured by HPLC analysis with 99.3% D9 isotopic purity by LC/MS analysis, a 84.9% yield of methyl 4-(/er/-butyl)-2-(2-(methyl-i¾)propan-2-yl-1,1,1,3,3,3-^phenol (23)). % NMR (400 MHz, CD$_3$OD): 7.22 (m, 1H); 7.00 (m, 1H): 6.65 (m, 1H); 1.26 (s, 9H).

The Grignard reaction of (23) led to some deuterium incorporation in (22). To effect H/D exchange, the mixture was subjected to a series of HCl washes:

47

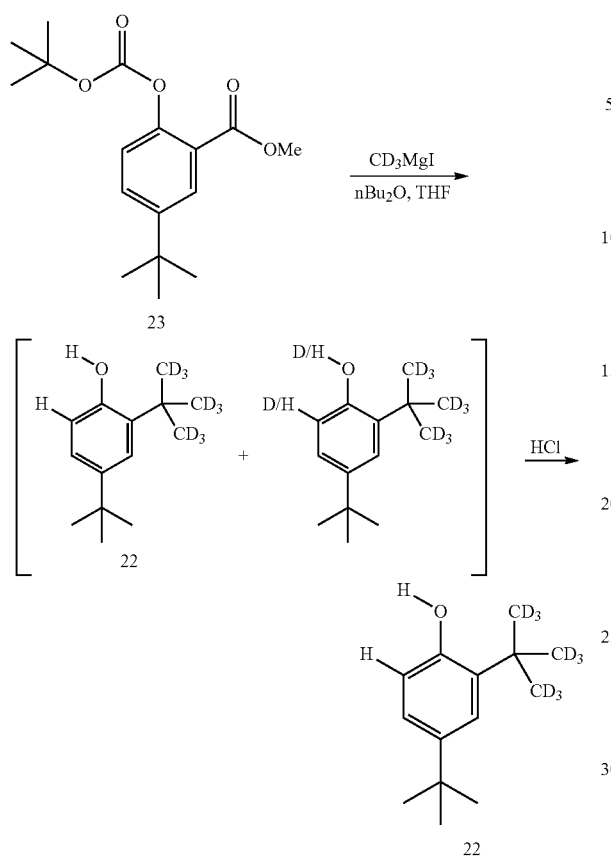

Procedure for H/D Exchange

Charge the deuterated analogs of compound 22 (1.00 equiv) to a reactor. Charge DCM (5 vol). Set jacket to 20° C. Agitate to dissolved solids. Charge 35% hydrochloric acid (5 vol). Agitate to mix the layers for not less than 6 hours Stop agitation and let the layers settle at least 30 min. Drain the bottom layer (organic) from the reactor. Drain the aqueous layer from the reactor. Charge the organic portion back into the reactor. Repeat HCl wash sequence twice Charge pre-mixed water (2.5 vol) and sat. aq. NaCl (2.5 vol). Agitate to mix the layers for 30 min. Stop agitation and let the layers settle at least 30 min. Drain the bottom layer (organic) from the reactor. Drain the aqueous from the reactor. Charge the organic portion back into the reactor. Charge water (5 vol). Agitate to mix the layers for 30 min Stop agitation and let the layers settle at least 30 min Drain the bottom layer (organic) from the reactor. Drain the aqueous from the reactor. Charge the organic portion back into the reactor. Distill the solvent wider reduced pressure to minimal volume (a rotovap with 35° C. bath temperature was used). Charge DCM (5 vol). Distill the solvent under reduced pressure to minimal volume (a rotovap with 35° C. bath temperature was used). Charge DCM (5 vol). Sample the solution and measure water content by KF. Repeat until the water content is less than 300 ppm. Note: This solution was used directly for the next reaction, so the final amount of DCM should be whatever is needed for the alkoxyformylation reaction of compound 22.

48

Procedure for the Synthesis of 4-(tert-butyl)-2-(2-(methyl-d3)propan-2-yl-L 1,1,3,3,3-d6)phenyl methyl carbonate (21)

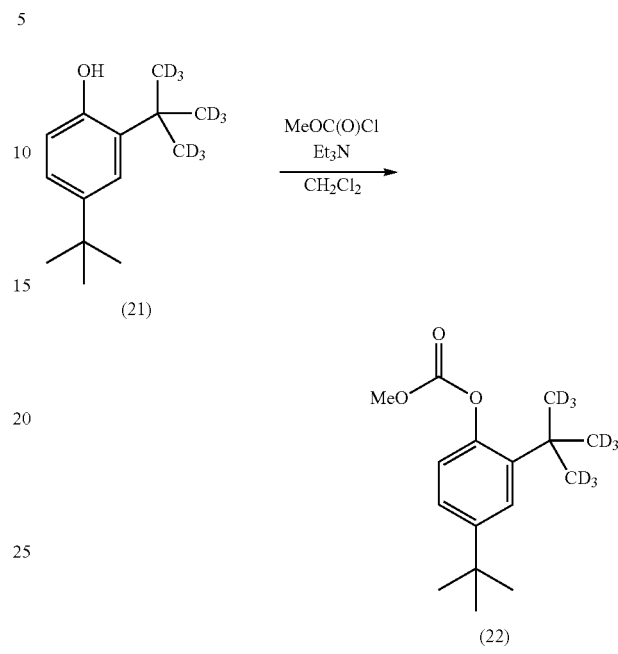

The procedure for the conversion of compound 22 into compound 21 may be performed according to the analogous procedure for compound 12.

Procedure for the Synthesis of 4-(tert-butyl)-2-(2-(methyl-d3)propan-2-yl-1,1,1,3,3,3-d6)-5-nitrophenyl methyl carbonate (20)

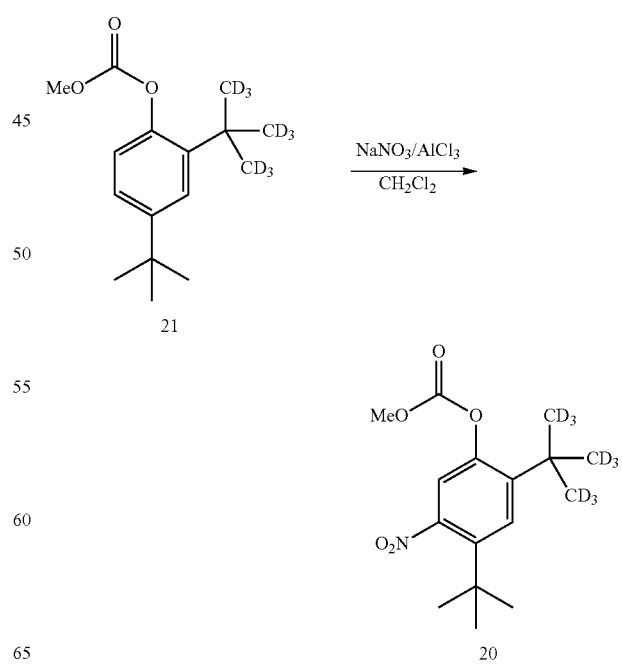

The procedure for the conversion of compound 21 into compound 20 may be performed according to the analogous procedure for compound 11A.

Procedure for the Synthesis of 5-amino-4-(tert-butyl)-2-(2-(methyl-d3)propan-2-yl-1,1,3,3,3-d6) phenylmethyl carbonate (7)

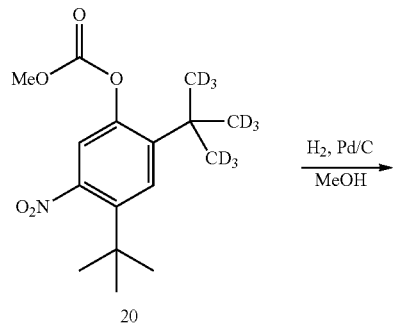

The procedure for the conversion of compound 20 into compound 7 may be performed according to the analogous procedure for compound 4.

Procedure for the Synthesis of 4-(tert-butyl)-2-(2-(methyl-d3)propan-2-yl-1,1,3,3,3-d6)-5-(4-oxo-1,4-dihydroquinoline-3-carboxamido)phenyl methyl carbonate (8)

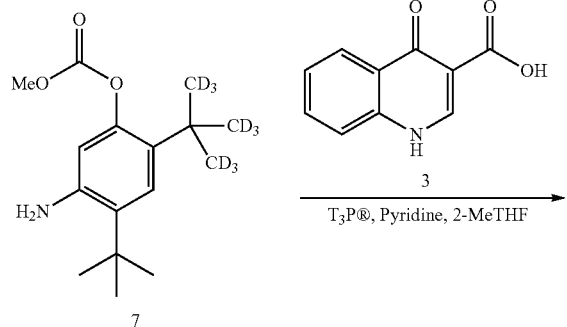

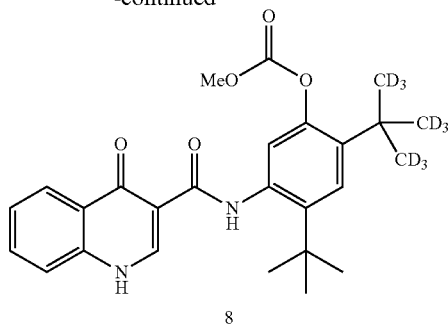

The procedure for the conversion of compound 7 into compound 8 may be performed according to the analogous procedure for compound 5.

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2) (Compound I)

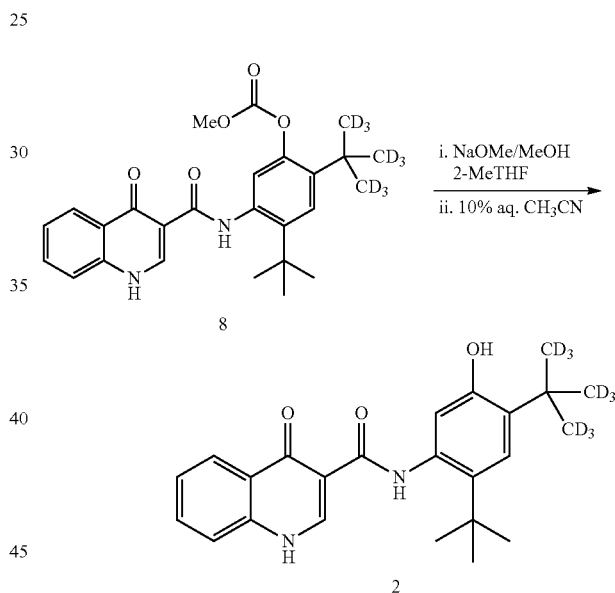

The procedure for the conversion of (8) into (2) may be performed according to the analogous procedure for the synthesis of Compound I.

Example 4: Synthesis of (14S)-8-[3-(2-{dispiro[2.0.2.1]heptan-7-yl}ethoxy)-1H-pyrazol-1-yl]-12, 12-dimethyl-2λ6-thia-3,9,11,18,23-pentaazatetracyclo[17.3.1.111,14.05,10]tetracosa-1(22),5,7,9,19(23), 20-hexaene-2,2,4-trione (Compound II)

Reagents and starting materials were obtained by commercial sources unless otherwise stated and were used without purification.

Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

Part A: Synthesis of 2-Chloro-6-[3-(2-dispiro[2.0.2.1]heptan-7-ylethoxy)pyrazol-1-yl]pyridine-3-carboxylic acid

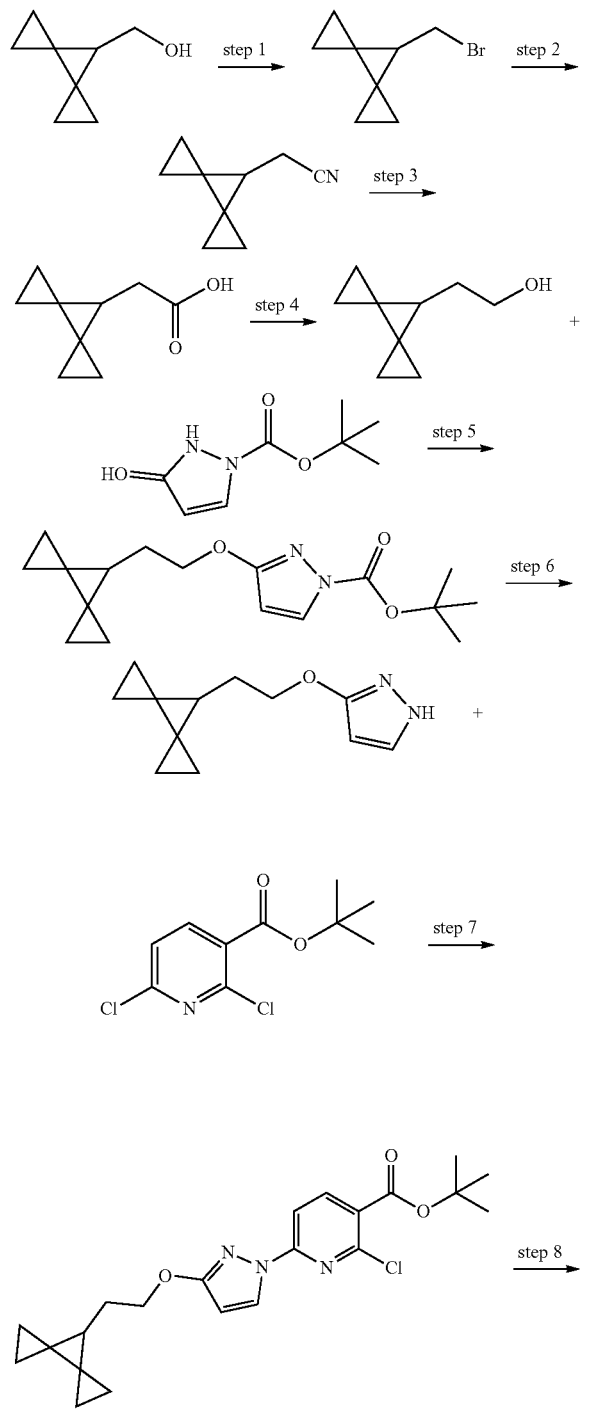

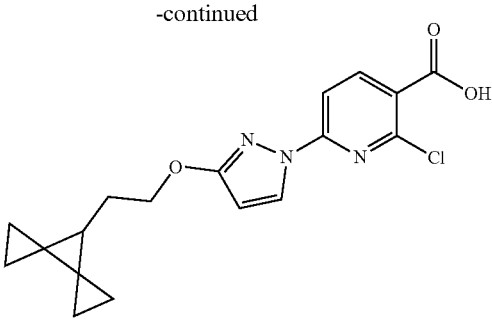

Step 1: 7-(Bromomethyl)dispiro[2.0.2.1]heptane

A 1000 mL, 3-neck round bottom flask was fitted with a mechanical stirrer, a cooling bath, an addition funnel, a J-Kem temperature probe and a nitrogen inlet/outlet. The vessel was charged under a nitrogen atmosphere with triphenylphosphine (102.7 mL, 443.2 mmol) and dichloromethane (1 L) which provided a clear colorless solution. Stirring was commenced and the cooling bath was charged with acetone. Dry ice was added in portions to the cooling bath until a pot temperature of −15° C. was obtained. The addition funnel was charged with a solution of bromine (22.82 mL, 443.0 mmol) in dichloromethane (220 mL, 10 mL/g) which was subsequently added dropwise over 1 h. Dry ice was added in portions to the cooling bath during the addition to maintain the pot temperature at −15° C. After the addition of bromine was completed, the pale yellow suspension was continued to stir at −15° C. for 15 min at which point the suspension was cooled to −30° C. The addition funnel was charged with a solution of dispiro[2.0.2.1]heptan-7-yl methanol (50 g, 402.6 mmol), pyridine (35.82 mL, 442.9 mmol) and dichloromethane (250 mL, 5 mL/g). The clear pale yellow solution was then added dropwise over 1.5 h maintaining the pot temperature at −30° C. The resulting clear light yellow reaction mixture was allowed to gradually warm to a pot temperature of −5° C. and then continued to stir at −5° C. for 1 h. The reaction mixture then was poured into hexane (2000 mL) which resulted in the formation of a precipitate. The suspension was stirred at room temperature for 30 min and then filtered through a glass frit Buchner funnel with a 20 mm layer of celite. The clear filtrate was concentrated under reduced pressure (water bath temperature at 20° C.) to provide a yellow oil with some precipitate present. The oil was diluted with some hexane, allowed to stand at room temperature for 15 min and then filtered through a glass frit Buchner funnel with a 20 mm layer of celite. The clear filtrate was concentrated under reduced pressure (water bath temperature at 20° C.) to provide 7-(bromomethyl)dispiro[2.0.2.1]heptane (70 g, 93%) as a clear yellow oil. $^1$H NMR (400 MHz, Chloroform-d) δ 3.49 (d, J=7.5 Hz, 2H), 1.90 (t, J=7.5 Hz, 1H), 1.06-0.84 (m, 4H), 0.71 (ddd, J=9.1, 5.1, 4.0 Hz, 2H), 0.54 (dddd, J=8.6, 4.8, 3.8, 1.0 Hz, 2H).

53

Step 2: 2-Dispiro[2.0.2.1]heptan-7-ylacetonitrile

A 1000 mL, 3-neck round bottom flask was fitted with a mechanical stirrer, a cooling bath used as secondary containment, a J-Kem temperature probe and a nitrogen inlet/outlet. The vessel was charged under a nitrogen atmosphere with 7-(bromomethyl)dispiro[2.0.2.1]heptane (35 g, 187.1 mmol) and dimethyl sulfoxide (245 mL) which provided a clear amber solution. Stirring was commenced and the pot temperature was recorded at 19° C. The vessel was then charged with sodium cyanide (11.46 g, 233.8 mmol) added as a solid in one portion which resulted in a dark solution and a gradual exotherm to 49° C. over 15 min. After a few min the pot temperature began to decrease and the mixture was continued to stir at room temperature overnight (about 15 h). The dark reaction mixture was quenched with ice cold saturated sodium carbonate solution (500 mL) and then transferred to a separatory funnel and partitioned with diethyl ether (500 mL). The organic was removed and the residual aqueous was extracted with diethyl ether (2×250 mL). The combined organics were washed with water (500 mL), dried over sodium sulfate (200 g) and then filtered through a glass frit Buchner funnel. The clear amber filtrate was concentrated under reduced pressure (water bath temperature 20° C.) to provide 2-dispiro[2.0.2.1]heptan-7-ylacetonitrile (21 g, 84%) as a clear dark amber oil. $^1$H NMR (400 MHz, Chloroform-d) δ 2.42 (d, J=6.6 Hz, 2H), 1.69 (t, J=6.6 Hz, 1H), 1.02-0.88 (m, 4H), 0.79-0.70 (m, 2H), 0.66-0.55 (m, 2H).

Step 3: 2-Dispiro[2.0.2.1]heptan-7-ylacetic acid

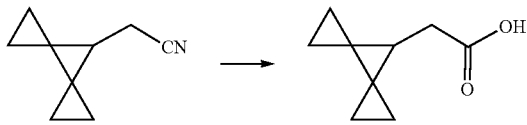 [SMILES: N#CCC1C2(CC2)C12CC2 ; O=C(O)CC1C2(CC2)C12CC2]

To a solution of 2-dispiro[2.0.2.1]heptan-7-ylacetonitrile (2.1 g, 14.19 mmol) in EtOH (32 mL) was added sodium hydroxide (5.12 g, 128.0 mmol) followed by water (13 mL) and the resulting solution was stirred and heated to 70° C. overnight. The mixture was then cooled to room temperature, diluted with water and extracted with diethyl ether. The aqueous phase was adjusted to pH=1 by the addition of 6 N hydrochloric acid (resulting in a cloudy precipitate) and extracted with diethyl ether (3×). The organic phases were dried (magnesium sulfate), filtered and concentrated giving 2-dispiro[2.0.2.1]heptan-7-ylacetic acid (2.19 g, 99% yield, 98% purity) as an orange solid which was used in the next step without further purification. $^1$H NMR (400 MHz, Chloroform-d) δ 2.44 (d, J=6.9 Hz, 2H), 1.67 (t, J=6.9 Hz, 1H), 0.91 (ddd, J=9.0, 5.2, 3.9 Hz, 2H), 0.81 (dddd, J=8.9, 5.2, 3.9, 0.5 Hz, 2H), 0.69 (ddd, J=8.9, 5.2, 3.9 Hz, 2H), 0.56-0.44 (m, 2H).

54

Step 4: 2-Dispiro[2.0.2.1]heptan-7-ylethanol

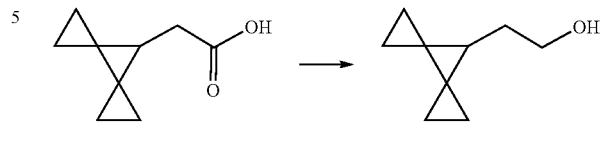

To lithium aluminum hydride (827.4 mg, 902.3 µL, 21.80 mmol) dissolved in tetrahydrofuran (33.71 mL) cooled in an ice/water bath was added 2-dispiro[2.0.2.1]heptan-7-ylacetic acid (2.552 g, 16.77 mmol) in tetrahydrofuran (7.470 mL) dropwise over 15 min keeping the reaction temperature <20° C. The mixture was allowed to stir a total of 18 h, gradually warming to ambient temperature. The mixture was cooled with an ice/water bath and sequentially quenched with slow addition of water (838.4 mg, 838.4 µL, 46.54 mmol), followed by sodium hydroxide (1.006 mL of 5 M, 5.031 mmol), then water (2.493 g, 2.493 mL, 138.4 mmol) affording a white, granular slurry which was filtered over celite. Washed the filtered solid with diethyl ether. The filtrate was concentrated in vacuo at ~300 mbar and 30° C. water bath. Diluted the residue with diethyl ether, dried (magnesium sulfate), filtered and concentrated in vacuo at ~300 mbar and 30° C. water bath followed by ~30 s under vacuum to give 2-dispiro[2.0.2.1]heptan-7-ylethanol (2.318 g, 100%) which was used directly in the ensuing step without further purification. $^1$H NMR (400 MHz, Chloroform-d) δ 3.64 (s, 2H), 1.68 (d, J=6.7 Hz, 2H), 1.39 (s, 1H), 1.31 (s, 1H), 0.82 (d, J=14.0 Hz, 4H), 0.65 (s, 2H), 0.50 (d, J=3.6 Hz, 2H).

Step 5: tert-Butyl 3-(2-dispiro[2.0.2.1]heptan-7-ylethoxy)pyrazole-1-carboxylate

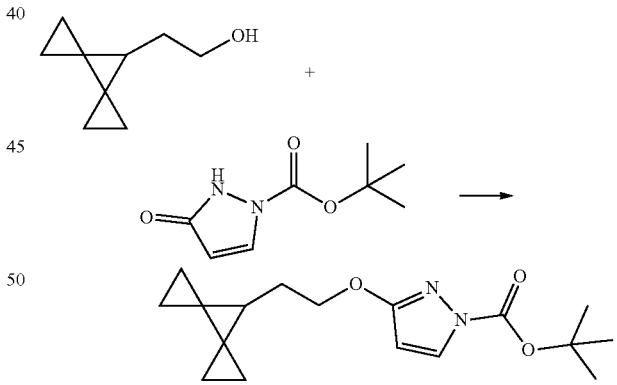

To a solution of tert-butyl 5-oxo-1H-pyrazole-2-carboxylate (2.942 g, 15.97 mmol) and 2-dispiro[2.0.2.1]heptan-7-ylethanol (2.318 g, 16.77 mmol) in tetrahydrofuran (36.78 mL) was added triphenylphosphine (4.399 g, 16.77 mmol). To the mixture was slowly added diisopropyl azodicarboxylate (3.391 g, 3.302 mL, 16.77 mmol) dropwise over 10 min (mild exotherm noted). The reaction mixture was stirred at room temperature for 30 min then at 50° C. for 30 min. The tetrahydrofuran was removed in vacuo. To the crude residue was added toluene (23.54 mL) and the mixture was stirred overnight as a precipitate gradually crystallized. Slurried with Celite then the precipitate was filtered off and washed with toluene (8.705 mL) and again with toluene (8.705 mL). The filtrate was concentrated in vacuo. The crude product was purified by silica gel chromatography using a shallow gradient from 100% hexanes to 100% ethyl acetate giving tert-butyl 3-(2-dispiro[2.0.2.1]heptan-7-ylethoxy)pyrazole-1-carboxylate (3.449 g, 71%). ESI-MS m/z calc. 304.17868, found 305.1 (M+1)+; Retention time: 0.82 min (LC Method A).

Step 6: 3-(2-Dispiro[2.0.2.1]heptan-7-ylethoxy)-1H-pyrazole

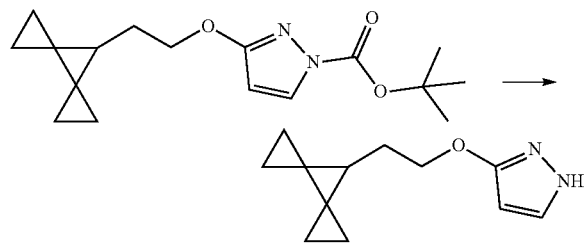

tert-Butyl 3-(2-dispiro[2.0.2.1]heptan-7-ylethoxy)pyrazole-1-carboxylate (5.304 g, 17.43 mmol) was dissolved in dichloromethane (53.04 mL) with trifluoroacetic acid (29.81 g, 20.14 mL, 261.4 mmol) and the reaction was stirred at room temperature for 120 min. The reaction was evaporated and the resulting oil was partitioned between ethyl acetate and a saturated sodium bicarbonate solution and the layers separated. The aqueous portion was extracted two additional times with ethyl acetate, then the organics were combined, washed with brine, dried over sodium sulfate, filtered and evaporated to give an oil, 3-(2-dispiro[2.0.2.1]heptan-7-ylethoxy)-1H-pyrazole (3.56 g, 100%). ESI-MS m/z calc. 204.12627, found 205.1 (M+1)+; Retention time: 0.59 min (LC Method A).

Step 7: tert-Butyl 2-chloro-6-[3-(2-dispiro[2.0.2.1]heptan-7-ylethoxy)pyrazol-1-yl]pyridine-3-carboxylate

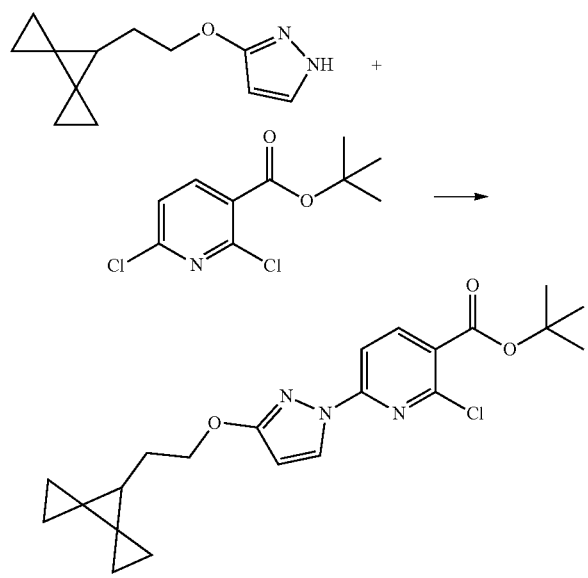

tert-Butyl 2,6-dichloropyridine-3-carboxylate (4.322 g, 17.42 mmol), 3-(2-dispiro[2.0.2.1]heptan-7-ylethoxy)-1H-pyrazole (3.559 g, 17.42 mmol) and potassium carbonate (2.891 g, 20.92 mmol) were combined in anhydrous dimethyl sulfoxide (71.18 mL). 1,4-Diazabicyclo[2.2.2]octane (391.1 mg, 3.487 mmol) was added and the mixture was stirred at room temperature under nitrogen for 16 h. The reaction mixture was diluted with water (136.9 mL) and stirred for 15 min. The resulting white solid was filtered and washed with water. The solid was dissolved in dichloromethane and dried over magnesium sulfate. The mixture was filtered and evaporated to give tert-butyl 2-chloro-6-[3-(2-dispiro[2.0.2.1]heptan-7-ylethoxy)pyrazol-1-yl]pyridine-3-carboxylate (5.69 g, 79%) as a white solid. $^1$H NMR (400 MHz, Chloroform-d) δ 8.35 (d, J=2.9 Hz, 1H), 8.18 (d, J=8.4 Hz, 1H), 7.69 (d, J=8.4 Hz, 1H), 5.94 (d, J=2.9 Hz, 1H), 4.25 (s, 2H), 1.90 (d, J=6.8 Hz, 2H), 1.62 (s, 9H), 1.49 (t, J=6.6 Hz, 1H), 0.85 (d, J=1.5 Hz, 4H), 0.65 (d, J=1.5 Hz, 2H), 0.52 (d, J=1.1 Hz, 2H). ESI-MS m/z calc. 415.16626, found 360.0 (M-tBu)+; Retention time: 2.09 min (LC Method B).

Step 8: 2-Chloro-6-[3-(2-dispiro[2.0.2.1]heptan-7-ylethoxy)pyrazol-1-yl]pyridine-3-carboxylic acid

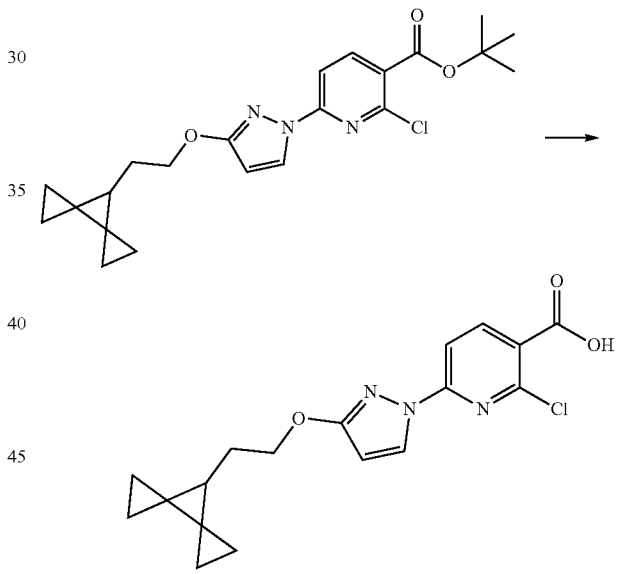

tert-Butyl 2-chloro-6-[3-(2-dispiro[2.0.2.1]heptan-7-ylethoxy)pyrazol-1-yl]pyridine-3-carboxylate (5.85 g, 14.07 mmol) was dissolved in dichloromethane (58.5 mL) with trifluoroacetic acid (16.26 mL, 211.1 mmol) and the reaction was stirred at room temperature for 16 h. The reaction was evaporated and to the resulting solid was added ether and then removed the ether under reduced pressure. This evaporation from ether was repeated twice more resulting in a white solid, 2-chloro-6-[3-(2-dispiro[2.0.2.1]heptan-7-ylethoxy)pyrazol-1-yl]pyridine-3-carboxylic acid (5.06 g, 100%). $^1$H NMR (400 MHz, Chloroform-d) δ 8.41 (d, J=8.5 Hz, 1H), 8.37 (d, J=2.9 Hz, 1H), 7.75 (d, J=8.5 Hz, 1H), 5.97 (d, J=2.9 Hz, 1H), 4.27 (s, 2H), 1.91 (d, J=6.7 Hz, 2H), 1.50 (s, 1H), 0.85 (d, J=1.5 Hz, 4H), 0.71-0.62 (m, 2H), 0.52 (d, J=1.1 Hz, 2H). ESI-MS m/z calc. 359.10367, found 360.2 (M+1)+; Retention time: 2.16 min (LC Method B).

Part B: Synthesis of tert-Butyl (4S)-2,2-dimethyl-4-[3-[[(6-sulfamoyl-2-pyridyl)amino]propyl]pyrrolidine-1-carboxylate

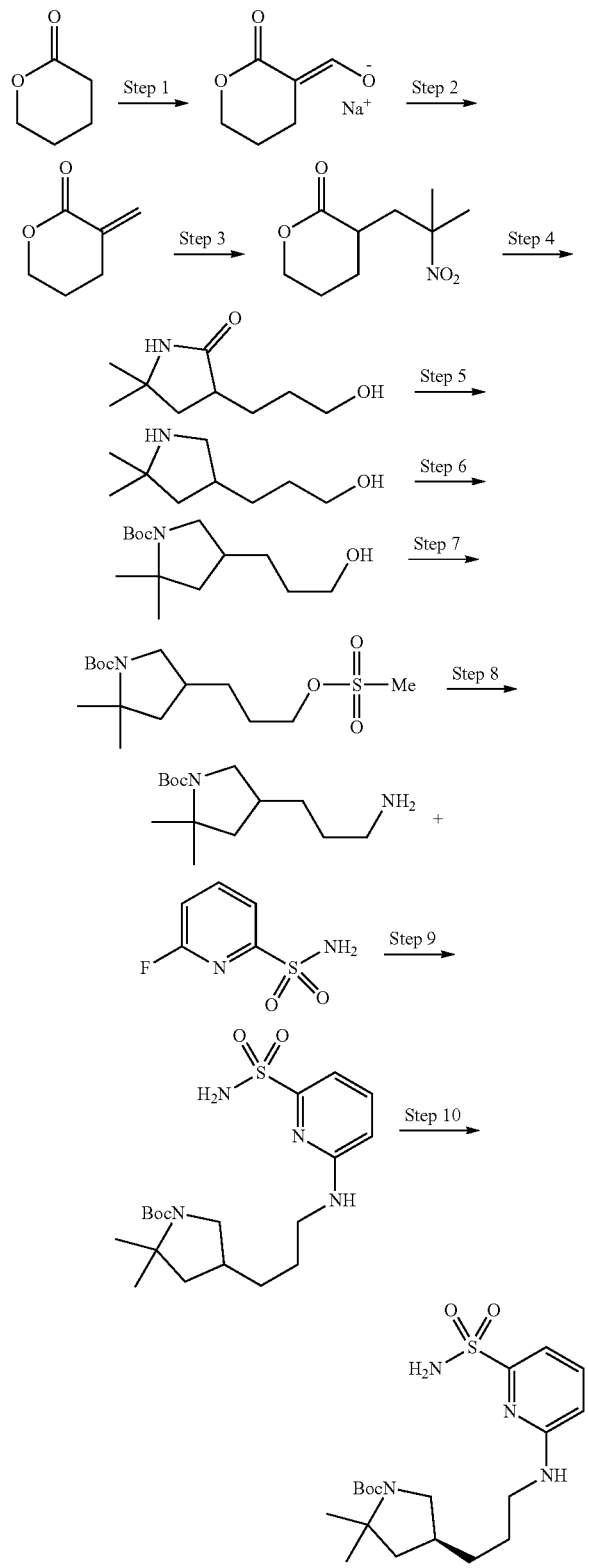

Step 1:
(E)-(2-Oxotetrahydropyran-3-ylidene)methanolate (Sodium Salt)

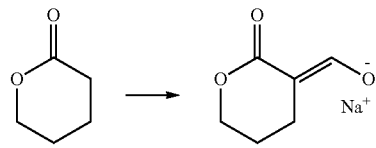 [SMILES: O=C1CCCCO1 ; O=C1OCCC/C1=C\O ; [Na+]]

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with sodium hydride (59.91 g of 60% w/w, 1.498 mol) followed by heptane (1.5 L) which provided a grey suspension. Stirring was commenced and the pot temperature was recorded at 19° C. The vessel was then charged with ethyl alcohol (3.451 g, 74.91 mmol) added via syringe which resulted in gas evolution. The addition funnel was charged with a clear pale yellow solution of tetrahydropyran-2-one (150 g, 1.498 mol) and ethyl formate (111 g, 1.50 mol). The solution was added dropwise over 1 h which resulted in gas evolution and a gradual exotherm to 45° C. The resulting thick white suspension was then heated to 65° C. for 2 h and then allowed to cool to room temperature. The mixture was continued to stir at room temperature overnight (about 10 h). The reaction mixture was vacuum filtered through a glass frit Buchner funnel (medium porosity) under a stream of nitrogen. The filter cake was displacement washed with heptane (2×250 mL) and pulled for a few min. The slightly heptane wet cake was transferred to a glass tray and dried in a vacuum oven at 45° C. for 15 h to provide a white solid (205 g, 1.36 mol, 91% yield) as the desired product, (E)-(2-oxotetrahydropyran-3-ylidene)methanolate (sodium salt).

Step 2: 3-Methylenetetrahydropyran-2-one

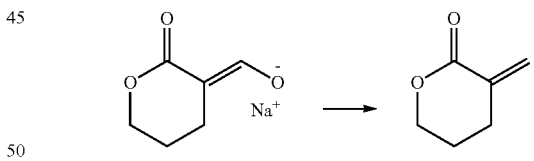

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with (E)-(2-oxotetrahydropyran-3-ylidene)methanolate (sodium salt) (205 g, 1.366 mol) (205 g, 1.366 mol) and tetrahydrofuran (1640 mL) which provided a white suspension. Stirring was commenced and the pot temperature was recorded at 19° C. The vessel was then charged with paraformaldehyde (136.6 g, 4.549 mol) added as a solid in one portion. The resulting suspension was heated to 63° C. and the condition was maintained for 15 h. Upon heating the reaction mixture became slightly gelatinous. The white gelatinous mixture was concentrated under reduced pressure to remove most of the tetrahydrofuran. The remaining residue was partitioned with ethyl acetate (1000 mL), saturated sodium chloride (500 mL) and saturated sodium hydrogen carbonate (500 mL) in a separatory funnel. The organic was removed and the residual aqueous was extracted with ethyl acetate (5×300 mL). The combined organic was dried over sodium sulfate (500 g) and then vacuum filtered through a glass frit Buchner funnel with a 20 mm layer of celite. The filter cake was displacement washed with ethyl acetate (250 mL). The clear filtrate was concentrated under reduced pressure to provide a clear pale yellow oil (135 g) as the desired crude product. The material was purified by silica gel column flash chromatography (liquid load) eluting with a gradient of 100% hexane to 60% ethyl acetate in hexane over 1 h collecting 450 mL fractions. The product was detected by TLC analysis on silica gel eluting with 3:1 hexanes/ethyl acetate and visualized under UV. The product fractions were combined and concentrated under reduced pressure to provide a clear, colorless oil (132 g, 1.18 mol, 72% yield containing 16 wt % residual ethyl acetate by NMR) as the desired product, 3-methylenetetrahydropyran-2-one. 1H NMR (400 MHz, dimethyl sulfoxide-$d_6$) δ 6.18 (q, J=1.9 Hz, 1H), 5.60 (q, J=1.9 Hz, 1H), 4.40-4.26 (m, 2H), 2.61 (ddt, J=7.0, 6.3, 2.0 Hz, 2H), 1.90-1.75 (m, 2H).

Step 3:
3-(2-Methyl-2-nitro-propyl)tetrahydropyran-2-one

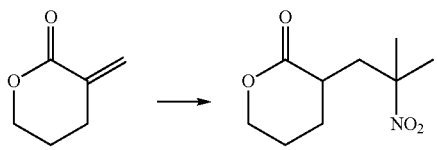

A 5000 mL, 3-neck round bottom flask was fitted with a mechanical stirrer, a cooling bath used as secondary containment, a J-Kem temperature probe, an addition funnel and a nitrogen inlet/outlet. The vessel was charged under a nitrogen atmosphere with 2-nitropropane (104.9 g, 1.177 mol). Stirring was commenced and the pot temperature was recorded at 19° C. The vessel was then charged with 1,8-diazabicyclo[5.4.0]undec-7-ene (22.41 g, 147.2 mmol) added neat in one portion which resulted in a clear light yellow solution. No exotherm was observed. The addition funnel was charged with a solution of 3-methylenetetrahydropyran-2-one (110 g, 981.0 mmol) in acetonitrile (1100 mL) which was added dropwise over 1 h which resulted in a clear light yellow solution and a gradual exotherm to 24° C. The reaction mixture was continued to stir at room temperature for 3.5 h and then concentrated under reduced pressure. The remaining residue was dissolved in dichloromethane (1000 mL) and partitioned with 500 mL of a 3:2 mixture of 1 molar citric acid solution/saturated sodium chloride solution. The resulting organic phase was a clear pale blue solution and the aqueous phase was a slightly cloudy very pale blue solution. The organic was removed and the residual aqueous was extracted with dichloromethane (300 mL). The combined organic was washed with saturated sodium chloride solution (300 mL), dried over sodium sulfate (250 g) and then filtered through a glass frit Buchner funnel. The filtrate was concentrated under reduced pressure to a volume of about 200 mL. The clear pale blue dichloromethane solution was diluted with methyl tert-butyl ether (1500 mL) and the cloudy solution was concentrated under reduced pressure to a volume of about 200 mL which provided a suspension. The mixture was again diluted with methyl tert-butyl ether (1500 mL) and concentrated under reduced pressure to a volume of about 250 mL. The resulting suspension was allowed to stand at room temperature overnight (about 12 h). The solid was collected by vacuum filtration in a glass frit Buchner funnel and the filter cake was displacement washed with cold methyl tert-butyl ether (2×150 mL) and then pulled for 30 min. The material was further dried in a vacuum oven at 45° C. for 5 h to provide (160 g, 0.795 mol, 81% yield) of a white solid as the desired product, 3-(2-methyl-2-nitro-propyl)tetrahydropyran-2-one. $^1$H NMR (400 MHz, dimethyl sulfoxide-$d_6$) δ 4.34 (ddd, J=11.1, 9.3, 4.3 Hz, 1H), 4.20 (dt, J=11.1, 5.1 Hz, 1H), 2.75-2.62 (m, 1H), 2.56 (dd, J=14.9, 5.2 Hz, 1H), 2.01-1.89 (m, 2H), 1.89-1.67 (m, 2H), 1.55 (d, J=6.0 Hz, 6H), 1.44 (dddd, J=12.8, 11.5, 8.1, 6.6 Hz, 1H).

Step 4:
3-(3-Hydroxypropyl)-5,5-dimethyl-pyrrolidin-2-one

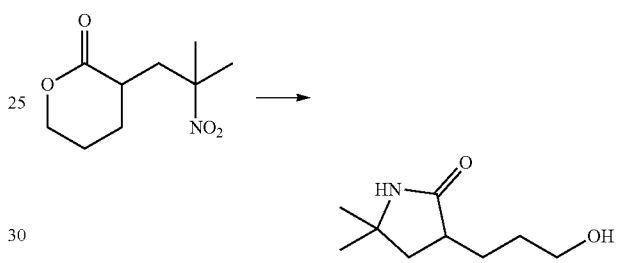

A 1000 mL, 3-neck round bottom flask was fitted with a Teflon stir bar, a heating mantle, a J-Kem temperature probe/controller and rubber septums. The vessel was charged with 3-(2-methyl-2-nitro-propyl)tetrahydropyran-2-one (25 g, 124.2 mmol) and ethyl alcohol (375 mL) which provided a white suspension. Stirring was commenced and the suspension was heated to 40° C. for 10 min which provided a clear colorless solution. The vessel was then fitted with a gas dispersion tube and the solution was degassed with nitrogen for 15 min. The vessel was then charged with Raney Nickel (8.019 g of 50% w/w, 68.31 mmol) and the vessel was then fitted with the septums. The vessel was evacuated and placed under a hydrogen atmosphere. The process was repeated for three cycles. The vessel was then placed under 1 atmosphere hydrogen and the reaction mixture was gradually heated to 60° C. The reaction was continued to stir at 60° C. for 24 h. After cooling to room temperature, the vessel was fitted with a gas dispersion tube and the reaction mixture was degassed with nitrogen for 15 min. The mixture was vacuum filtered through a glass frit Buchner funnel with a 20 mm layer of celite. The filter cake was displacement washed with ethanol (2×100 mL) and pulled until slightly ethyl alcohol wet, then wetted with water and the used Raney nickel catalyst was discarded under water. The clear pale amber filtrate was concentrated under reduced pressure to a clear viscous light amber oil. The oil was diluted with methyl tert-butyl ether (1500 mL) and the cloudy solution was concentrated under reduced pressure to a volume of about 150 mL which provided a suspension. The mixture was again diluted with methyl tert-butyl ether (1500 mL) and concentrated under reduced pressure to a volume of about 150 mL. The resulting suspension was allowed to stand at room temperature overnight (about 12 h). The solid was collected by vacuum filtration in a glass frit Buchner funnel and the filter cake was displacement washed with cold methyl tert-butyl ether (2×50 mL) and then pulled for 30 min. The material was further dried in a vacuum oven at 45° C. for 3 h to provide a white solid (19 g, 0.111 mol, 89% yield) as the product, 3-(3-hydroxypropyl)-5,5-dimethyl-pyrrolidin-2-one. ¹H NMR (400 MHz, dimethyl sulfoxide-d₆) δ 7.63 (s, 1H), 3.38 (t, J=6.5 Hz, 2H), 2.37 (tdd, J=9.8, 8.5, 4.4 Hz, 1H), 2.02 (dd, J=12.3, 8.6 Hz, 1H), 1.72 (tdd, J=9.6, 7.5, 4.4 Hz, 1H), 1.52-1.32 (m, 3H), 1.28-1.03 (m, 7H).

Step 5: 3-(5,5-Dimethylpyrrolidin-3-yl)propan-1-ol

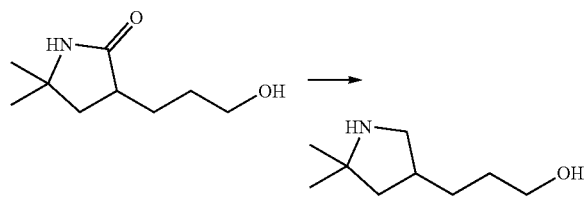

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with lithium aluminum hydride pellets (19.39 g, 510.9 mmol). The vessel was then charged with tetrahydrofuran (500 mL, 20 mL/g). Stirring was commenced and the pot temperature was recorded at 20° C. The mixture was allowed to stir at room temperature for 0.5 h to allow the pellets to dissolve. The pot temperature of the resulting grey suspension was recorded at 24° C. The addition funnel was charged with a solution of 3-(3-hydroxypropyl)-5,5-dimethyl-pyrrolidin-2-one (25 g, 146.0 mmol) in tetrahydrofuran (500 mL) and the clear pale yellow solution was added dropwise over 90 min. Slight heating was required to achieve homogeneity. After the completed addition the pot temperature of the resulting greyish suspension was recorded at 24° C. The mixture was then heated to a pot temperature of 65° C. and the condition was maintained for 72 h. Analysis of the reaction mixture at this point indicated some residual starting material still remaining and no change in product formation. The reaction was subsequently stopped at this point. The heating mantle was removed and the vessel was fitted with a cooling bath. The suspension was cooled to 0° C. with a crushed ice/water cooling bath and then quenched by the very slow dropwise addition of water (19.93 mL), followed by 15 wt % sodium hydroxide solution (19.93 mL) and then finally with water (59.79 mL). The pot temperature of the resulting white suspension was recorded at 5° C. The cooling bath was removed and the vessel was again fitted with a heating mantle. The suspension was warmed to 60° C. and the condition was maintained for 30 min. The warm suspension was vacuum filtered through a glass frit Buchner funnel with a 20 mm layer of celite. The filter cake was then displacement washed with 60° C. tetrahydrofuran (2×250 mL) and then pulled for 30 min. The clear filtrate was concentrated under reduced pressure to provide (23.5 g, 0.149 mol, 99% yield) of a clear light yellow viscous oil as the desired product, 3-(5,5-dimethylpyrrolidin-3-yl)propan-1-ol. ¹H NMR (400 MHz, dimethyl sulfoxide-d₆) δ 3.37 (dt, J=8.3, 6.4 Hz, 3H), 2.95 (dd, J=10.6, 7.6 Hz, 1H), 2.40 (dd, J=10.7, 7.7 Hz, 1H), 2.04 (dt, J=16.1, 8.1 Hz, 1H), 1.69 (dd, J=12.2, 8.2 Hz, 1H), 1.50-1.24 (m, 5H), 1.11-0.94 (m, 7H).

Step 6: tert-Butyl 4-(3-hydroxypropyl)-2,2-dimethyl-pyrrolidine-1-carboxylate

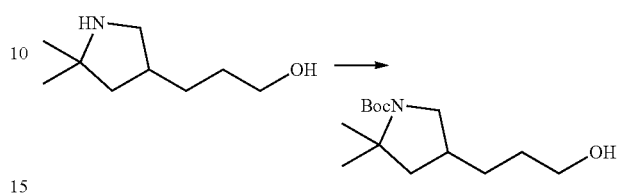

A 1 L, 3-neck round bottom flask was fitted with a mechanical stirrer, a cooling bath, an addition funnel, a J-Kem temperature probe and a nitrogen inlet/outlet. The vessel was charged under a nitrogen atmosphere with 3-(5,5-dimethylpyrrolidin-3-yl)propan-1-ol (15 g, 95.39 mmol) and dichloromethane (225 mL, 15 mL/g) which provided a clear light yellow solution. Stirring was commenced and the pot temperature was recorded at 19° C. The cooling bath was charged with crushed ice/water and the pot temperature was lowered to 0° C. The addition funnel was charged with triethylamine (12.55 g, 124.0 mmol) which was subsequently added neat dropwise over 5 min. No exotherm was observed. The addition funnel was then charged with di-tert-butyl dicarbonate (22.89 g, 104.9 mmol) dissolved in dichloromethane (225 mL). The clear pale yellow solution was then added dropwise over 30 min which resulted in gentle gas evolution. No exotherm was observed. The cooling bath was removed and the resulting clear light yellow solution was allowed to warm to room temperature and continue to stir at room temperature for 3 h. The reaction mixture was transferred to a separatory funnel and partitioned with water (75 mL). The organic was removed and washed with saturated sodium chloride solution (75 mL), dried over sodium sulfate (150 g) and then filtered through a glass frit Buchner funnel. The filtrate was concentrated under reduced pressure to provide (30 g) of a clear light yellow oil as the desired crude product. The material was purified by silica gel column flash chromatography (liquid load with dichloromethane) eluting with a gradient of 100% dichloromethane to 10% methyl alcohol in dichloromethane over 60 min collecting 50 mL fractions. The desired product fractions were combined and concentrated under reduced pressure to provide tert-butyl 4-(3-hydroxypropyl)-2,2-dimethyl-pyrrolidine-1-carboxylate (22 g, 0.0855 mol, 90% yield) as a clear pale yellow viscous oil. ¹H NMR (400 MHz, DMSO-d6) δ 4.38 (td, J=5.2, 1.4 Hz, 1H), 3.54 (dt, J=10.3, 6.7 Hz, 1H), 3.38 (td, J=6.6, 3.5 Hz, 2H), 2.76 (q, J=10.3 Hz, 1H), 2.07 (td, J=11.6, 5.7 Hz, 1H), 1.87 (ddd, J=16.7, 12.1, 6.0 Hz, 1H), 1.37 (dd, J=14.2, 10.4 Hz, 17H), 1.24 (s, 3H).

Step 7: tert-Butyl 2,2-dimethyl-4-(3-methylsulfonyl oxypropyl)pyrrolidine-1-carboxylate

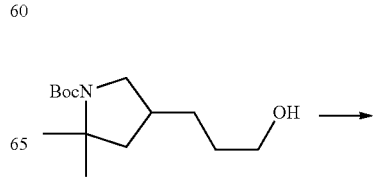

63

-continued

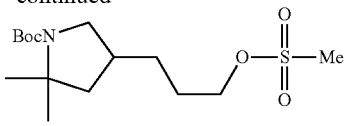

tert-Butyl 4-(3-hydroxypropyl)-2,2-dimethyl-pyrrolidine-1-carboxylate (50.5 g, 196.22 mmol) and triethylamine (39.711 g, 54.698 mL, 392.44 mmol) were dissolved in dichloromethane (500 mL) and the resulting solution was chilled in an ice water bath for 30 min. Mesyl chloride (24.725 g, 16.706 mL, 215.84 mmol) was added dropwise over a 30 min period, then the ice bath was removed and the mixture stirred at room temperature for one h. The reaction was then quenched with saturated sodium bicarbonate solution (200 mL). The phases were separated and the organic phase was extracted with saturated sodium bicarbonate (200 mL) and water (2×100 mL). The aqueous phases were discarded and the organic phase was dried over sodium sulfate, filtered and concentrated in vacuo to obtain tert-butyl 2,2-dimethyl-4-(3-methylsulfonyl oxypropyl)pyrrolidine-1-carboxylate (64.2 g, 93%) as a pale yellow oil. ESI-MS m/z calc. 335.1766, found 336.4 (M+1)$^+$; Retention time: 5.54 min (LC Method Q).

Step 8: tert-Butyl 4-(3-aminopropyl)-2,2-dimethyl-pyrrolidine-1-carboxylate

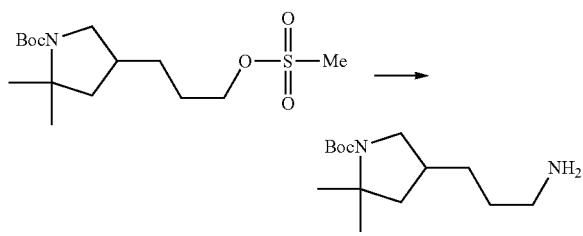

tert-Butyl 2,2-dimethyl-4-(3-methylsulfonyloxypropyl) pyrrolidine-1-carboxylate (64.2 g, 191.38 mmol) was dissolved in dioxane (650 mL) and then ammonium hydroxide (650 mL) was added and the resulting mixture heated to 45° C. for 18 h. After 18 h, the reaction was cooled to room temperature. The solution was diluted with 1M sodium hydroxide (200 mL) and then extracted with diethyl ether (3×650 mL). The aqueous phase was discarded and the combined organic phases were extracted with water (2×200 mL). The aqueous phases were discarded and the organic phase was dried over sodium sulfate, filtered and concentrated in vacuo to afford tert-butyl 4-(3-aminopropyl)-2,2-dimethyl-pyrrolidine-1-carboxylate (48.9 g, 95%) as a pale yellow oil. ESI-MS m/z calc. 256.2151, found 257.3 (M+1)+; Retention time: 3.70 min (LC Method Q).

Step 9: tert-Butyl 2,2-dimethyl-4-[3-[(6-sulfamoyl-2-pyridyl)amino]propyl]pyrrolidine-1-carboxylate

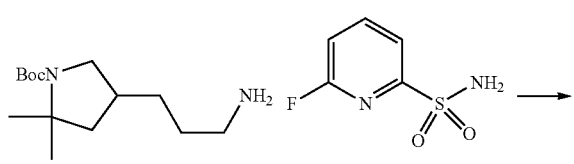

64

-continued

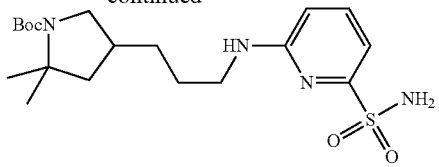

To tert-butyl 4-(3-aminopropyl)-2,2-dimethyl-pyrrolidine-1-carboxylate (8.91 g, 34.8 mmol) and 6-fluoropyridine-2-sulfonamide (6.13 g, 34.8 mmol) in dimethyl sulfoxide (75 mL) was added potassium carbonate (4.91 g, 35.5 mmol) and the mixture stirred at 100° C. for 12 h and then allowed to cool to ambient temperature and stirred for an additional 4 h (16 h total). The reaction mixture was slowly poured into hydrochloric acid (35 mL of 1 M, 35.00 mmol) in water (200 mL) (some foaming) and diluted with ethyl acetate (250 mL). The organic phase was separated and washed with 100 mL of brine. The organic phase was dried over magnesium sulfate, filtered over celite, and concentrated in vacuo to afford a dark yellow oil. The crude product was purified by silica gel chromatography eluting with 0%-100% ethyl acetate in hexanes. Collected both pure (9.0 g) and impure (3 g) fractions. Purified the impure fractions by silica gel chromatography eluting with 0%-100% ethyl acetate in hexanes affording, in total, tert-butyl 2,2-dimethyl-4-[3-[(6-sulfamoyl-2-pyridyl)amino]propyl]pyrrolidine-1-carboxylate (10.0 g, 69%). $^1$H NMR (400 MHz, dimethyl sulfoxide-d$_6$) δ 7.52 (dd, J=8.5, 7.2 Hz, 1H), 7.07 (s, 2H), 6.95 (dd, J=7.2, 0.7 Hz, 2H), 6.61 (d, J=8.5 Hz, 1H), 3.55 (q, J=9.1 Hz, 1H), 3.32-3.24 (m, 2H), 2.79 (q, J=10.0 Hz, 1H), 2.13 (d, J=16.1 Hz, 1H), 1.96-1.82 (m, 1H), 1.51 (dt, J=18.0, 9.3 Hz, 2H), 1.37 (dd, J=12.9, 10.6 Hz, 15H), 1.24 (s, 3H). ESI-MS m/z calc. 412.21442, found 413.1 (M+1)+; Retention time: 2.34 min (LC Method D).

Step 10: tert-Butyl (4S)-2,2-dimethyl-4-[3-[(6-sulfamoyl-2-pyridyl)amino]propyl]pyrrolidine-1-carboxylate

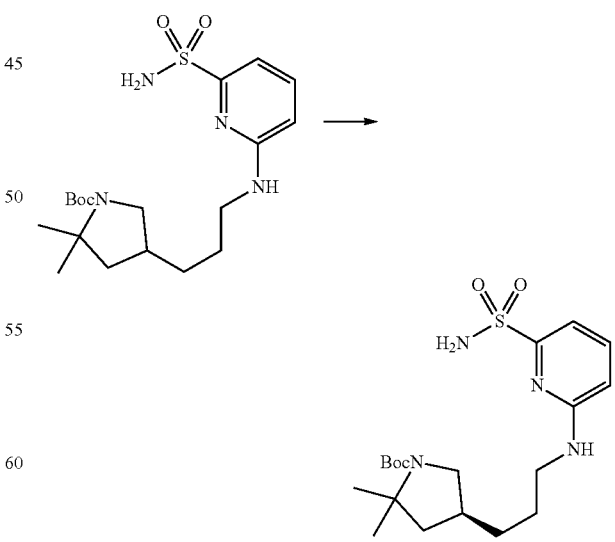

Subjected racemic tert-butyl 2,2-dimethyl-4-[3-[(6-sulfamoyl-2-pyridyl)amino]propyl]pyrrolidine-1-carboxylate (7 g, 16.97 mmol) to chiral separation by SFC chromatography using a ChiralPak IG (250×21.2 mm column, 5 μm particle size) with 40% methanol/60% carbon dioxide mobile phase at 70 mL/min over 11.0 min (injection volume=500 μL of 32 mg/mL solution in methanol) giving as the first peak to elute, tert-butyl (4S)-2,2-dimethyl-4-[3-[(6-sulfamoyl-2-pyridyl)amino]propyl]pyrrolidine-1-carboxylate (3.4481 g, 99%). ESI-MS m/z calc. 412.21442, found 413.2 (M+1)*; Retention time: 0.63 min (LC Method A).

Part C: Synthesis of (14S)-8-[3-(2-{dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione (Compound II)

Step 1: tert-Butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

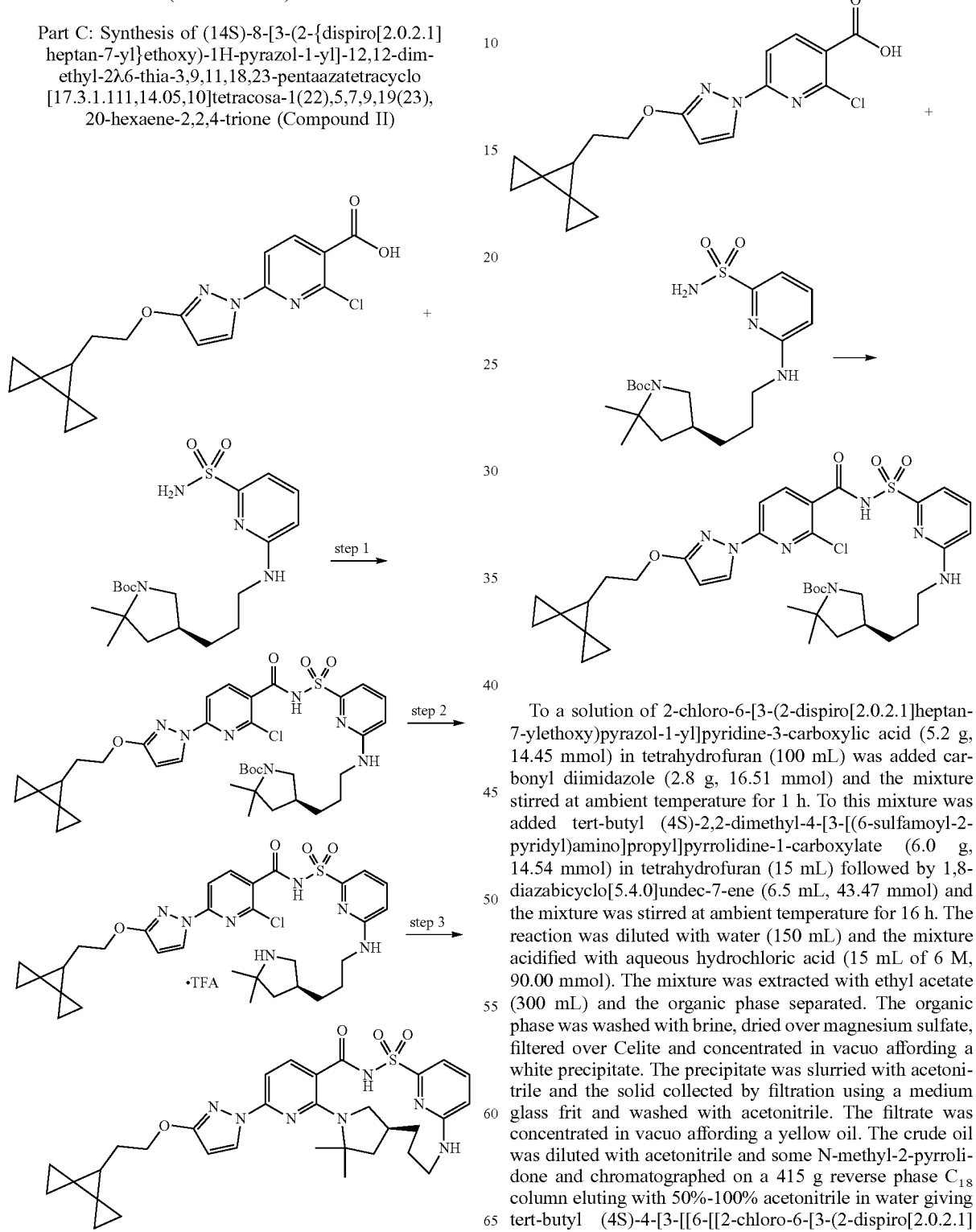

To a solution of 2-chloro-6-[3-(2-dispiro[2.0.2.1]heptan-7-ylethoxy)pyrazol-1-yl]pyridine-3-carboxylic acid (5.2 g, 14.45 mmol) in tetrahydrofuran (100 mL) was added carbonyl diimidazole (2.8 g, 16.51 mmol) and the mixture stirred at ambient temperature for 1 h. To this mixture was added tert-butyl (4S)-2,2-dimethyl-4-[3-[(6-sulfamoyl-2-pyridyl)amino]propyl]pyrrolidine-1-carboxylate (6.0 g, 14.54 mmol) in tetrahydrofuran (15 mL) followed by 1,8-diazabicyclo[5.4.0]undec-7-ene (6.5 mL, 43.47 mmol) and the mixture was stirred at ambient temperature for 16 h. The reaction was diluted with water (150 mL) and the mixture acidified with aqueous hydrochloric acid (15 mL of 6 M, 90.00 mmol). The mixture was extracted with ethyl acetate (300 mL) and the organic phase separated. The organic phase was washed with brine, dried over magnesium sulfate, filtered over Celite and concentrated in vacuo affording a white precipitate. The precipitate was slurried with acetonitrile and the solid collected by filtration using a medium glass frit and washed with acetonitrile. The filtrate was concentrated in vacuo affording a yellow oil. The crude oil was diluted with acetonitrile and some N-methyl-2-pyrrolidone and chromatographed on a 415 g reverse phase $C_{18}$ column eluting with 50%-100% acetonitrile in water giving tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1- carboxylate (4.5 g, 41%). ESI-MS m/z calc. 753.30756, found 754.4 (M+1)+; Retention time: 3.79 min (LC Method D).

Step 2: 2-Chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt)

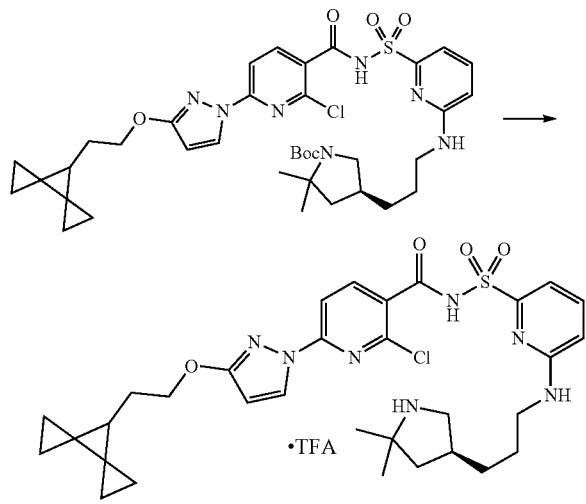

To a solution of tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (5.9 g, 7.821 mmol) in dichloromethane (30 mL) and toluene (15 mL) was added trifluoroacetic acid (6.0 mL, 77.88 mmol) and the mixture stirred at ambient temperature for 18 h. The solvent was removed in vacuo with the bath temp set at 45° C. affording a thick, yellow oil. The oil was diluted with toluene (125 mL) and the solvent removed in vacuo with the bath temp set at 45° C. The oil was diluted with toluene and the solvent removed in vacuo affording a thick, viscous yellow oil, 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 100%) which was used in the next step without further purification. ESI-MS m/z calc. 653.2551, found 654.3 (M+1)+; Retention time: 2.6 min (LC Method B).

Step 3: (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione (Compound II)

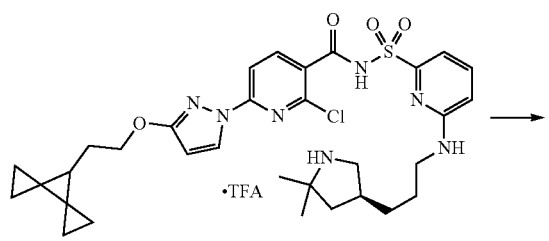

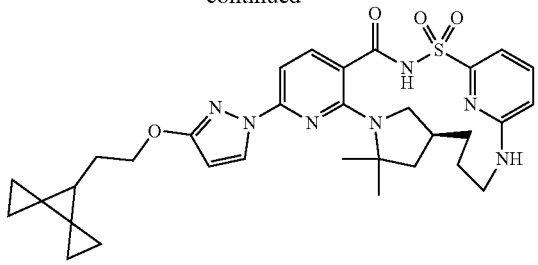

To a solution of 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 7.810 mmol) in NMP (140 mL) was added potassium carbonate (5.3 g, 38.35 mmol). The mixture was purged with nitrogen for 5 min. The mixture was then heated at 150° C. for 22 h. The reaction mixture was cooled to room temperature and added to water (300 mL) affording an off-white solid precipitate. The mixture was carefully acidified with aqueous hydrochloric acid (12 mL of 6 M, 72.00 mmol) affording a foamy slurry. The solid was collected by filtration using a medium glass frit. The wet filter cake was dissolved in ethyl acetate (500 mL) and washed with 200 mL of brine. The aqueous phase was slightly cloudy so it was acidified with a small amount of 6N hydrochloric acid and returned to the organic phase. The aqueous phase was separated and the organic phase was dried over magnesium sulfate, filtered and concentrated in vacuo affording a light yellow oil. This crude product was diluted with acetonitrile and chromatographed on a 415 g $C_{18}$ reverse phase column eluting with 50%-100% acetonitrile in water. The product was isolated as a cream colored foam. The foam was dried in vacuo at 45° C. for 48 h giving (14S)-8-[3-(2-{dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione (Compound II) (3.32 g, 68%). $^1$H NMR (400 MHz, dimethyl sulfoxide-$d_6$) δ 12.48 (s, 1H), 8.20 (d, J=2.8 Hz, 1H), 7.81 (d, J=8.2 Hz, 1H), 7.57 (dd, J=8.5, 7.2 Hz, 1H), 7.05 (d, J=7.1 Hz, 1H), 6.97 (d, J=8.5 Hz, 1H), 6.91 (d, J=8.2 Hz, 1H), 6.71 (d, J=8.5 Hz, 1H), 6.08 (d, J=2.7 Hz, 1H), 4.21 (td, J=6.7, 1.3 Hz, 2H), 3.92 (d, J=12.0 Hz, 1H), 3.16 (s, 1H), 2.95 (d, J=13.3 Hz, 1H), 2.78-2.66 (m, 1H), 2.07 (s, 1H), 1.92-1.72 (m, 4H), 1.60 (s, 6H), 1.51 (s, 3H), 1.47 (t, J=6.5 Hz, 1H), 1.31 (q, J=12.2 Hz, 1H), 0.89-0.77 (m, 4H), 0.69-0.61 (m, 2H), 0.53-0.45 (m, 2H). ESI-MS m/z calc. 617.27844, found 618.4 (M+1)+; Retention time: 10.29 min (LC Method F).

Example 5: Compound II (Free Form) Form A

A reactor was equipped with an overhead stirrer, reflux condenser, N₂ bubble line and outlet, and a temperature probe. A mixture of (14S)-8-bromo-12,12-dimethyl-2λ6-thia-3,9,11,18,23-pentaazatetracyclo[17.3.1.1¹¹,¹⁴.0⁵,¹⁰]tetracosa-1(23),5,7,9,19,21-hexaene-2,2,4-trione (120 g of 86% w/w with IPAc [103.2 g (14S)-8-bromo-12,12-dimethyl-2λ6-thia-3,9,11,18,23-pentaazatetracyclo[17.3.1.1¹¹,¹⁴.0⁵,¹⁰]tetracosa-1(23),5,7,9,19,21-hexaene-2,2,4-trione], 0.21 mol, 1 equiv), 3-(2-(dispiro[2.0.2⁴.1³]heptan-7-yl)ethoxy)-1H-pyrazole (42.6 g, 0.21 mol, 1 equiv), 325 mesh K₂CO₃ (63.4 g, 0.46 mol, 2.2 equiv), CuI (3.3 g, 17.2 mmol, 0.083 equiv) and BuOAc (740 mL) were charged into a reactor. The mixture was stirred at ambient temperature.

Then DMF (300 mL, 2.9 vol) and N,N-dimethylcyclohexane-1,2-diamine (14.6 g or 16.2 ml, 0.1 mol, 0.49 equiv) were charged to the reactor and the mixture was purged with three $N_2$/vacuum/$N_2$ cycles. The mixture was then heated to 120° C. for 4 h, then allowed to cool to ambient temperature. 10% aq w/v oxalic acid (860 mL, 0.96 mol, 4.6 equiv) was added dropwise and the mixture stirred for at least 1 h. The mixture was then filtered to remove suspended solids. The removed solids were washed with (2×120 mL). The layers from the filtrate were separated. The organic layer was washed with 8% aq. w/v trisodium citrate (600 mL). Brine was added as necessary to aid phase separation. The organic layer was washed with 1:1 v/v water/brine (400 mL). The organic layer was filtered through a pad of Celite. The filter pad was washed with IPAc (150 mL). The filtrate was concentrated, then 800 mL of 1-PrOH (7.8 vol) was added and the mixture concentrated. This step was repeated one more time. Toluene (800 mL) was added and the mixture concentrated. This step was repeated one more time to afford a thick slurry. The crude mixture was concentrated to a volume of 300 mL (2.9 vol) of toluene. After stirring the slurry overnight, the solid was collected by filtration and washing the solid with toluene (2×100 mL, 0.97 vol). The solid was dried under vacuum with a nitrogen bleed at 50° C. until the loss on drying was no more than 1.0% to afford Compound II as a white/off-white solid (107.0 g, 83%, 94.5% (AUC) HPLC purity.

Recrystallization: Compound II Form A [22.2 g, 94.6% (AUC) Compound II Form A was suspended in toluene (440 mL, 20 vol based on Compound II Form A) and the mixture heated to reflux. After holding at reflux for NLT 2 h, the mixture was allowed to cool to ambient over 8 h. After stirring at ambient temperature overnight, the solid was collected by filtration washing the solid with toluene (40 mL, 1.8 vol). The solid was dried under vacuum with a nitrogen bleed at 50° C. until the loss on drying was no more than 1.0% to afford Compound II Form A as a white/off-white solid (18.8 g, 84%, 96.8% (AUC) HPLC purity).

Second Recrystallization: Compound II Form A [17.5 g, 97.0% (AUC) Compound II Form A] was suspended in toluene (350 mL, 20 vol based on Compound II Form A) and the mixture heated to reflux. After holding at reflux for no less than 2 h, the mixture was allowed to cool to ambient temperature over 8 h. After stirring at ambient temperature overnight, the solid was collected by filtration washing the solid with toluene (40 mL, 1.8 vol). The solid was dried under vacuum with a nitrogen bleed at 50° C. until the loss on drying was no more than 1.0% to afford Compound II Form A (free form) as a white/off-white solid (15.7 g, 89%, 98.4% (AUC) HPLC purity).

Compound II free Form A is the most stable polymorphic form at water activity ≤0.95 at ambient temperature.

A. X-Ray Powder Diffraction

The XRPD pattern was acquired at room temperature in reflection mode using a Bruker Advance equipped with Vantec-1 detector. A sample was analyzed on a silicon sample holder from 3-40' 2-theta on continuous mode with step size of 0.0144531° and time per step of 0.25 s. The sample was spinning at 15 rpm. The XRPD diffractogram for Compound II (free form) Form A is provided in FIG. 1 and the XRPD data are summarized below in Table 5.

TABLE 5

XRPD signals for crystalline Form A of Compound II (free form)

| XRPD Peaks | Angle (degrees 2-Theta ± 0.2) | Intensity % |
|---|---|---|
| 1 | 20.0 | 100.0 |
| 2 | 23.1 | 63.9 |
| 3 | 16.6 | 56.4 |
| 4 | 23.3 | 52.3 |
| 5 | 9.2 | 51.2 |
| 6 | 24.3 | 42.0 |
| 7 | 18.1 | 41.9 |
| 8 | 16.5 | 40.7 |
| 9 | 11.2 | 38.6 |
| 10 | 21.8 | 37.2 |
| 11 | 11.3 | 33.3 |
| 12 | 18.0 | 32.9 |
| 13 | 14.0 | 31.8 |
| 14 | 24.4 | 29.5 |
| 15 | 22.9 | 29.4 |
| 16 | 23.8 | 29.3 |
| 17 | 5.7 | 26.2 |
| 18 | 18.7 | 24.6 |
| 19 | 18.8 | 24.6 |
| 20 | 18.5 | 22.4 |
| 21 | 22.5 | 19.2 |
| 22 | 20.4 | 17.7 |
| 23 | 15.1 | 14.9 |
| 24 | 26.5 | 14.3 |
| 25 | 13.7 | 13.8 |
| 26 | 22.2 | 13.8 |
| 27 | 27.3 | 11.9 |
| 28 | 15.0 | 11.7 |
| 29 | 14.8 | 10.4 |

B. Single Crystal Elucidation

Single crystals having the Compound II (free form) Form A structure were grown from acetone/heptane. X-ray diffraction data were acquired at 298K on a Bruker diffractometer equipped with Mo $K_\alpha$ radiation (λ=0.71073 Å) and a CCD detector. The structure was solved and refined using SHELX programs (Sheldrick, G. M., Acta Cryst., (2008) A64, 112-122) and results are summarized in Table 6 below.

TABLE 6

Single crystal elucidation of Compound II (free form) Form A

| Crystal System | Monoclinic |
|---|---|
| Space Group | $P2_1$ |
| a (Å) | 15.477(3) |
| b (Å) | 12.741(2) |
| c (Å) | 16.369(3) |
| α (°) | 90 |
| β (°) | 99.350(5) |
| γ (°) | 90 |
| V (Å³) | 3185.1(9) |
| Z/Z' | 2/2 |
| Temperature | 298 K |

C. Solid State NMR

1. Solid State NMR Experimental (Applies to all Crystalline Forms of Compound II):

Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^1$H MAS T1 saturation recovery relaxation experiment in order to set up proper recycle delay of the $^{13}$C cross-polarization (CP) MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Carbon spectra were recorded with proton decoupling using TPPM15 decoupling sequence with the field strength of approximately 100 kHz.

2. Solid State NMR for Compound II (Free Form) Form A

Figure 2:
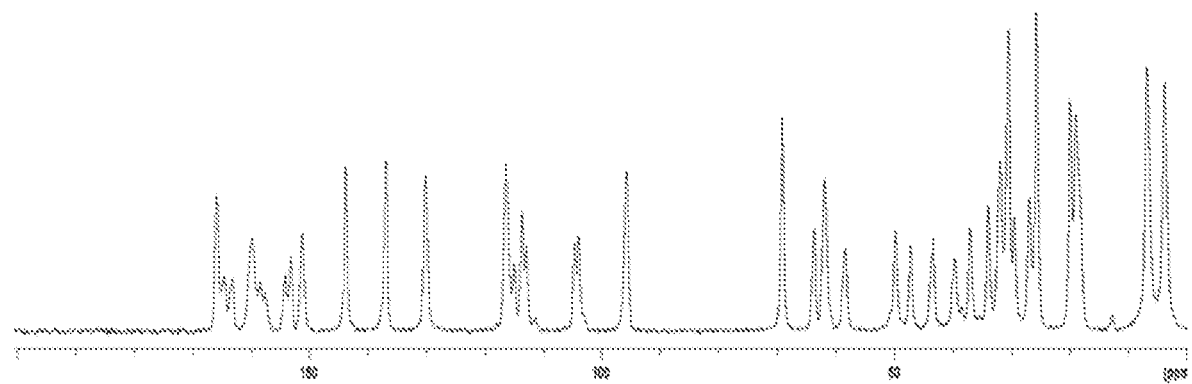
FIG. 2 shows a $^{13}C$ solid state NMR spectrum of crystalline Compound I (free form) Form A.

Solid state $^{13}C$ NMR data for Compound II (free form) Form A is provided in FIG. 2 and summarized in Table 7 below.

TABLE 7

Solid State NMR of Compound II (free form) Form A

| Peak # | Chem Shift [ppm] ± 0.2 ppm | Intensity [rel] |
|---|---|---|
| 1 | 165.9 | 42.7 |
| 2 | 164.6 | 16.9 |
| 3 | 163.2 | 16.6 |
| 4 | 159.8 | 29.3 |
| 5 | 158.5 | 14.9 |
| 6 | 157.6 | 11.6 |
| 7 | 154.1 | 17.7 |
| 8 | 153.2 | 22.5 |
| 9 | 151.3 | 30.6 |
| 10 | 143.8 | 51.7 |
| 11 | 136.9 | 53.8 |
| 12 | 130.2 | 48.5 |
| 13 | 116.4 | 52.2 |
| 14 | 115.1 | 20.7 |
| 15 | 113.7 | 37.4 |
| 16 | 112.9 | 26.1 |
| 17 | 104.6 | 27.2 |
| 18 | 103.9 | 29.5 |
| 19 | 95.7 | 49.9 |
| 20 | 69.1 | 67.4 |
| 21 | 63.6 | 31.9 |
| 22 | 61.8 | 47.4 |
| 23 | 58.3 | 25.8 |
| 24 | 49.7 | 30.8 |
| 25 | 47.2 | 26.4 |
| 26 | 43.3 | 28.8 |
| 27 | 39.6 | 22.8 |
| 28 | 37.0 | 32.0 |
| 29 | 33.9 | 38.8 |
| 30 | 31.9 | 53.4 |
| 31 | 30.5 | 94.5 |
| 32 | 29.5 | 35.6 |
| 33 | 26.9 | 41.6 |
| 34 | 25.6 | 100.0 |
| 35 | 19.9 | 72.7 |
| 36 | 19.0 | 67.8 |
| 37 | 6.6 | 82.8 |
| 38 | 3.7 | 78.1 |

D. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed a single melting endothermic peak at ~227° C.

Example 6: Compound II Calcium Salt Hydrate Form A

Compound II calcium salt hydrate Form A is the most kinetically favored calcium salt hydrate form, providing higher dissolution, solubility, and exposure than the other calcium salt hydrate forms.

Compound II calcium salt hyrate Form A is prepared by charging 0.2 mmol of Compound II (free form) Form A and 0.1 mmol of Ca(OMe)$_2$ dry powder with IPA at ~45 mg/mL and spiked with ~10% of water and heated to 70° C. Initially, all solids dissolved. After 5 min, white solid precipitated out. The resulting slurry was stirred for 4 d at room temperature. The solid was isolated as Compound II calcium salt hydrate Form A by vacuum filtration and dried under vacuum at 40° C. for overnight (~78% isolated yield).

An alternative method of preparing Compound II calcium salt hydrate Form A utilized 10 g of Compound I (free form Form A) charged with 63 mL IPA and 7 mL water. The slurry was heated to 55-65° C. The mixture was charged with 1.1 equiv of NaOH. The mixture was stirred until the solution turned homogeneous. The solution was then cooled to 25° C. and seeded with 0.1 g of Compound II sodium salt hydrate Form A. The slurry was stirred for 18 h. The solution was then heated to 45° C. The slurry was seeded with 0.1 g of Compound II calcium salt hydrate Form A. A solution of 0.55 equiv CaCl$_2$), 9 mL IPA, and 1 mL water were added over a 5 h period of time. The resulting slurry was stirred for 2 h. The slurry was cooled to 20° C. over a 5 h period of time. The resulting solids were collected by vacuum filtration and the resulting wet cake was washed with 50 mL of water. The washed wet cake was allowed to air-dry for 1 h. The air-dried wet cake was transferred to a vacuum oven at 45° C. with a slight nitrogen bleed for 20 h to yield crystalline Compound II calcium salt hydrate Form A (8.5 g, 82% isolated yield).

Figure 3:
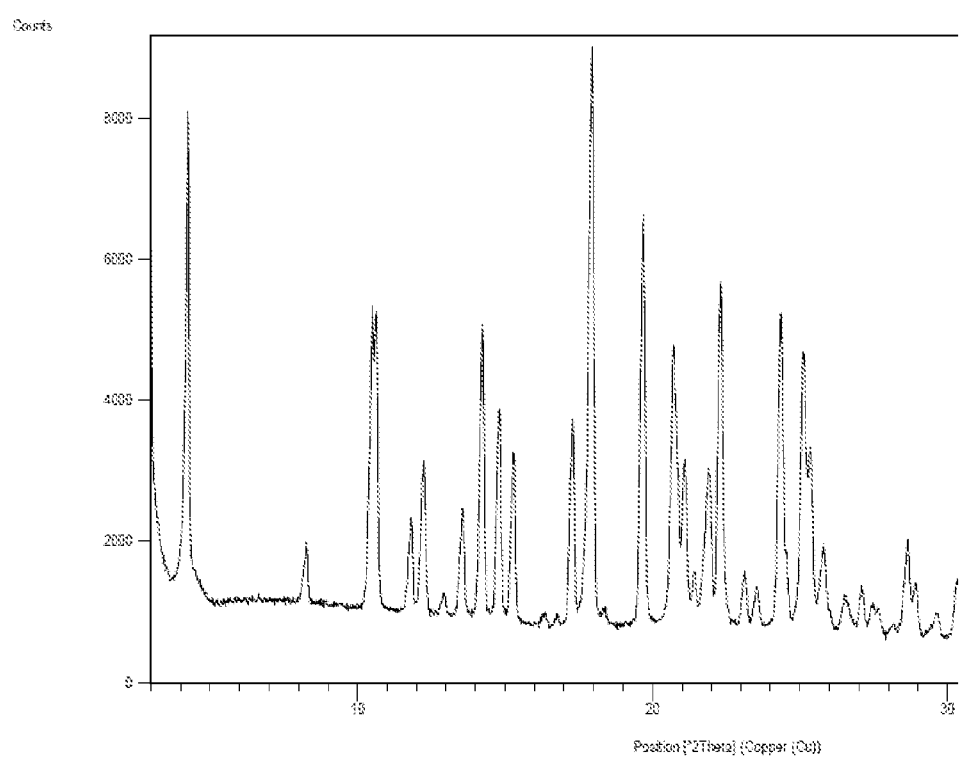
FIG. 3 provides an XRPD pattern of crystalline Compound I calcium salt hydrate Form A.

A. X-Ray Powder Diffraction:

The XRPD patterns were acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound II calcium salt hydrate Form A is shown in FIG. 3 and summarized in Table 8.

TABLE 8

XRPD signals for crystalline Compound II calcium salt hydrate Form A

| XRPD Peaks | Angle (degrees 2-Theta ± 0.2) | Intensity % |
|---|---|---|
| 1 | 18.0 | 100.0 |
| 2 | 4.2 | 81.7 |
| 3 | 19.7 | 71.2 |
| 4 | 22.3 | 59.5 |
| 5 | 17.8 | 57.1 |
| 6 | 24.4 | 54.9 |
| 7 | 10.5 | 52.5 |
| 8 | 10.6 | 51.9 |
| 9 | 14.2 | 50.9 |
| 10 | 20.7 | 48.8 |
| 11 | 25.1 | 48.1 |
| 12 | 19.6 | 42.1 |
| 13 | 14.8 | 36.8 |
| 14 | 17.3 | 35.8 |
| 15 | 25.3 | 31.2 |
| 16 | 15.3 | 29.2 |
| 17 | 21.1 | 28.9 |
| 18 | 12.2 | 26.6 |
| 19 | 21.9 | 26.5 |
| 20 | 22.0 | 24.5 |
| 21 | 13.6 | 19.1 |
| 22 | 11.8 | 16.6 |
| 23 | 28.7 | 15.9 |
| 24 | 25.8 | 14.6 |
| 25 | 8.3 | 10.3 |

B. Single Crystal Elucidation

Crystals having the Compound II calcium salt hydrate Form A structure were grown by dissolving 1 mg of Compound II calcium salt hydrate Form A in 350 μL of a 90/10 mixture of dichloroethane/ethanol and then was vapor diffused with pentane over several days. X-ray diffraction data were acquired at both 100K and 298K on a Bruker diffractometer equipped with Cu $K_\alpha$ radiation ($\lambda$=1.5478 Å) and a CCD detector. The structure was solved and refined using SHELX programs (Sheldrick, G. M., Acta Cryst., (2008) A64, 112-122) and results are summarized in Table 9 below.

TABLE 9

Single crystal elucidation of Compound II calcium salt hydrate Form A

| Crystal System: | Monoclinic | Monoclinic |
|---|---|---|
| Space Group: | C2 | C2 |
| a (Å) | 11.1298(4) | 11.1871(10) |
| b (Å) | 13.7688(5) | 13.8793(12) |
| c (Å) | 22.2139(8) | 22.4114(18) |
| α (°) | 90 | 90 |
| β (°) | 101.9330(10) | 101.477(4) |
| γ (°) | 90 | 90 |
| V (Å³) | 3330.6(2) | 3410.2(5) |
| Z/Z' | 2/0.5 | 2/0.5 |
| Temperature | 100 K | 298 K |

C. Solid State NMR

Figure 4:
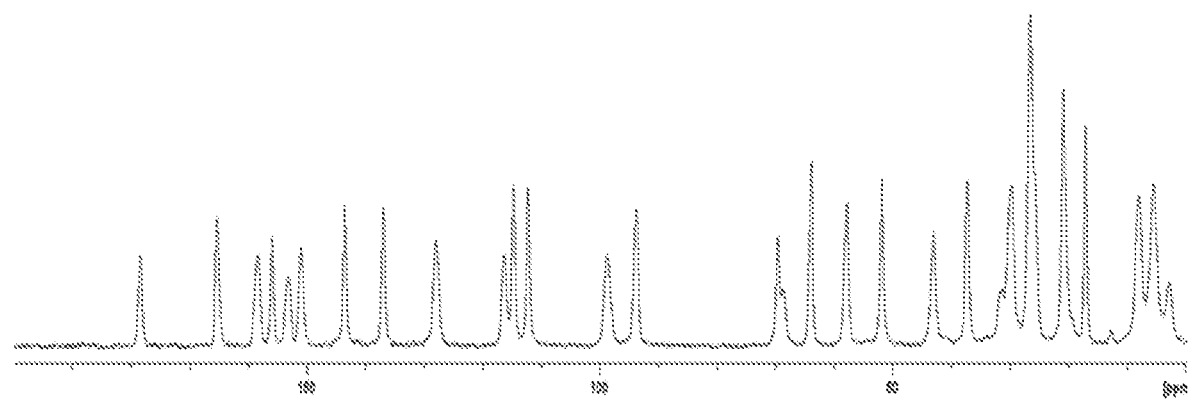
FIG. 4 shows a $^{13}C$ solid state NMR spectrum of Compound I calcium salt hydrate Form A.

Solid state $^{13}$C NMR spectrum for Compound II calcium salt hydrate Form A is provided in FIG. 4 and summarized in Table 10.

TABLE 10

Solid state NMR of Compound II calcium salt hydrate Form A

| Peak # | Chem Shift [ppm] ± 0.2 | Intensity [rel] |
|---|---|---|
| 1 | 178.3 | 27.0 |
| 2 | 165.2 | 38.8 |
| 3 | 158.2 | 27.6 |
| 4 | 155.8 | 32.7 |
| 5 | 153.1 | 20.5 |
| 6 | 150.9 | 29.9 |
| 7 | 143.4 | 42.1 |
| 8 | 136.8 | 41.3 |
| 9 | 127.9 | 31.5 |
| 10 | 116.3 | 27.4 |
| 11 | 114.6 | 48.2 |
| 12 | 112.1 | 47.4 |
| 13 | 98.6 | 27.4 |
| 14 | 93.6 | 41.2 |
| 15 | 69.5 | 33.0 |
| 16 | 68.6 | 17.0 |
| 17 | 63.8 | 55.6 |
| 18 | 57.7 | 43.1 |
| 19 | 51.8 | 50.2 |
| 20 | 42.9 | 34.2 |
| 21 | 37.2 | 49.9 |
| 22 | 31.2 | 16.9 |
| 23 | 29.6 | 48.1 |
| 24 | 26.4 | 100.0 |
| 25 | 20.8 | 77.4 |
| 26 | 17.0 | 65.8 |
| 27 | 7.8 | 44.7 |
| 28 | 5.3 | 48.8 |
| 29 | 2.6 | 18.7 |

D. Differential Scanning Calorimetry Analysis:

A DSC thermogram was obtained using TA Instruments DSC Q2000. Sample was heated at 10° C./min from 30° C. to 350° C. The thermogram showed an endothermic peak at ~223° C.

Example 7: Compound II Calcium Salt Hydrate Form D

Compound II calcium salt hydrate Form D is the most stable form of calcium salt hydrate under certain conditions, such as in mixtures of ethanol and water.

Approximately 25 mg of Compound II calcium salt hydrate Form A was charged with 0.5 mL of EtOH:water 67:33 w/w. The slurry was heated to 65° C. for 8 d. The resulting solid collected by vacuum filtration was Compound II calcium salt hydrate Form D.

Alternatively, Compound II calcium salt hydrate Form D was prepared from 89 g of Compound II sodium hydrate Form A charged with 1080 mL IPA and 120 mL water. The slurry was heated to 55-65° C. The slurry was charged with 18 g of Compound II calcium salt hydrate Form D seed. The slurry was wet-milled as a solution of 0.55 equiv $CaCl_2$), 81 mL IPA and 9 mL water was added over a 5 h period of time. The wet mill was allowed to run until the X-ray powder diffraction confirmed that the slurry was all Compound I calcium salt hydrate Form D. The resulting solids were collected by vacuum filtration and wet cake was washed with 350 mL of water. The washed wet cake was allowed to air-dry for 1 h. The air-dried wet cake was transferred to a vacuum oven at 45° C. with a slight nitrogen bleed for 20 h to yield crystalline Compound II calcium salt hydrate Form D (83.15 g, 90.6% isolated yield).

Compound II calcium salt hydrate Form D is the most stable polymorphic form in IPA/water at water activity 0.1-0.95 from ambient temperature to 60° C.

Figure 5:
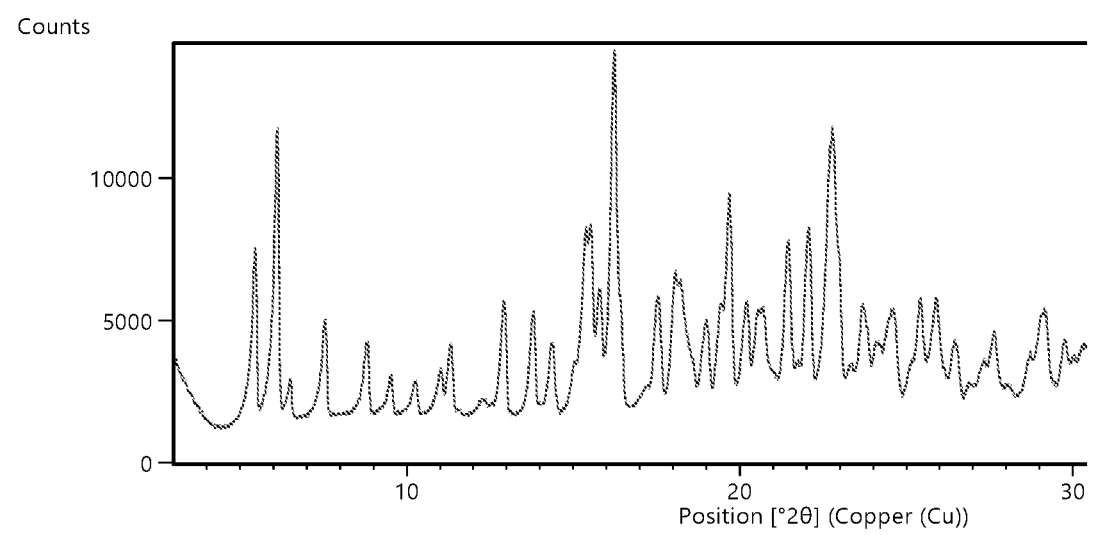
FIG. 5 provides an XRPD pattern of crystalline Compound I calcium salt hydrate Form D.

A. X-Ray Powder Diffraction:

X-ray powder diffraction (XRPD) spectra were recorded at room temperature in reflection mode using a PANalytical Empyrean system equipped with a sealed tube source and a PIXcel 1D Medipix-2 detector (Malvern PANalytical Inc, Westborough, Massachusetts). The X-Ray generator operated at a voltage of 45 kV and a current of 40 mA with copper radiation (1.54060 Å). The powder sample was placed in a back filled sample holder and loaded into the instrument. The sample was scanned over the range of about 3° to about 40° 2θ with a step size of 0.0131303° and 49.725 s per step. The XRPD diffractogram for Compound I calcium salt hydrate Form D is shown in FIG. 5 and summarized in Table 11.

TABLE 11

XRPD signals for crystalline Compound II calcium salt hydrate Form D

| XRPD Peaks | Angle (degrees 2-Theta ± 0.2) | Intensity % |
|---|---|---|
| 1 | 16.2 | 100.0 |
| 2 | 22.8 | 79.8 |
| 3 | 6.1 | 79.3 |
| 4 | 19.7 | 61.5 |
| 5 | 15.5 | 53.6 |
| 6 | 15.4 | 53.0 |
| 7 | 22.1 | 52.9 |
| 8 | 21.5 | 49.1 |
| 9 | 5.5 | 47.0 |
| 10 | 23.0 | 43.3 |
| 11 | 18.1 | 41.5 |
| 12 | 18.2 | 38.9 |
| 13 | 15.8 | 36.7 |
| 14 | 17.5 | 34.6 |
| 15 | 25.9 | 34.1 |
| 16 | 25.4 | 16 |
| 17 | 12.9 | 17 |
| 18 | 20.2 | 18 |
| 19 | 19.4 | 19 |

TABLE 11-continued

XRPD signals for crystalline Compound II calcium salt hydrate Form D

| XRPD Peaks | Angle (degrees 2-Theta ± 0.2) | Intensity % |
|---|---|---|
| 20 | 23.7 | 20 |
| 21 | 20.7 | 21 |
| 22 | 16.4 | 22 |
| 23 | 20.6 | 23 |
| 24 | 13.8 | 30.5 |
| 25 | 7.5 | 28.4 |
| 26 | 19.03 | 28.2 |
| 27 | 19.0 | 27.7 |
| 28 | 29.1 | 27.5 |
| 29 | 24.6 | 26.3 |
| 30 | 27.6 | 25.1 |
| 31 | 29.8 | 33.6 |
| 32 | 8.8 | 33.5 |
| 33 | 26.5 | 33.2 |
| 34 | 14.4 | 32.4 |
| 35 | 11.3 | 32.1 |
| 36 | 24.1 | 31.3 |
| 37 | 28.7 | 31.2 |
| 38 | 27.3 | 30.6 |
| 39 | 18.6 | 17.4 |
| 40 | 23.3 | 16.3 |
| 41 | 15.0 | 15.7 |
| 42 | 11.0 | 15.3 |
| 43 | 9.5 | 13.4 |
| 44 | 6.5 | 12.6 |
| 45 | 10.3 | 12.2 |

B. Single Crystal Elucidation

Crystals were selected from Compound II calcium salt hydrate Form D seeded process in ethanol/water. X-ray diffraction data were acquired at 100K on a Bruker diffractometer equipped with Cu $K_a$ radiation (1=1.5478), provided by a Rigaku MM007HF rotating anode, and an CMOS detector. The structure was solved and refined using SHELX program (Sheldrick, G. M., Acta Cryst., (2008) A64, 112-122) and results are summarized in Table 12.

TABLE 12

Single crystal elucidation of Compound II calcium salt hydrate Form D

| Crystal System | Triclinic |
|---|---|
| Space Group | P1 |
| a (Å) | 12.783(3) |
| b (Å) | 16.639(3) |
| c (Å) | 18.190(4) |
| α (°) | 64.932(12) |
| β (°) | 75.095(14) |
| γ (°) | 68.220(13) |
| V (Å³) | 3231.3(13) |
| Z/Z' | 1/1 |
| Temperature | 100 K |

C. Solid State NMR:

Solid state $^{13}C$ NMR spectrum for Compound I calcium salt hydrate Form C is provided in FIG. 6 and summarized in Table 13.

TABLE 13

Solid state NMR of Compound II calcium salt hydrate Form D

| Peak # | Chem Shift [ppm] ± 0.2 | Intensity [rel] |
|---|---|---|
| 1 | 179.8 | 22.0 |
| 2 | 176.9 | 14.0 |
| 3 | 176.3 | 13.7 |
| 4 | 165.8 | 34.1 |
| 5 | 164.4 | 33.6 |
| 6 | 160.9 | 33.0 |
| 7 | 159.9 | 32.8 |
| 8 | 158.5 | 23.1 |
| 9 | 154.8 | 22.2 |
| 10 | 154.3 | 24.4 |
| 11 | 153.3 | 16.2 |
| 12 | 149.5 | 33.1 |
| 13 | 147.9 | 20.4 |
| 14 | 143.8 | 28.0 |
| 15 | 142.5 | 27.7 |
| 16 | 142.0 | 29.6 |
| 17 | 140.4 | 25.0 |
| 18 | 139.5 | 19.3 |
| 19 | 137.3 | 20.4 |
| 20 | 136.7 | 29.3 |
| 21 | 130.2 | 29.6 |
| 22 | 127 | 16.4 |
| 23 | 125.6 | 28.3 |
| 24 | 120.9 | 11.5 |
| 25 | 118.5 | 47.2 |
| 26 | 117.5 | 27.1 |
| 27 | 115.0 | 7.6 |
| 28 | 113.8 | 15.0 |
| 29 | 112.0 | 10.9 |
| 30 | 110.7 | 42.5 |
| 31 | 108.8 | 10.6 |
| 32 | 100.1 | 13.7 |
| 33 | 98.6 | 36.6 |
| 34 | 95.2 | 23.9 |
| 35 | 94.7 | 41.8 |
| 36 | 93.2 | 26.1 |
| 37 | 92.6 | 22.0 |
| 38 | 70.1 | 27.2 |
| 39 | 68.3 | 42.8 |
| 40 | 63.5 | 46.0 |
| 41 | 62.3 | 30.6 |
| 42 | 61.4 | 24.0 |
| 43 | 58.4 | 4.2 |
| 44 | 56.7 | 20.9 |
| 45 | 55.2 | 28.2 |
| 46 | 52.1 | 22.1 |
| 47 | 51.8 | 23.1 |
| 48 | 50.3 | 16.2 |
| 49 | 49.4 | 30.2 |
| 50 | 44.3 | 11.2 |
| 51 | 40.4 | 9.3 |
| 52 | 39.3 | 38.6 |
| 53 | 35.0 | 41.6 |
| 54 | 33.4 | 35.8 |
| 55 | 32.0 | 41.7 |
| 56 | 29.8 | 45.0 |
| 57 | 28.4 | 45.8 |
| 58 | 26.9 | 43.7 |
| 59 | 24.7 | 31.2 |
| 60 | 20.1 | 100.0 |
| 61 | 18.8 | 62.3 |
| 62 | 18.5 | 64.2 |
| 63 | 18.2 | 58.0 |
| 64 | 6.5 | 60.3 |
| 65 | 5.1 | 47.4 |
| 66 | 4.7 | 47.8 |
| 67 | 3.8 | 54.4 |
| 68 | 3.3 | 52.2 |
| 69 | 1.6 | 22.5 |

D. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed multiple endothermic peaks at ~182° C., and ~208° C.

Example 8: Efficacy Data for 250 mg of Compound I

In a clinical trial, a comparative study was conducted on absolute changes in SwCl at 12 weeks in subjects with gating mutations where were on stable treatment with ivacaftor. Compound I was considered generally safe and well tolerated at 150 mg and 250 mg for 12 weeks. The 250 mg dose demonstrated improvement in SwCl at week 12 compared to the ivacaftor baseline whereas the 150 mg dose of Compound 1 demonstrated decrease in SwCl compared to ivacaftor baseline.

TABLE 14

Analysis of absolute Change in SwCl

|  | Ivacaftor 150 mg q12h N = 11 | Compound I 150 mg qd N = 23 | Compound I 250 mg qd N = 24 |
| --- | --- | --- | --- |
| Baseline; Mean (SD) | 54.6 (23.1) | 52.0 (16.6) | 55.0 (26.5) |
| Absolute change at Week 12: |  |  |  |
| LS mean (SE) | 0.9 (5.2) | 3.3 (3.9) | −6.5 (3.8) |
| 95% CI of LS mean | (−9.5, 11.3) | (−4.6, 11.2) | (−14.1, 1.2) |
| LS mean difference vs Ivacaftor, 95% CI |  | 2.4 (−10.6, 15.5) | −7.3 (−20.2, 5.6) |

Example 9: Preparation of Exemplary Tablet Formulation

The intragranular components in Table 15 (Compound I spray dried dispersion (SDD), Compound II calcium salt hydrate Form D, Compound III SDD, microcrystalline cellulose, and croscarmellose sodium) were weighed and sieved through a screen and placed in a bin blender. These components were blended and combined to prepare the intragranular powder blend. The intragranular powder blend was dry granulated using a roller compactor and then milled into granules. The extragranular microcrystalline cellulose was weighed, passed through a screen, and blended with the milled granules in a bin blender. Magnesium stearate was weighed and sieved, then added to the bin blender and blended. The blended components were compressed using a power-assisted rotary tablet press to prepare a table with the required core weight and hardness. The tablets were then placed in a coater to add a nonfunctional coating.

TABLE 15

Exemplary Tablet Formulation Comprising 125 mg Compound I, 10.6 mg Compound II calcium salt hydrate Form D, and 50 mg Compound III.

|  | Ingredient | Amount per tablet (mg) |
| --- | --- | --- |
| Intragranular | Compound I SDD (80 wt % Compound I, 19.5 wt % hypromellose acetate succinate, and 0.5 wt % sodium lauryl sulfate) | 156.3 |
|  | Compound II calcium salt hydrate Form D | 10.6 |
|  | Compound III SDD (80 wt % Compound III, 20 wt % hypromellose) | 62.5 |
|  | Microcrystalline cellulose | 55.1 |
|  | Croscarmellose Sodium | 22.8 |
| Extragranular | Microcrystalline cellulose | 68.9 |
|  | Magnesium Stearate | 3.8 |
| Film Coat | Opadry 20A100021 | 11.4 |
| Total |  | 391.4 |

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A method of treating cystic fibrosis comprising daily administration of:

(a) 250 mg of Compound I:

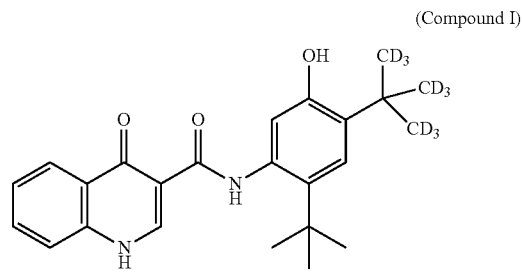 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

(Compound I)

or an equivalent amount of a pharmaceutically acceptable salt thereof; and (b) 21.24 mg Compound II calcium salt hydrate Form D:

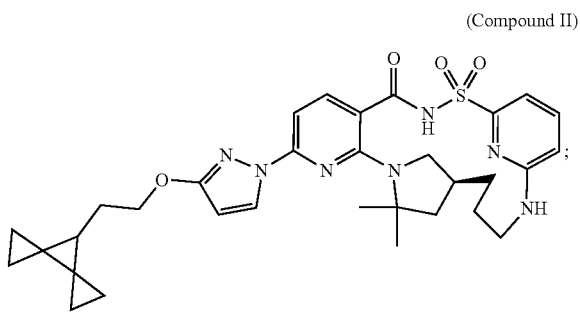 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]
(Compound II)

and (c) 100 mg of Compound III:

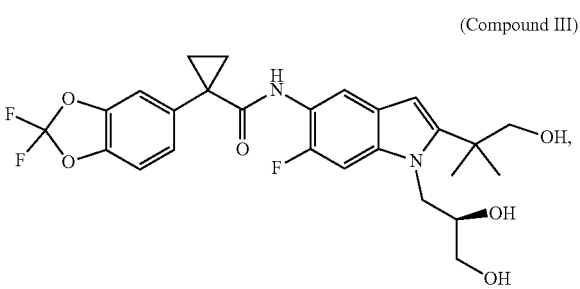 [SMILES: CC(C)(CO)c1cc2cc(NC(=O)C3(c4ccc5c(c4)OC(F)(F)O5)CC3)c(F)cc2n1C[C@@H](O)CO]
(Compound III)

or an equivalent amount of a pharmaceutically acceptable salt thereof.

2. A method of treating cystic fibrosis comprising daily administration of:

(a) 250 mg of Compound I:

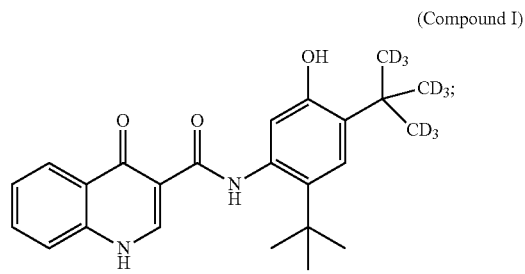 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]
(Compound I)

(b) 21.240 mg of Compound II calcium salt hydrate Form D:

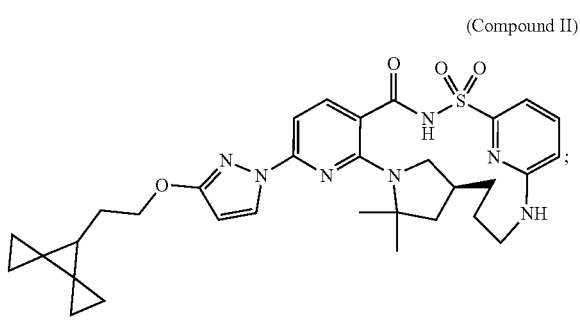 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]
(Compound II)

and (c) 100 mg of Compound III:

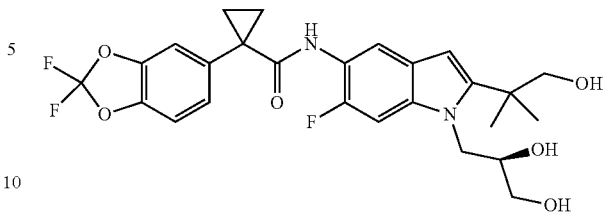
(Compound III), to a patient in need thereof.

3. The method of claim 1 or claim 2, wherein Compounds I, II, and III are administered in separate compositions.

4. The method of claim 1 or claim 2, wherein Compounds I, II, and III are administered in a single composition.

5. The method of claim 1 or claim 2, wherein Compounds I, II, and III are administered as two compositions once daily, each composition comprising 125 mg of Compound I, 10.62 mg of Compound II calcium salt hydrate Form D, and 50 mg of Compound III.

6. The method of claim 1, wherein the patient is homozygous for the F508del cystic fibrosis transmembrane conductance regulator (CFTR) mutation or has an F508del/minimal function CFTR genotype, a F508del/gating CFTR genotype, or a F508del/residual function CFTR genotype.

7. The method of claim 1, wherein the patient has a heterozygous CFTR genotype and has one F508del CFTR mutation.

8. The method of claim 7, wherein the patient has one CFTR mutation selected from:

| | | |
|---|---|---|
| 711 + 3A > G | L206W | K1060T |
| 2789 + 5G > A | R347H | A1067T |
| 3272 − 26A > G | R352Q | G1069R |
| 3849 + 10 kb C > T | A455E | R1070Q |
| E56K | S549N | R1070W |
| P67L | S549R | F1074L |
| R74W | G551D | D1152H |
| D110E | G551S | G1244E |
| D110H | D579G | S1251N |
| R117C | E831X | S1255P |
| R117H | S945L | D1270N |
| G178R | S977F | G1349D |
| E193K | F1052V. | |

9. The method of claim 7, wherein the patient has one CFTR mutation selected from:

| | | |
|---|---|---|
| 3141del9 | E822K | G1244E |
| 546insCTA | F191V | G1249R |
| A46D | F311del | G1349D |
| A120T | F311L | H139R |
| A234D | F508C | H199Y |
| A349V | F508C; S1251N | H939R |
| A455E | F575Y | H1054D |
| A554E | F1016S | H1085P |
| A1006E | F1052V | H1085R |
| A1067T | F1074L | H1375P |
| D110E | F1099L | I148T |
| D110H | G27R | I175V |
| D192G | G85E | I336K |
| D443Y | G126D | I502T |
| D443Y; G576A; R668C | G178E | I601F |
| D579G | G178R | I618T |
| D614G | G194R | I807M |
| D836Y | G194V | I980K |

-continued

| | | |
|---|---|---|
| D924N | G314E | I1027T |
| D979V | G463V | I1139V |
| D1152H | G480C | I1269N |
| D1270N | G551D | I1366N |
| E56K | G551S | K1060T |
| E60K | G576A | L15P |
| E92K | G576A; R668C | L165S |
| E116K | G622D | L206W |
| E193K | G628R | L320V |
| E403D | G970D | L346P |
| E474K | G1061R | L453S |
| E588V | G1069R | L967S |
| L997F | R117P | S945L |
| L1077P | R170H | S977F |
| L1324P | R258G | S1159F |
| L1335P | R334L | S1159P |
| L1480P | R334Q | S1251N |
| M152V | R347H | S1255P |
| M265R | R347L | T338I |
| M952I | R347P | T1036N |
| M952T | R352Q | T1053I |
| M1101K | R352W | V201M |
| P5L | R553Q | V232D |
| P67L | R668C | V456A |
| P205S | R751L | V456F |
| P574H | R792G | V562I |
| Q98R | R933G | V754M |
| Q237E | R1066H | V1153E |
| Q237H | R1070Q | V1240G |
| Q359R | R1070W | V1293G |
| Q1291R | R1162L | W361R |
| R31L | R1283M | W1098C |
| R74Q | R1283S | W1282R |
| R74W | S13F | Y109N |
| R74W; D1270N | S341P | Y161D |
| R74W; V201M | S364P | Y161S |
| R74W; V201M; D1270N | S492F | Y563N |
| R75Q | S549N | Y1014C |
| R117C | S549R | Y1032C |
| R117G | S589N | |
| R117H | S737F | |
| R117L | S912L | | wherein D443Y; G576A; R668C, R74W; D1270N, R74W; V201M, R74W; V201M; D1270N, F508C; S1251N, and G576A; R668C are complex/compound mutations where a single allele of the CFTR gene has multiple mutations, existing independently of the presence of mutations on the other allele.

10. The method of claim 1, wherein the patient has at least one CFTR mutation selected from:

| | | |
|---|---|---|
| 3141del9 | E822K | G1244E |
| 546insCTA | F191V | G1249R |
| A46D | F311del | G1349D |
| A120T | F311L | H139R |
| A234D | F508C | H199Y |
| A349V | F508C; S1251N | H939R |
| A455E | F575Y | H1054D |
| A554E | F1016S | H1085P |
| A1006E | F1052V | H1085R |
| A1067T | F1074L | H1375P |
| D110E | F1099L | I148T |
| D110H | G27R | I175V |
| D192G | G85E | I336K |
| D443Y | G126D | I502T |
| D443Y; G576A; R668C | G178E | I601F |
| D579G | G178R | I618T |
| D614G | G194R | I807M |
| D836Y | G194V | I980K |
| D924N | G314E | I1027T |
| D979V | G463V | I1139V |
| D1152H | G480C | I1269N |
| D1270N | G551D | I1366N |
| E56K | G551S | K1060T |
| E60K | G576A | L15P |
| E92K | G576A; R668C | L165S |
| E116K | G622D | L206W |
| E193K | G628R | L320V |
| E403D | G970D | L346P |
| E474K | G1061R | L453S |
| E588V | G1069R | L967S |
| L997F | R117P | S945L |
| L1077P | R170H | S977F |
| L1324P | R258G | S1159F |
| L1335P | R334L | S1159P |
| L1480P | R334Q | S1251N |
| M152V | R347H | S1255P |
| M265R | R347L | T338I |
| M952I | R347P | T1036N |
| M952T | R352Q | T1053I |
| M1101K | R352W | V201M |
| P5L | R553Q | V232D |
| P67L | R668C | V456A |
| P205S | R751L | V456F |
| P574H | R792G | V562I |
| Q98R | R933G | V754M |
| Q237E | R1066H | V1153E |
| Q237H | R1070Q | V1240G |
| Q359R | R1070W | V1293G |
| Q1291R | R1162L | W361R |
| R31L | R1283M | W1098C |
| R74Q | R1283S | W1282R |
| R74W | S13F | Y109N |
| R74W; D1270N | S341P | Y161D |
| R74W; V201M | S364P | Y161S |
| R74W; V201M; D1270N | S492F | Y563N |
| R75Q | S549N | Y1014C |
| R117C | S549R | Y1032C |
| R117G | S589N | |
| R117H | S737F | |
| R117L | S912L | | wherein D443Y: G576A; R668C, R74W; D1270N, R74W; V201M, R74W; V201M; D1270N, F508C; S1251N, and G576A; R668C are complex/compound mutations where a single allele of the CFTR gene has multiple mutations, existing independently of the presence of mutations on the other allele.

11. The method of claim 1, wherein the Compound II calcium salt hydrate Form D is characterized by an X-ray powder diffractogram (XRPD) having signals at 6.1±0.2 degrees two-theta, 16.2±0.2 degrees two-theta, and 22.8±0.2 degrees two-theta.

12. The method of claim 11, wherein the Compound II calcium salt hydrate Form D is characterized by an XRPD having (a) signals at 6.1±0.2 degrees two-theta, 16.2±0.2 degrees two-theta, and 22.8±0.2 degrees two-theta; and (b) one or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

13. The method of claim 11, wherein the Compound II calcium salt hydrate Form D is characterized by an XRPD having signals at 6.1±0.2 degrees two-theta, 16.2±0.2 degrees two-theta, and 22.8±0.2 degrees two-theta, and 27.6±0.2 degrees two-theta.

14. The method of claim 11, wherein the Compound II calcium salt hydrate Form D is characterized by an XRPD having signals at 6.1±0.2 degrees two-theta, 15.5±0.2 degrees two-theta, 16.2±0.2 degrees two-theta, 19.7±0.2 degrees two-theta, 22.8±0.2 degrees two-theta, and 27.6±0.2 degrees two-theta.

15. The method of claim 1, wherein the Compound II calcium salt hydrate Form D is characterized by an X-ray powder diffractogram substantially similar to FIG. 5.

16. The method of claim 1, wherein the Compound II calcium salt hydrate Form D is characterized by a triclinic crystal system, a P1 space group, and unit cell dimensions measured at 100 K on a Bruker diffractometer equipped with Cu K$_\alpha$ radiation ($\lambda$=1.5478 Å) of

| | | | |
|---|---|---|---|
| a | 12.78 ± .01 Å | α | 64.93 ± .02° |
| b | 16.64 ± .01 Å | β | 75.10 ± .02° |
| c | 18.19 ± .01 Å | γ | 68.22 ± .02°. |

17. The method of claim 1, wherein the Compound II calcium salt hydrate Form D is characterized by a $^{13}$C solid state nuclear magnetic resonance ($^{13}$C ss NMR) spectrum with one or more peaks selected from 130.2±0.2 ppm, 125.6±0.2 ppm, and 35.0±0.2 ppm.

18. The method of claim 17, wherein the Compound II calcium salt hydrate Form D is characterized by a $^{13}$C ss NMR spectrum with one or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm.

19. The method of claim 17, wherein the Compound II calcium salt hydrate Form D is characterized by a $^{13}$C ss NMR spectrum with (a) one or more peaks selected from 130.2±0.2 ppm, 125.6±0.2 ppm, and 35.0±0.2 ppm; and (b) one or more peaks selected from 176.9±0.2 ppm, 160.9±0.2 ppm, 142.0±0.2 ppm, and 98.6±0.2 ppm.

20. The method of claim 1, wherein the Compound II calcium salt hydrate Form D is characterized by a $^{13}$C solid state nuclear magnetic resonance spectrum substantially similar to FIG. 6.

21. The method of claim 1, wherein at least 85% of the Compound II is Compound II calcium salt hydrate Form D.

22. The method of claim 1, wherein at least 95% of the Compound II is Compound II calcium salt hydrate Form D.

* * * * *